(12) United States Patent
Asahara et al.

(10) Patent No.: US 12,066,429 B2
(45) Date of Patent: *Aug. 20, 2024

(54) METHOD FOR INHIBITING THE EXPRESSION OF INFLAMMATION PROMOTING FACTORS

(71) Applicants: National University Corporation Tokyo Medical and Dental University, Tokyo (JP); Nippon Zoki Pharmaceutical Co., Ltd., Osaka (JP)

(72) Inventors: Hiroshi Asahara, Tokyo (JP); Tomoki Chiba, Tokyo (JP); Kentaro Abe, Osaka (JP)

(73) Assignees: National University Corporation Tokyo Medical and Dental University, Tokyo (JP); Nippon Zoki Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/913,376

(22) Filed: Jun. 26, 2020

(65) Prior Publication Data
US 2020/0386741 A1    Dec. 10, 2020

Related U.S. Application Data

(62) Division of application No. 16/300,442, filed as application No. PCT/JP2017/017640 on May 10, 2017, now abandoned.

(30) Foreign Application Priority Data

May 10, 2016 (JP) .................................. 2016-094931
Aug. 22, 2016 (JP) .................................. 2016-162120

(51) Int. Cl.
| C12N 15/11 | (2006.01) |
| C12N 15/10 | (2006.01) |
| C12N 15/113 | (2010.01) |
| C12N 15/63 | (2006.01) |
| G01N 33/50 | (2006.01) |

(52) U.S. Cl.
CPC ..... *G01N 33/5023* (2013.01); *C12N 15/1086* (2013.01); *C12N 15/113* (2013.01); *C12N 15/63* (2013.01); *C12N 2310/14* (2013.01); *C12N 2310/18* (2013.01); *C12N 2320/10* (2013.01); *C12N 2320/50* (2013.01); *G01N 2500/02* (2013.01); *G01N 2500/10* (2013.01)

(58) Field of Classification Search
CPC .............. A61K 31/713; C12N 15/113; C12N 2310/14; C12N 2310/11; C12N 15/111
See application file for complete search history.

(56) References Cited

U.S. PATENT DOCUMENTS

| 2006/0173006 A1* | 8/2006 | Sun .................... A61P 37/00 514/378 |
| 2009/0149403 A1 | 6/2009 | Maclachlan et al. |
| 2009/0181384 A1 | 7/2009 | Nekarda et al. |
| 2010/0099746 A1 | 4/2010 | Yamada et al. |
| 2010/0280101 A1 | 11/2010 | Kohno et al. |
| 2011/0039729 A1 | 2/2011 | DeLisa et al. |
| 2011/0053804 A1 | 3/2011 | Massague et al. |
| 2011/0091419 A1 | 4/2011 | Oft et al. |
| 2013/0274128 A1 | 10/2013 | Reiter |
| 2016/0068916 A1 | 3/2016 | Nekarda et al. |
| 2019/0242875 A1 | 8/2019 | Asahara et al. |
| 2020/0140955 A1 | 5/2020 | Nekarda et al. |
| 2020/0355672 A1 | 11/2020 | Asahara et al. |

FOREIGN PATENT DOCUMENTS

| CA | 2455447 A1 | 9/2003 |
| CN | 101389957 A | 3/2009 |
| JP | 2009159869 A | 7/2009 |
| JP | 2014518610 A | 8/2014 |
| JP | 2014236717 A | 12/2014 |
| JP | 2015522260 A | 8/2015 |
| JP | 2016512032 A | 4/2016 |
| WO | 2003074654 A2 | 9/2003 |
| WO | 2007118149 A2 | 10/2007 |
| WO | 2008044787 A1 | 4/2008 |
| WO | 2011123388 A1 | 10/2011 |
| WO | 2012046063 A2 | 4/2012 |
| WO | 2012122499 A2 | 9/2012 |
| WO | 2013188846 A1 | 12/2013 |
| WO | 2014159791 A1 | 10/2014 |
| WO | 2016106404 A2 | 6/2016 |
| WO | 2016161361 A1 | 10/2016 |
| WO | 2017195809 A1 | 11/2017 |

OTHER PUBLICATIONS

David P. Bartel, MicroRNAs: Target recognition and regulatory functions, Cell, vol. 136, pp. 215-233. (Year: 2009).*

(Continued)

*Primary Examiner* — Dana H Shin
(74) *Attorney, Agent, or Firm* — McNeill Baur PLLC

(57) ABSTRACT

Provided are an expression inhibitor of an inflammation promoting factor based on the discovery of a new factor influencing the expression amount/level of an inflammation promoting factor, and a development tool therefor. Provided are also a diagnostic agent and a diagnosis method for immune diseases, inflammatory diseases, painful conditions and similar. More specifically provided are: an expression inhibitor of an inflammation promoting factor containing at least one kind of inhibitor selected from the group consisting of RBMS2 expression inhibitor and RBMS2 function inhibitor; a screening method using as an indicator the expression or the function of RBMS2; an expression cassette useful for the method; as well as a diagnostic agent containing a product detection agent for RBMS2 gene expression and disease detection method using as an indicator RBMS2 gene expression amount/level.

2 Claims, 19 Drawing Sheets

Specification includes a Sequence Listing.

(56) References Cited

OTHER PUBLICATIONS

Sun et al., RBMS2 inhibits the proliferation by stabilizing p21 mRNA in breast cancer, Journal of Experimental & Clinical Cancer Research, vol. 37:298, pp. 1-14. Supplementary Table 3 is also attached. (Year: 2018).*
Ivashchenko et al., Binding sites of miR-1273 family on the mRNA of target genes, BioMed Research International, vol. 2014, Article ID 620530, 11 pages. (Year: 2014).*
Communication pursuant to Article 94(3) EPC issued in European Application No. 17796169.5, dated Jul. 1, 2020, 7 pages.
Cua et al., "Central Nervous System Expression of IL-10 Inhibits Autoimmune Encephalomyelitis," Journal of Immunology 166:602-608 (2001).
Filion et al., "Monocyte-derived cytokines in multiple sclerosis," Clin. Exp. Immunol. 131:324-334 (2003).
Katsikis et al., "Immunoregulatory Role of Interleukin 10 in Rheumatoid Arthritis," J. Exp. Med. 179(5):1517-1527 (1994).
Kwilasz et al, "The therapeutic potential of interleukin-10 in neuroimmune diseases," Neuropharmacology 96:55-69 (2015).
Latifi et al., "Interleukin-10 Controls the Onset of Irreversible Septic Shock," Infection and Immunity 70(8):4441-4446 (2002).
Steinhauser et al., "IL-10 is a Major Mediator of Sepsis-Induced Impairment in Lung Antibacterial Host Defense," Journal of Immunoloy 162(1):392-399 (1999).
Alten et al., "Tocilizumab: A novel humanized anti-interleukin 6 (IL-6) receptor antibody for the treatment of patients with non-RA systemic, inflammatory rheumatic diseases," Annals of Medicine 45(4):357-363 (2013).
Benveniste et al., "Involvement of the Janus Kinase/Signal Transducer and Activator of Transcription Signaling Pathway in Multiple Sclerosis and the Animal Model of Experimental Autoimmune Encephalomyelitis," Journal of Interferon & Cytokine Research 34(8):577-588 (2014).
Calich et al., "Osteoarthritis: can anti-cytokine therapy play a role in treatment?" Clin Rheumatol 29(5):451-455 (2010).
Clarke et al., "Single dose oral etoricoxib for acute postoperative pain in adults (Review)," Cochrane Database of Systemic Reviews, Cochrane Library, CD004309, 36 pages (2014).
Decision to refuse the EP patent application dated Dec. 2, 2021 for European Patent Application No. 17796169.5 (18 pages).
Eisen, "Manifold beneficial effects of acetyl salicylic acid and nonsteroidal anti-inflammatory drugs on sepsis," Intensive Care Med 38:1249-1257 (2012).
Hermouet et al., "Pathogenesis of Myeloproliferative Neoplasms: Role and Mechanisms of Chronic Inflammation," Mediators of Inflammation, vol. 2015, Article ID 145293, 16 pages (2015).
Kalden, "Emerging role of anti-tumor necrosis factor therapy in rheumatic diseases," Arthritis Research, vol. 4(Suppl 2):S34-S40 (2002).
Kang et al., "Therapeutic uses of anti-interleukin-6 receptor antibody," International Immunology 27(1):21-29 (2014).
Maroon et al., "Natural anti-inflammatory agents for pain relief," Surgical Neurology International 1:80, 10 pages (2010).
Sinatra, "Role of COX-2 Inhibitors in the Evolution of Acute Pain Management," Journal of Pain and Symptom Management, 24(1S):S18-S27 (2002).
Extended European Search Report issued in European Application No. 17796169.5, mailed Oct. 17, 2019, 11 pages.
International Search Report issued in PCT/JP2017/017640, dated Aug. 6, 2017, 4 pages.
Jones et al., "Comparison of U2OS and Huh-7 cells for identifying host factors that affect hepatitis C virus RNA replication," Journal of General Virology, vol. 91, pp. 2238-2248 (2010).
Kanaoka et al., "SCR: Novel Human Suppressors of cdc2/cdc13 Mutants of *Schizosaccharomyces pombe* Harbour Motifs for RNA Binding Proteins," Nucleic Acids Research 22(13):2687-2693 (1994).

Masuda et al., "Arid5a Controls IL-6 mRNA Stability, Which Contributes to Elevation of IL-6 Level In Vivo," PNAS 110(23):9409-9414, epub doi: 10.1073/pnas.1307419110 (6 pages) (2013).
Tanaka et al., "Interleukin-6; Pathogenesis and Treatment of Autoimmune Inflammatory Diseases," Inflammation and Regeneration 33(1):54-65 (2013).
Zhao et al., "Tristetraprolin Regulates Interleukin-6 Expression Through p38 MAPK-Dependent Affinity Changes with mRNA 3' Untranslated Region," Journal of Interferon & Cytokine Research 31(8):629-637, 2011.
Becher et al., "Cytokine networks in neuroinflammation," Nature Reviews Immunology 17(1):49-59 (2017).
Cavaillon et al., "Cytokine Cascade in Sepsis," Scand J Infect Dis 35(9):535-544 (2003).
Communication issued in European Application No. 17796169.5, mailed Dec. 7, 2020, 8 pages.
Firestein et al., "Evolving concepts of rheumatoid arthritis," Nature 423:356-361 (2003).
Galli et al., "The development of allergic inflammation," Nature, Macmillan Journals LTD 454(7203):445-454 (2008).
Hreggvidsdottir et al., "Inflammatory pathways in spondyloarthritis," Molecular Immunology 57(1):28-37 (2014).
Mcinnes et al., "Cytokines in the pathogenesis of rheumatoid arthritis," Nature Reviews Immunology 7(6):429-442 (2007).
Nathan et al., "Nonresolving Inflammation," Cell 140:871-882 (2010).
Nathan, "Points of control in inflammation," Nature 420(6917):846-852 (2002).
Rizzi et al., "Spontaneous remission of 'methotrexate-associated lymphoproliferative disorders' after discontinuation of immunosuppressive treatment for autoimmune disease. Review of the literature," Med Oncol 26(1):1-9 (2008).
Van De Ven et al., "Causes and prevention of chronic postsurgical pain," Current Opinion in Critical Care 18(4):366-371 (2012).
Zhang et al., "Cytokines, Inflammation, and Pain," International Anesthesiology Clinics, 27-37 (2007).
English translation of Written Opinion issued in PCT/JP2017/017640, dated Aug. 8, 2017, 6 pages.
Mendez-Samperio et al., "Regulation of Interleukin-8 by Interleukin-10 and Transforming Growth Factor B in Human Monocytes Infected with *Mycobacterium bovis*," Clinical and Diagnostic Laboratory Immunology 9(4):802-807 (2002).
Office Action dated Jun. 30, 2022, issued in Korean Application No. 10-2018-7034876, with English translation, 8 pages.
Chang et al., "The IL-6/JAK/Stat3 Feed-Forward Loop Drives Tumorigenesis and Metastasis," Neoplasia 15(7):848-862 (2013).
Elinav et al., "Inflammation-induced cancer: crosstalk between tumours, immune cells and microorganisms, " Nat Rev Cancer 13(11):759-771 (2013).
Gao et al., "Mutations in the EGFR kinase domain mediate STAT3 activation via IL-6 production in human lung adenocarcinomas," J Clin Invest 117(12):3846-3856 (2007).
Grivennikov et al., "Autocrine IL-6 Signaling: A Key Event in Tumorigenesis?" Cancer Cell 13(1):7-9 (2008).
Hartman et al., "Growth of Triple-Negative Breast Cancer Cells Relies upon Coordinate Autocrine Expression of the Proinflammatory Cytokines IL-6 and IL-8," Cancer Res 73(11):3470-3480 (2013).
He et al., "Identification of Liver Cancer Progenitors Whose Malignant Progression Depends on Autocrine IL-6 Signaling," Cell 155(2):384-396 (2013).
Jayasena et al., "Rbms3 functions in craniofacial development by posttranscriptionally modulating TGF-β signaling," J. Cell Bio. 199(3):453-466 (2012).
Journal of Japan Society of Immunology & Allergology in Otolaryngology, 2016, vol. 34, No. 1, pp. 13-18.
Kulbe et al., "The Inflammatory Cycokine Tumor Necrosis Factor-α Generates an Autocrine Tumor-Promoting Network in Epithelial Ovarian Cancer Cells," Cancer Res 67(2):585-592 (2007).
Lecture abstracts of BMB2015, (Collaborative conference of the 38th annual conference of the Molecular Biology Society of Japan and the 88th conference of the Japanese Biochemical Society), 2015, p. 1P0844.

(56) References Cited

OTHER PUBLICATIONS

Lee et al., "Identification of Novel Alternatively Spliced Transcripts of RBMS3 in Skeletal Muscle with Correlations to Insulin Action in vivo," J. Exp. Biomed. Sci. 15:301-307 (2009).
Leppek et al., "An optimized streptavidin-binding RNA aptamer for purification of ribonucleoprotein complexes dentifies novel ARE-binding proteins," Nucleic Acids Research, 42 (2):1-15 (2014).
Niki, et al., "MSSP promotes ras/myc cooperative cell transforming activity by binding to c-Myc," Genes to Cells 5:127-141 (2000).
Penkov et al., "Cloning of a human gene closely related to the genes coding for the c-myc single-strand binding proteins," Gene 243:27-36 (2000).
Rodriguez-Barrueco et al., "Inhibition of the autocrine IL-6-JAK2-STAT3-calprotectin axis as targeted therapy for HR-/HER2+ breast cancers," Genes Dev 29(15):1631-1648 (2015).
Sansone et al., "IL-6 triggers malignant features in mammospheres from human ductal breast carcinoma and normal mammary gland," J Clin Invest 117(12):3988-4002 (2007).
Yeh et al., "Autocrine IL-6-induced Stat3 activation contributes to the pathogenesis of lung adenocarcinoma and malignant pleural effusion," Oncogene 25(31):4300-4309 (2006).
Yu et al., "RBMS1 Suppresses Colon Cancer Metastasis through Targeted Stabilization of Its mRNA Regulon," Cancer Discovery 10(9):1410-1423 (2020).
Zhang, et al., "Low expression of RBMS3 and SFRP1 are associated with poor prognosis in patients with gastric cancer," Am J Cancer Res 6(11):2679-2689 (2016).
Zhou et al., "Autocrine HBEGF expression promotes breast cancer intravasation, metastasis and macrophage-independent invasion in vivo," Oncogene 33(29)3784-3793 (2014).
File History of U.S. Appl. No. 16/762,227, filed May 7, 2020.
Flieger et al., "Influence of cytokines, monoclonal antibodies and chemotherapeutic drugs on epithelial cell adhesion molecule (EpCAM) and Lewis y antigen expression," Clin Exp Immunol. 123:9-14 (2001).
Monti et al., "The CC Chemokine MCP-1/CCL2 in Pancreatic Cancer Progression: Regulation of Expression and Potential Mechanisms of Antimalignant Activity," Cancer Research 63:7451-7461 (2003).
Valle Oseguera et al., "cmvIL-10 Stimulates the Invasive Potential of MDA-MB-231 Breast Cancer Cells," PLOS One 9(2):e88708, pp. 1-8 (2014).

\* cited by examiner

[Fig1A]
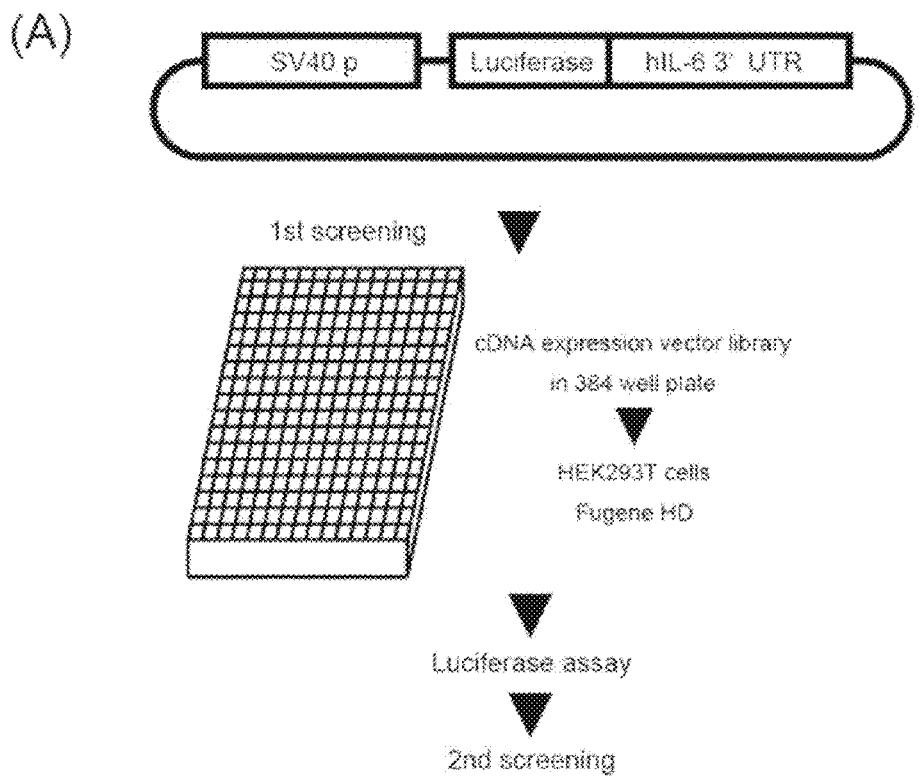
[Fig1B]
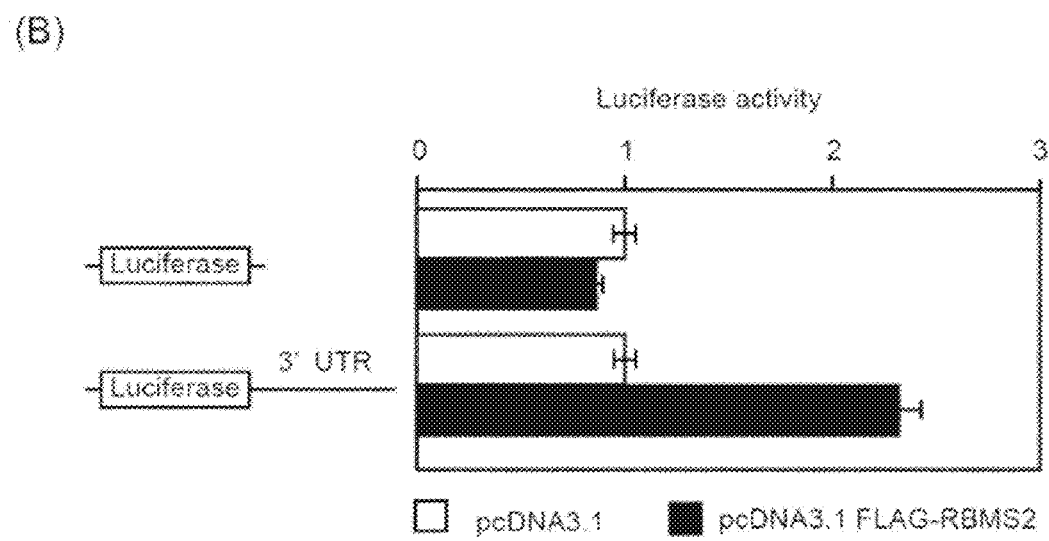

[Fig1C]
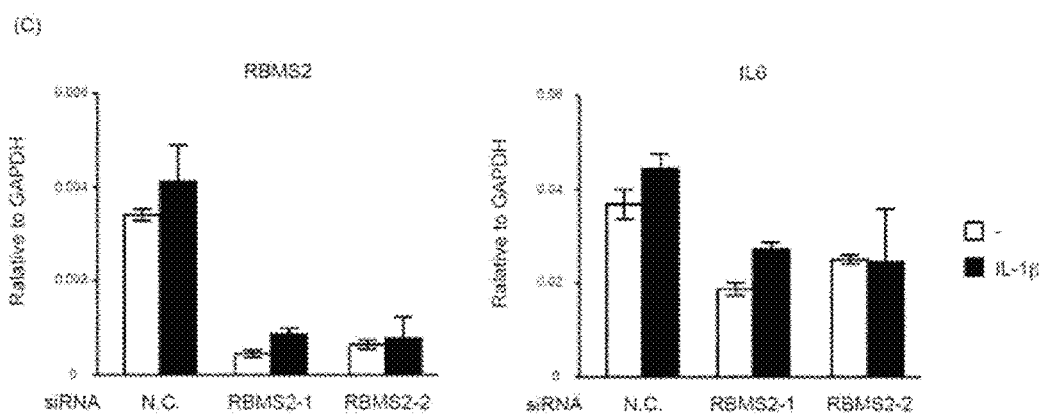
[Fig1D]
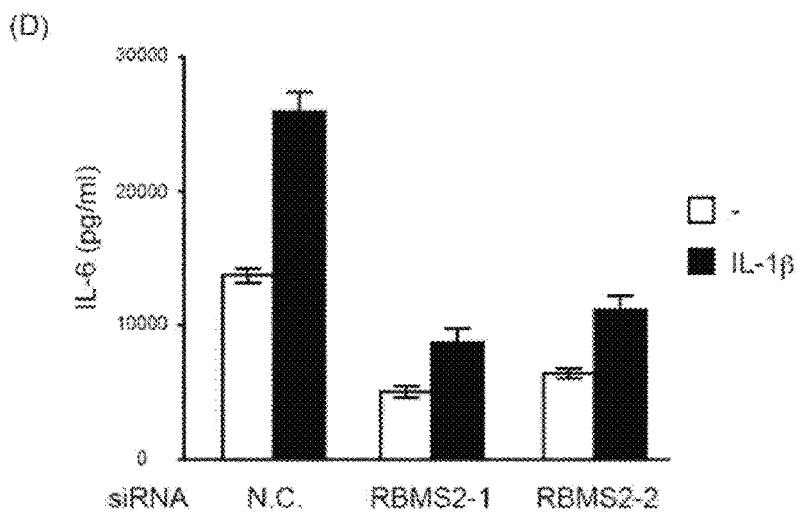

[Fig1E]
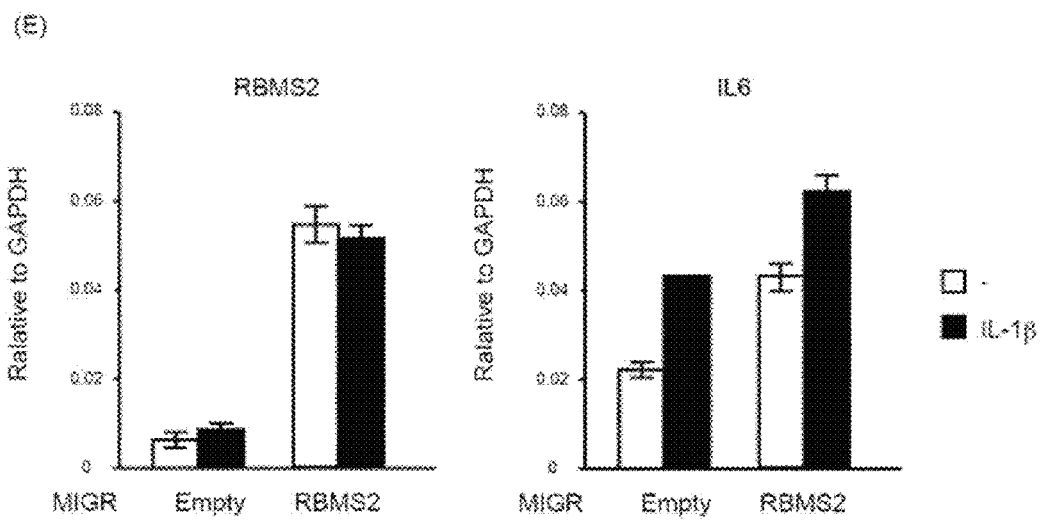
[Fig1F]
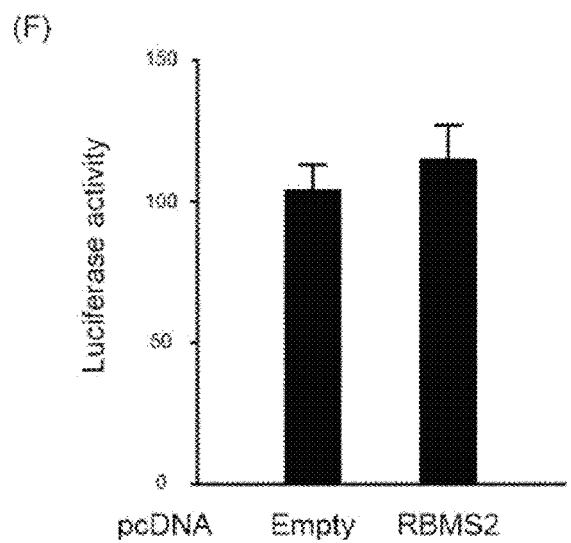

[Fig2A]
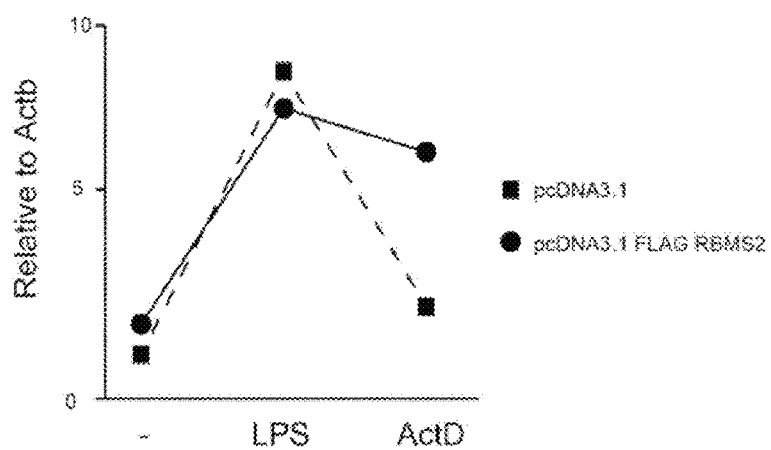
[Fig2B]
(B)
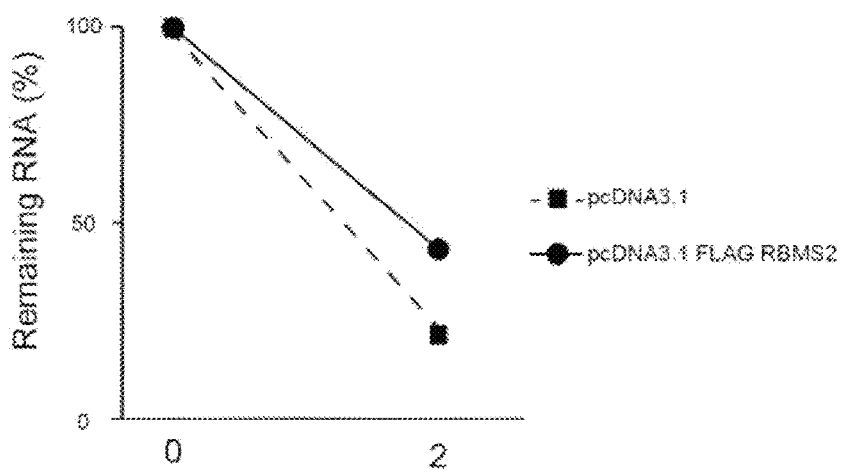

[Fig2C]
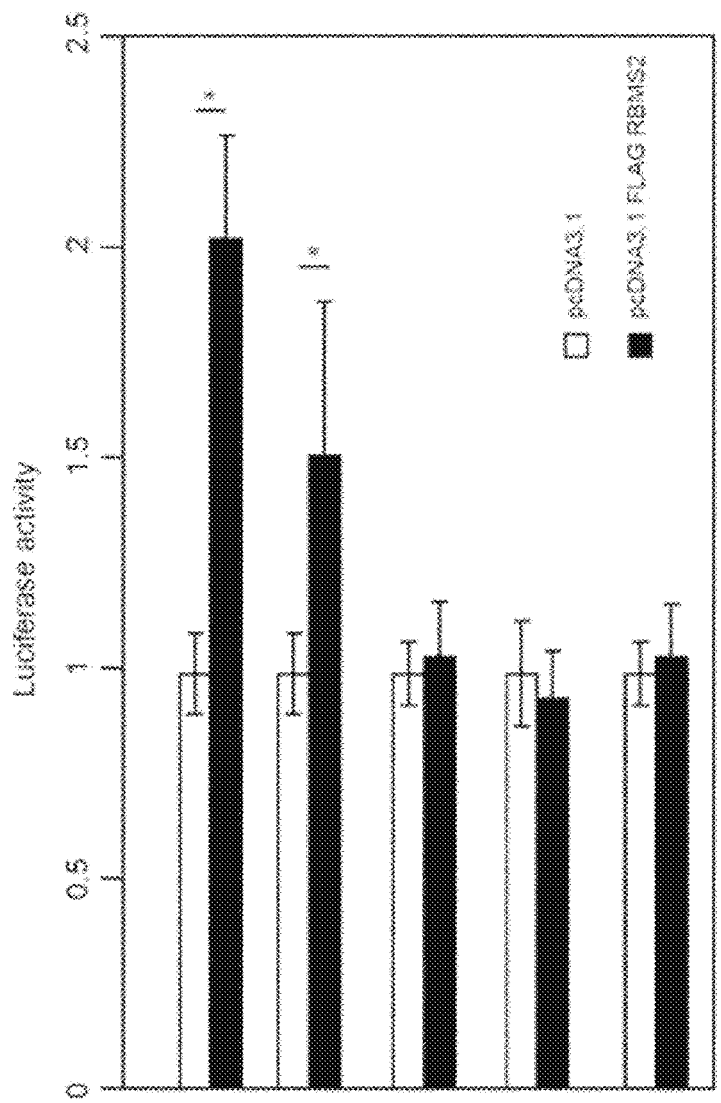

[Fig3A]
(A)
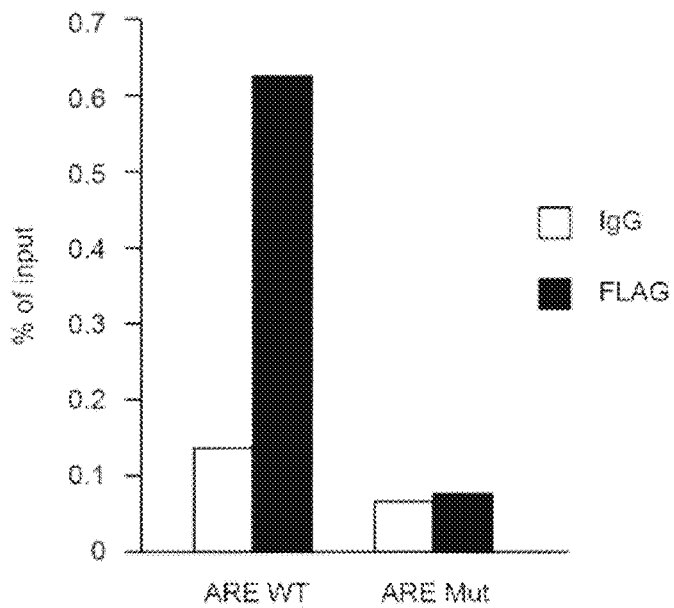
[Fig3B]
(B)
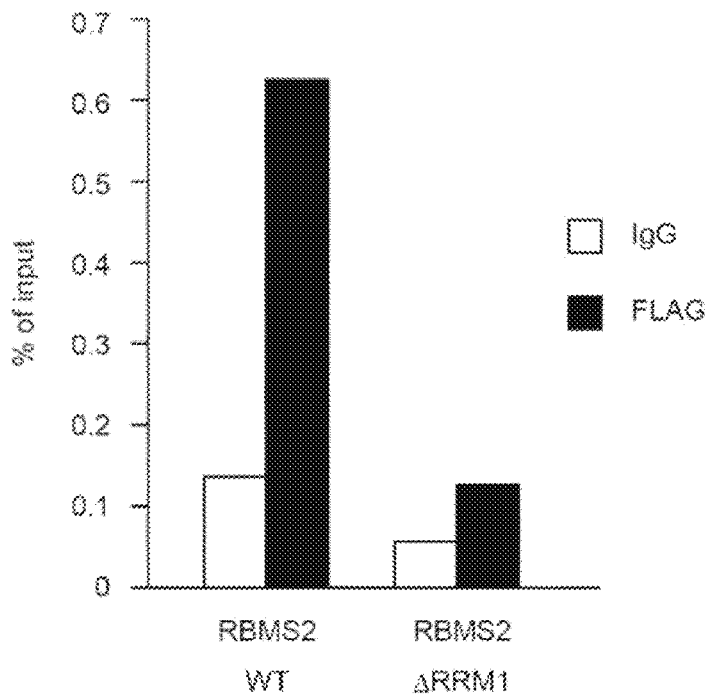

[Fig3C]
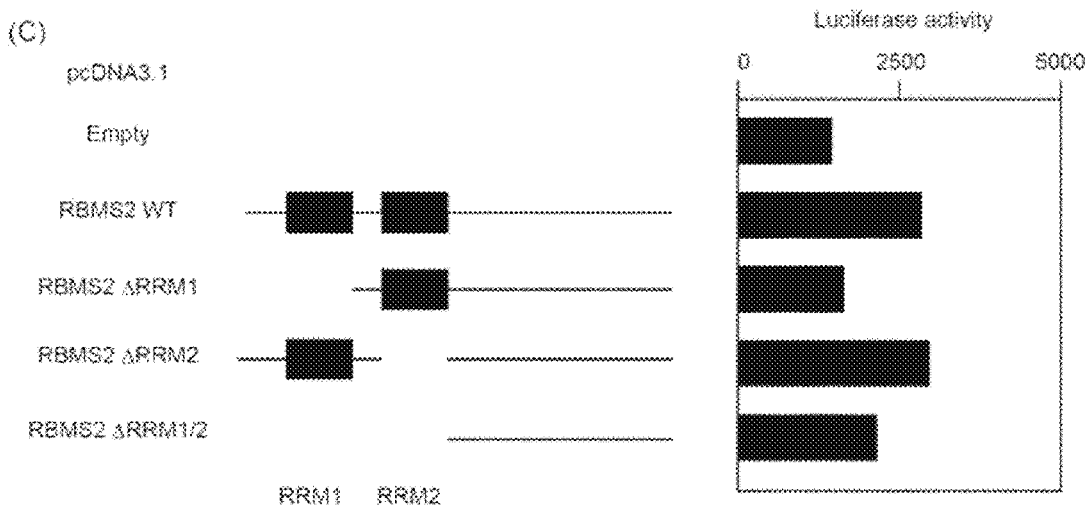

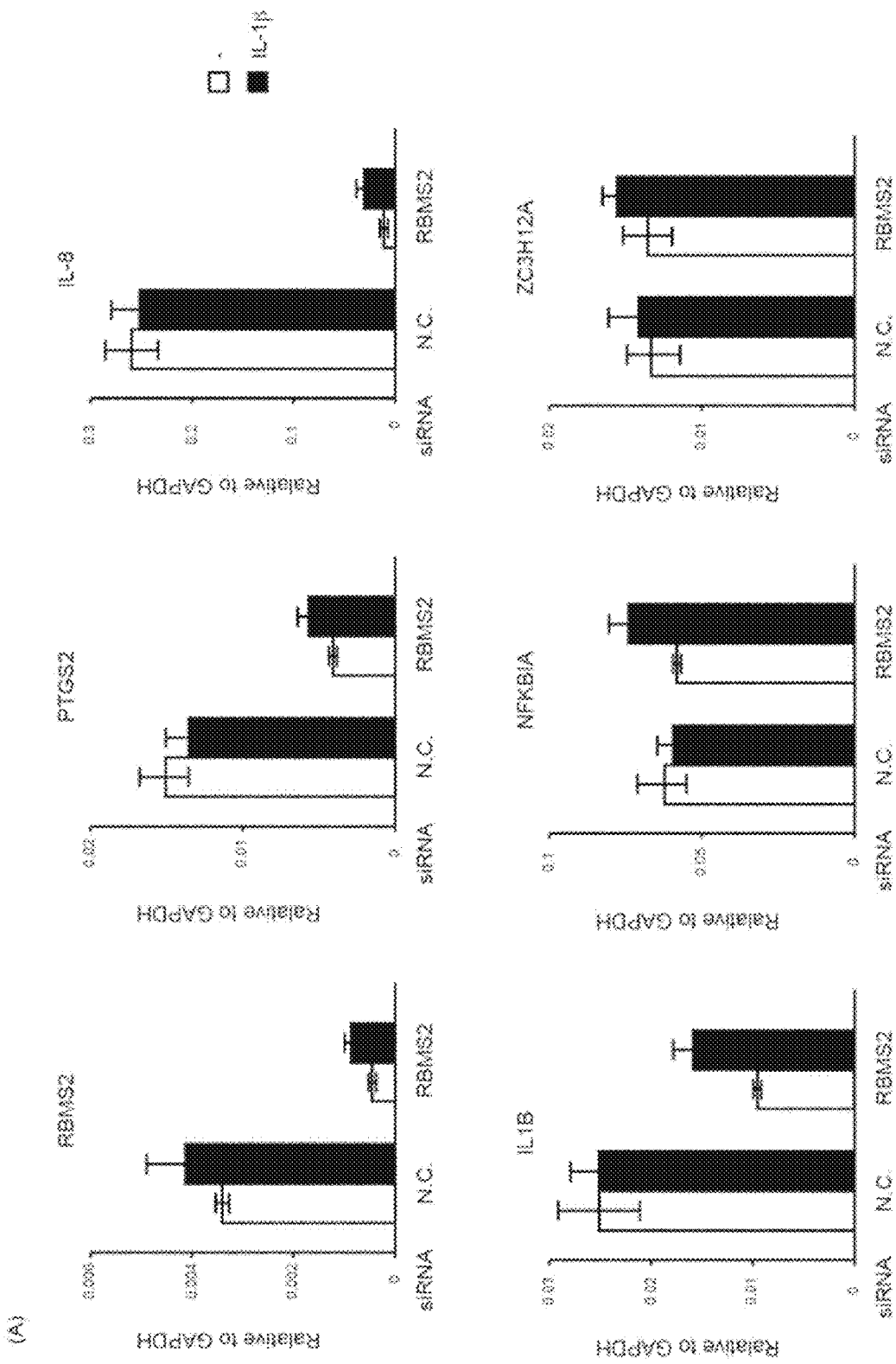
[Fig4A]

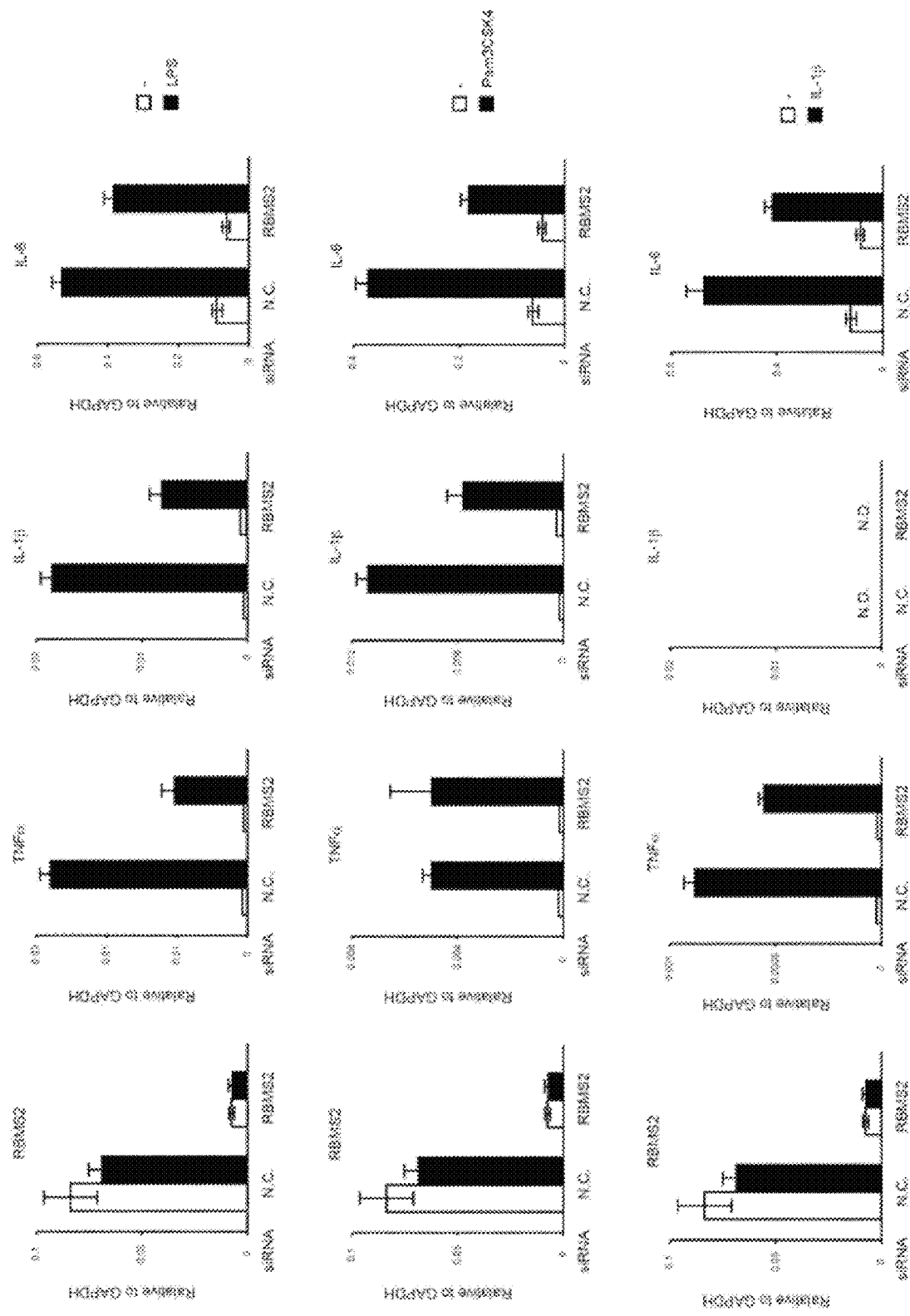
[Fig4B]

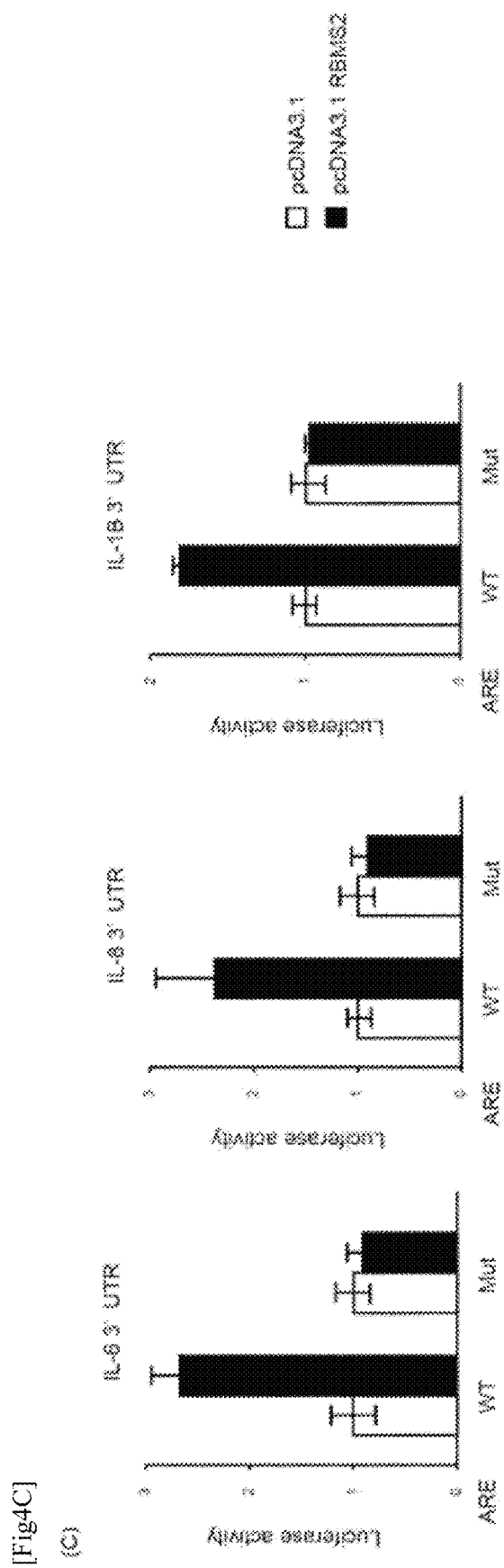
[Fig4C]

[Fig5A]
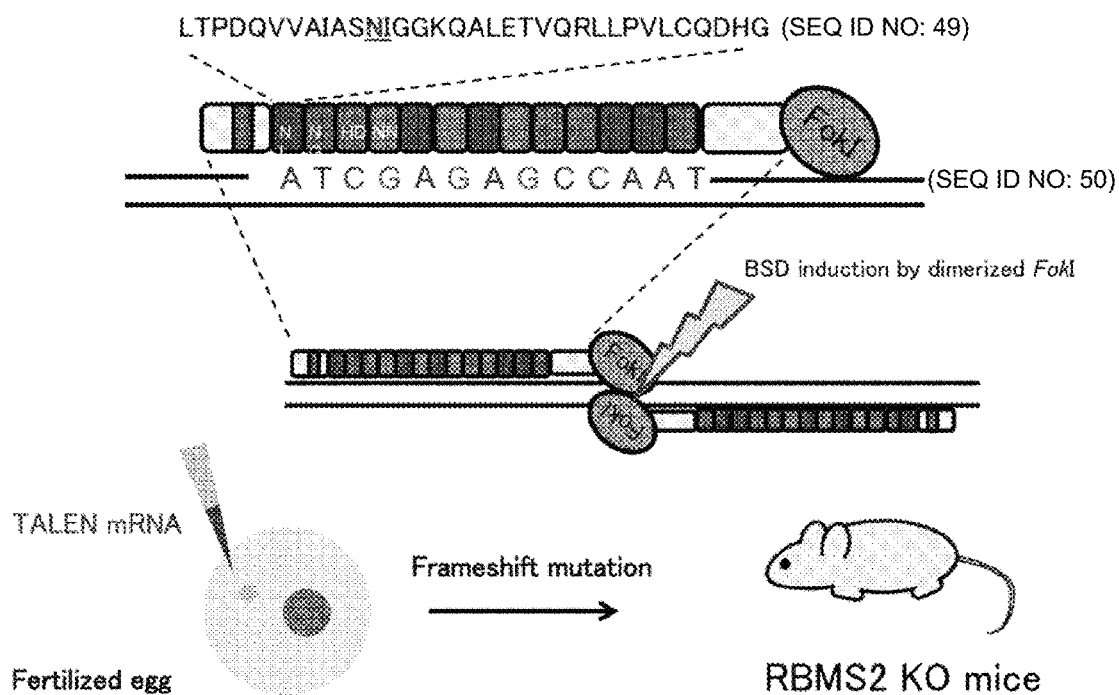

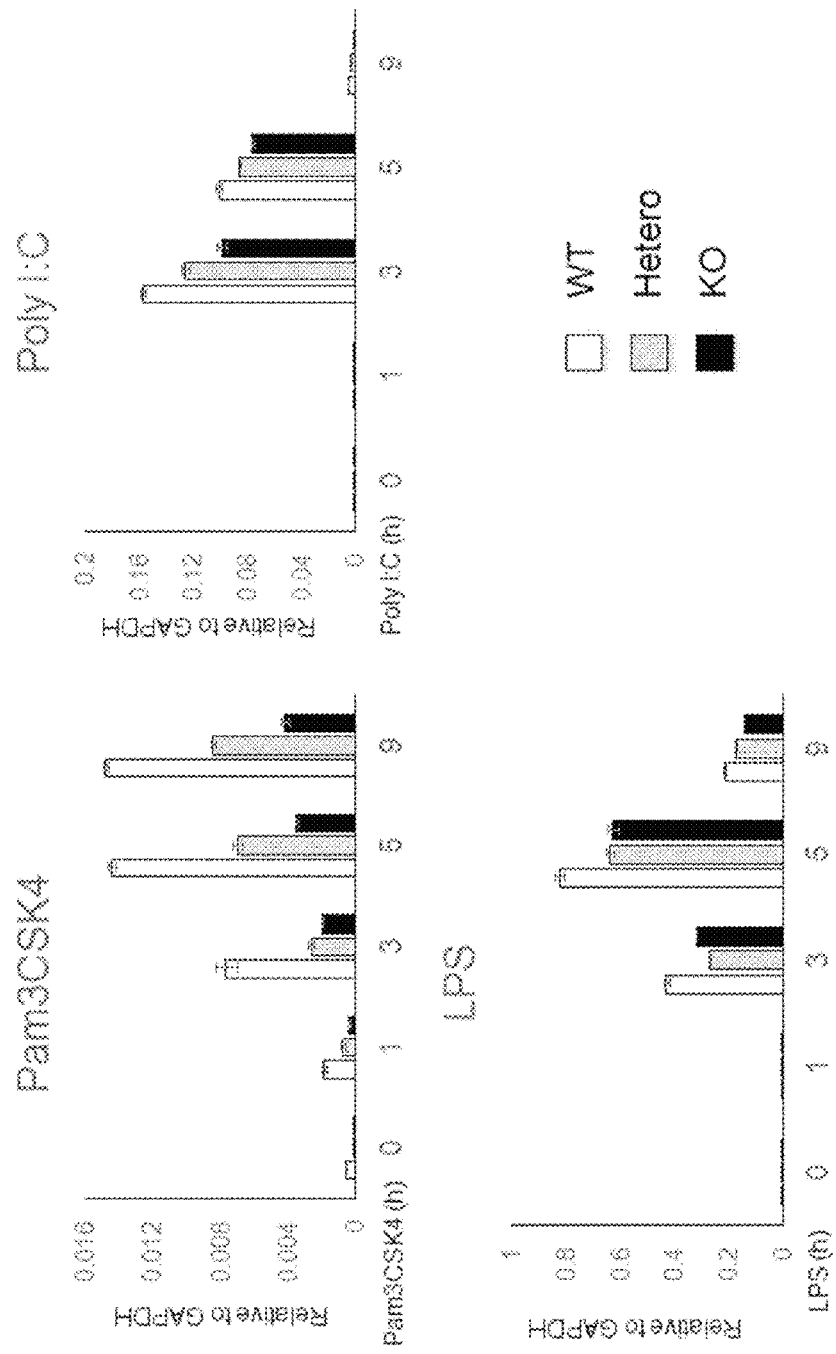
[Fig5B]

[Fig5C]
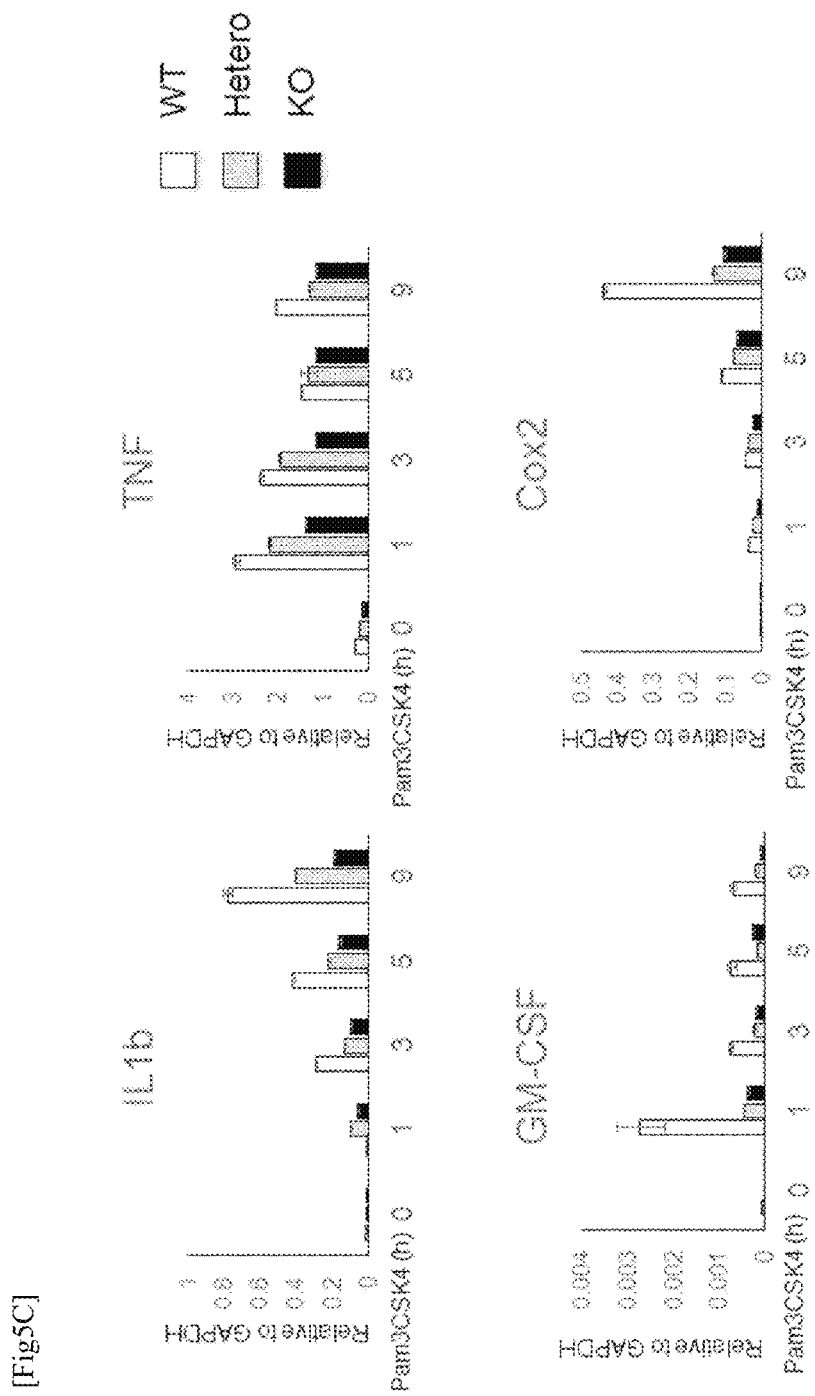

[Fig6A]
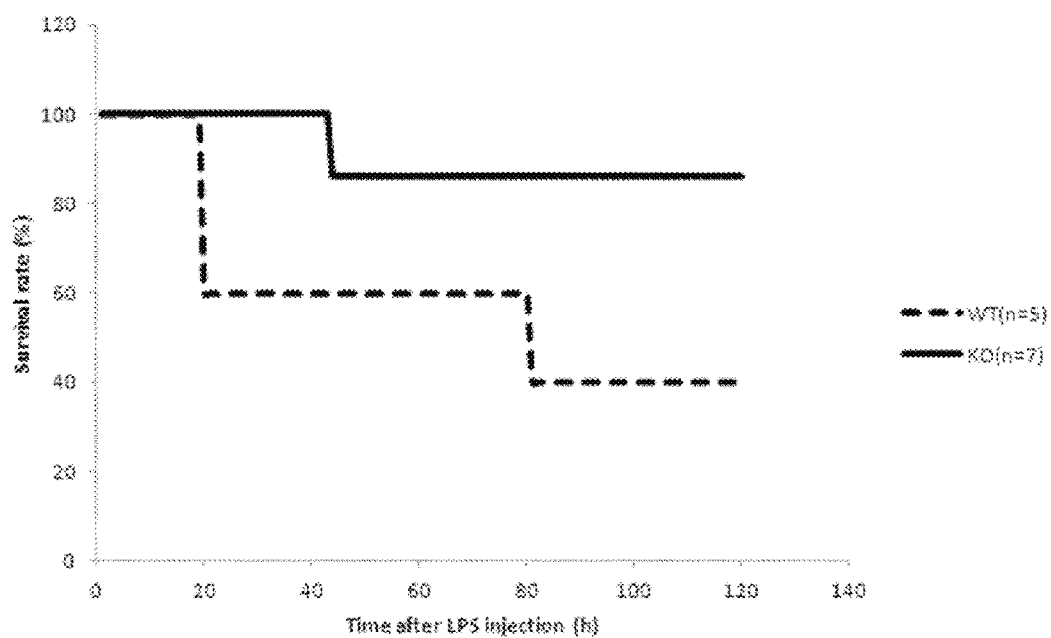
[Fig6B]
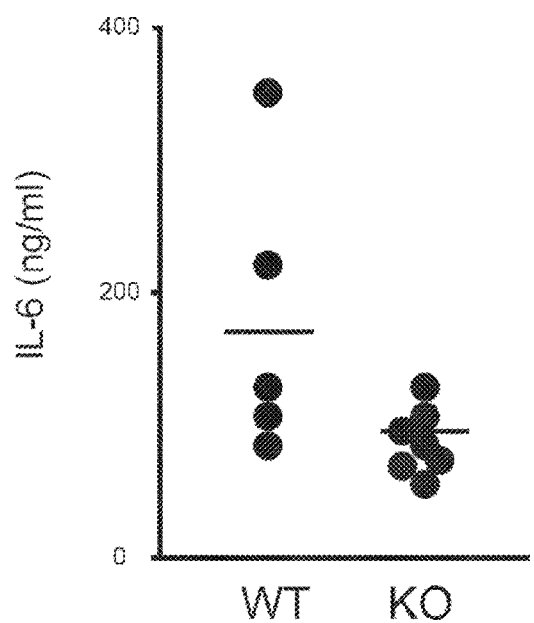

[Fig7]
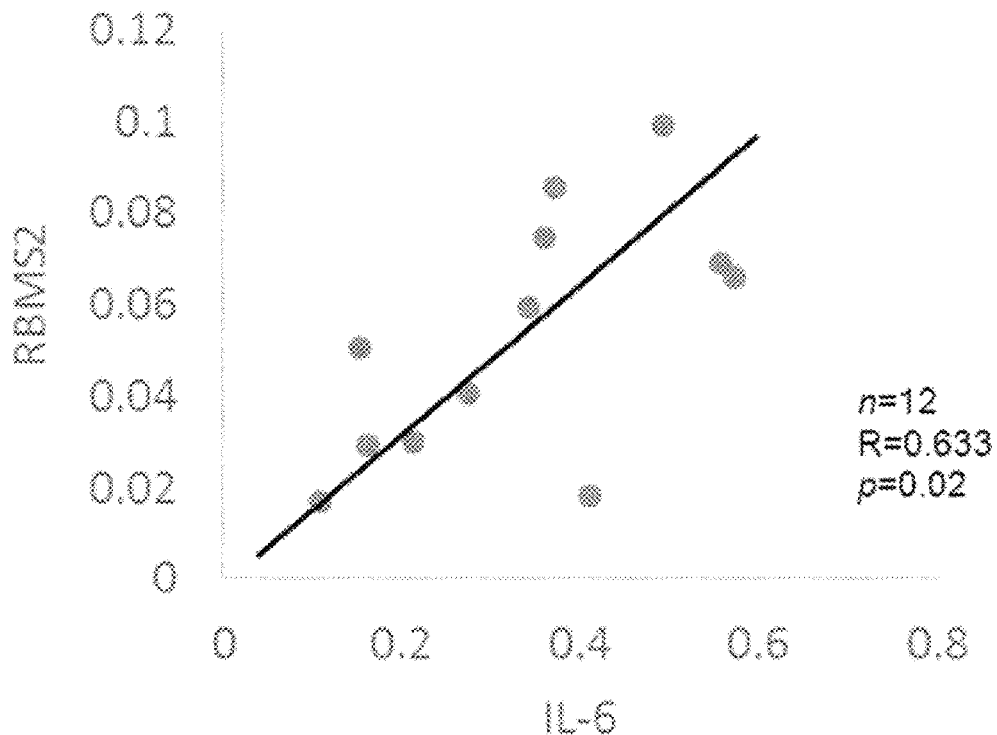
[Fig8]
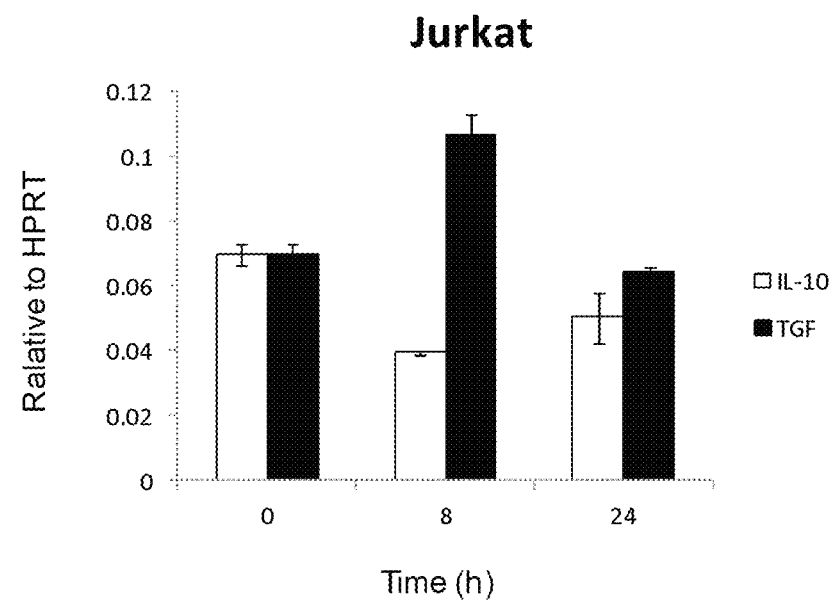

[Fig9]
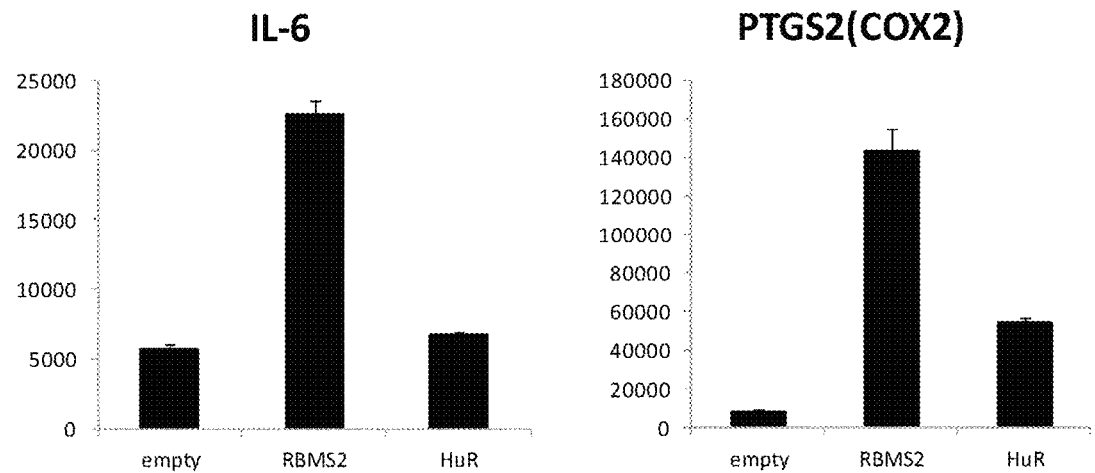
[Fig10A]
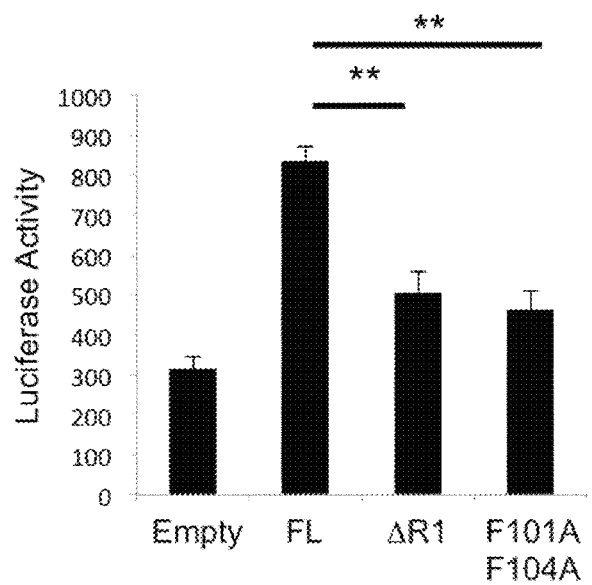

[Fig10B]
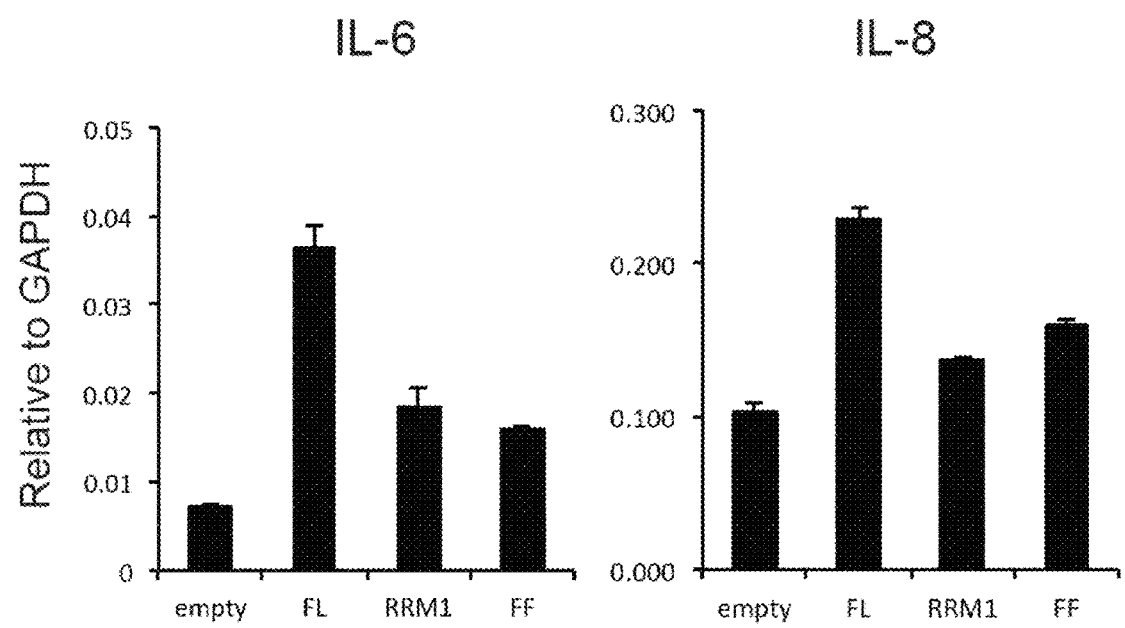

[Fig10C]
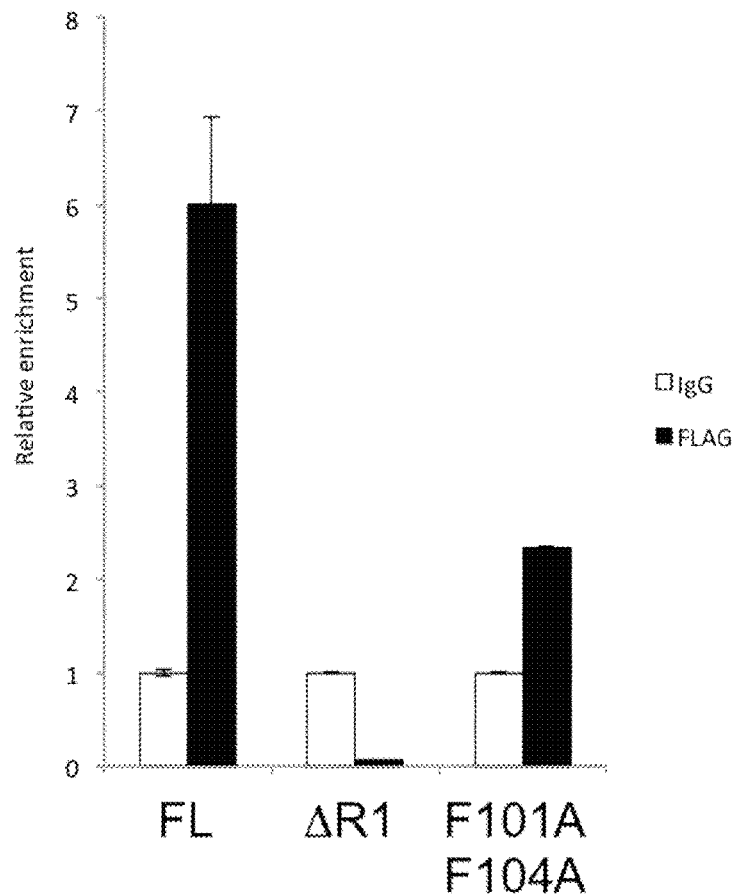
[Fig11]
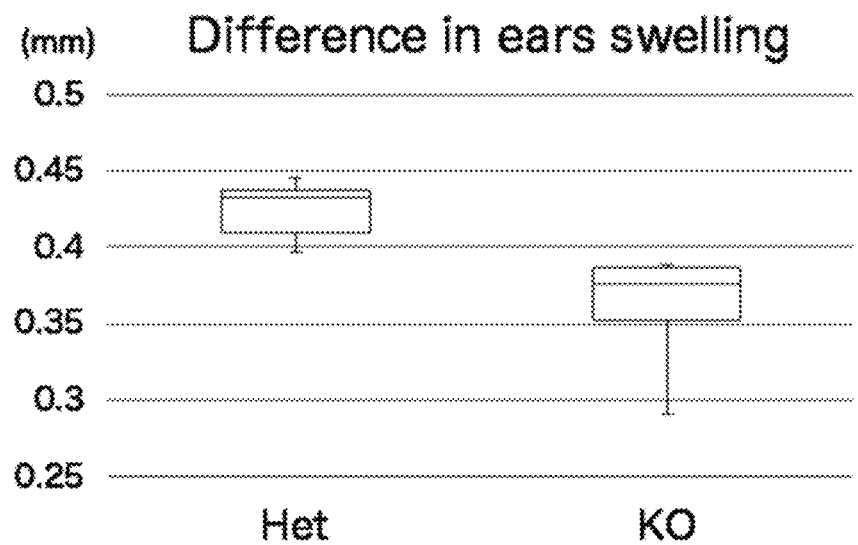

[Fig12]
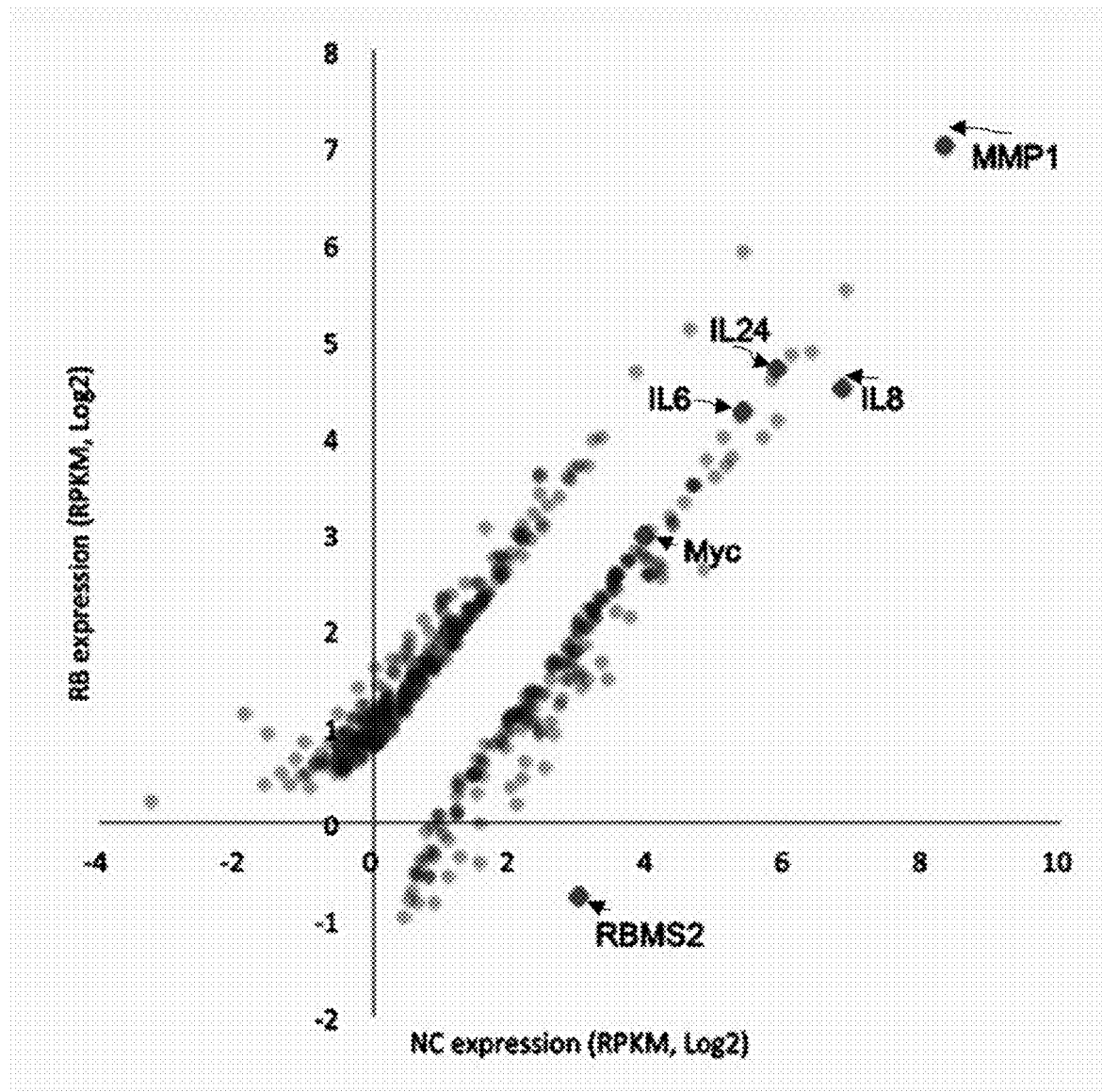

US 12,066,429 B2

METHOD FOR INHIBITING THE EXPRESSION OF INFLAMMATION PROMOTING FACTORS

CROSS-REFERENCE TO RELATED APPLICATIONS

This application is a divisional of U.S. application Ser. No. 16/300,442, filed Nov. 9, 2018, which is a national phase entry pursuant to 35 U.S.C. § 371 of International Application No. PCT/JP2017/017640, filed May 10, 2017, which claims the benefit of priority of JP Application Nos. 2016-094931, filed May 10, 2016, and 2016-162120, filed Aug. 22, 2016, each of which is incorporated by reference herein in its entirety for any purpose.

SEQUENCE LISTING

The present application is filed with a Sequence Listing in electronic format. The Sequence Listing is provided as a file entitled "2018-11-09_01178-0003-00US_Seq_List_ST25 txt" created on Nov. 9, 2018, which is 56,062 bytes in size. The information in the electronic format of the sequence listing is incorporated herein by reference in its entirety.

TECHNICAL FIELD

The present invention relates to an inhibitor of the expression of an inflammation promoting factor; a method for screening for an active ingredient of the inhibitor; an expression cassette useful for the method; a diagnostic agent and a diagnosis method both for immune diseases, inflammatory diseases, painful diseases and the like; and others.

BACKGROUND ART

There are great many patients who are suffering from diseases of which the symptoms can be developed or worsened by an inflammation promoting factor (e.g., IL-6 and COX-2), such as an immune disease, an inflammatory disease and a painful disease. For example, with respect to rheumatoid arthritis which is a major immune disease, it is estimated that there are about 700,000 patients in Japan and there are about 70,000,000 patients worldwide. With respect to arthrosis which is one of inflammatory diseases, it is estimated that there are about 15,600,000 patients even in Japan. With respect to osteoarthritis of the knee which is considered to be major arthrosis, it is estimated that there are about 10,000,000 patients in Japan. With respect to low back pain which is a major painful disease, it is estimated that there are about 24,000,000 patients even in Japan. The number of patients of these diseases tends to increase year by year as the population ages. It is believed that this phenomenon would be caused in Japan where the population aging rate is highest in the world, as well as in all of countries where the population aging would advance in the future due to the improvement in living environments, dietary habits and nutrition conditions, the advance in medical technologies and the like. By detecting these diseases in earlier stages, it becomes possible to start a proper treatment, prevent the increase in severity of the diseases and, as a result, keep the QOL of patients at higher levels. Therefore, it has been a socially important demand to study about therapeutic agents for the diseases and tools for developing the therapeutic agents and to develop diagnostic agents and diagnosis methods for the diseases.

In these situations, the relationship between the post-transcriptional regulation of inflammation promoting factor mRNA and the above-mentioned diseases has been obvious recently. It is suggested that the regulation of the degradation of mRNA for an inflammation promoting factor can be a factor that can determine the sustainability of an inflammatory response. Therefore, it is believed that a factor associated with the degradation or stabilization of an inflammation promoting factor at mRNA level is involved in the onset or chronicity of an immune disease, an inflammatory disease and a painful disease. For example, Non-Patent Document 1 discloses that Tristetraprolin (TTP) and Regnase-1 are involved in the degradation of IL-6 mRNA. Non-Patent Document 2 discloses that Arid5a can regulate the stability of IL-6 mRNA. It has been elucidated that the abnormalities of these factors play an important role in the mechanism of onset or worsening of the diseases, including the acceleration of inflammations. For these reasons, a factor that affects the expression amount/level of an inflammation promoting factor can become a target of therapeutic agents for the diseases, and a novel discovery about the factor has been demanded. On the other hand, a diagnostic agent and a diagnosis method whereby it becomes possible to diagnose as to the presence or absence of the above-mentioned diseases or the degree of progression of the diseases by measuring the amount/level of a substance capable of affecting the expression amount/level of an inflammation promoting factor in a cell, blood or the like from a patient are very useful. Therefore, a novel discovery about the factor has been demanded.

RNA-binding motif, single-stranded-interacting protein 2 (RBMS2) is a protein that is believed to have two RNA-binding domains on the N-terminal side. However, it is not reported yet that the functions of the protein are actually analyzed, and the functions of the protein are not elucidated yet.

PRIOR ART DOCUMENTS

Non-Patent Documents

Non-Patent Document 1: Inflammation and Regeneration, Vol. 33, No. 1, January 2013, pp 54-65.
Non-Patent Document 2: PNAS, Jun. 4, 2013, vol. 110, no. 23, pp 9409-9414

SUMMARY OF THE INVENTION

Problem to be Solved by the Invention

The present invention addresses the problem of: discovering a novel factor that can affect the expression amount/level of an inflammation promoting factor; providing an inhibitor of the expression of an inflammation promoting factor and a tool for developing the inhibitor on the basis of the discovering the factor; and providing a diagnostic agent and a diagnosis method both for immune diseases, inflammatory diseases, painful diseases and other diseases.

Means for Solving the Problems

The present inventors have made extensive and intensive studies for the purpose of solving the problem. As a result, it is found that RBMS2 is involved in the post-transcriptional regulation of mRNA molecules of various inflammation promoting factors. It is also found that there is a positive correlation between the expression of RBMS2 and the expression of an inflammation promoting factor in diseases which can be developed or worsened by an inflammation promoting factor. On the basis of these findings, it is also found that an inflammation promoting factor can be inhibited and the above-mentioned diseases can be prevented or treated by inhibiting the expression or function of RBMS2, and that these diseases can be diagnosed by employing the expression amount/level of RBMS2 as an index. The studies are further pursued on the basis of these findings. As a result, the present invention has been accomplished. That is, the present invention includes the following aspects.

1. An expression cassette containing a RBMS2 gene expression regulation region and a gene arranged in such a manner that the expression thereof can be regulated by the region.

2. The expression cassette according to item 1, wherein the gene is a reporter gene.

3. A vector carrying an expression cassette as recited in item 1 or 2.

4. A cell harboring a vector as recited in item 3.

5. A reagent for screening for an active ingredient for an inhibitor of the expression of an inflammation promoting factor, containing at least one component selected from the group consisting of an expression cassette containing a RBMS2 gene expression regulation region and a gene arranged in such a manner that the expression thereof can be regulated by the region, a vector carrying the expression cassette and a cell harboring the vector.

6. A method for screening for a substance capable of inhibiting the expression or function of RBMS2 by employing at least one item selected from the group consisting of items (i) to (iii) as an index in the presence of a test substance:

(i) the expression amount/level of a gene of which the expression can be regulated by a RBMS2 gene expression regulation region;

(ii) the binding amount/level of RBMS2 to RNA containing an AU-rich element; and (iii) the amount/level of mRNA containing an AU-rich element in a 3'-UTR thereof or the amount/level of a protein derived from the mRNA in a RBMS2-overexpressing cell.

7. The screening method according to item 6, wherein, when the value of the index in the presence of a test substance is smaller than the value of the index in the absence of the test substance, the test substance is selected as a substance capable of inhibiting the expression or function of RBMS2.

8. The screening method according to item 6 or 7, wherein the AU-rich element is an AU-rich element derived from at least one member of mRNA selected from the group consisting of IL-6 mRNA, COX-2 mRNA, IL-8 mRNA, IL-1β mRNA, TNF-α mRNA, MMP1 mRNA, IL-24 mRNA and c-Myc mRNA.

9. The screening method according to any one of items 6 to 8, wherein a substance capable of inhibiting the expression or function of RBMS2 is selected as an active ingredient for an inhibitor of the expression of an inflammation promoting factor or a candidate for the active ingredient.

10. The screening method according to any one of items 6 to 9, wherein the method includes steps (a1) to (c1):

(a1) bringing an expression system which contains an expression cassette containing a RBMS2 gene expression regulation region and a gene arranged in such a manner that the expression thereof can be regulated by the region into contact with a test substance;

(b1) measuring, as an expression amount/level of interest, the amount/level of the gene expressed in the expression system that has been contacted with the test substance and then comparing the expression amount/level of interest with a control expression amount/level that is the expression amount/level of the gene in an expression system that has not been contacted with the test substance; and (c1) selecting the test substance as a substance capable of inhibiting the expression of RBMS2 when the expression amount/level of interest is smaller than the control expression amount/level.

11. The screening method according to item 10, wherein the expression system is a cell.

12. The screening method according to item 10 or 11, wherein the gene is a reporter gene.

13. The screening method according to any one of items 6 to 9, wherein the method includes steps (a2) to (c2):

(a2) bringing RNA containing an AU-rich element into contact with RBMS2 in the presence of a test substance;

(b2) measuring the binding amount/level between the RNA and the RBMS2 which are contacted with each other in the presence of a test substance as a binding amount/level of interest, and then comparing the binding amount/level of interest with a control binding amount/level that is the binding amount/level between the RNA and the RBMS2 which are contacted with each other in the absence of the test substance; and (c2) selecting the test substance as a substance capable of inhibiting the function of RBMS2 when the binding amount/level of interest is smaller than the control binding amount/level.

14. The screening method according to item 13, wherein the method for measuring the binding amount/level is an immunoprecipitation method or a gel shift method.

15. The screening method according to any one of items 6 to 9, wherein the method includes steps (a3) to (c3):

(a3) bringing a cell which contains mRNA containing an AU-rich element in a 3'-UTR thereof and in which RBMS2 is overexpressed into contact with a test substance;

(b3) measuring the amount/level of the mRNA or a protein derived from the mRNA in the cell that has been contacted with the test substance as an amount/level of interest, and then comparing the amount/level of interest with a control amount/level that is the amount/level of the mRNA or a protein derived from the mRNA in a cell that is not contacted with the test substance; and (c3) selecting the test substance as a substance capable of inhibiting the function of RBMS2 when the amount/level of interest is smaller than the control amount/level.

16. The screening method according to item 15, wherein the mRNA contains an ORF of a reporter protein.

17. An inhibitor of the expression of an inflammation promoting factor containing at least one component selected from the group consisting of a RBMS2 expression inhibitor and a RBMS2 function inhibitor.

18. The inhibitor of the expression of an inflammation promoting factor according to item 17, wherein the inhibitor contains a RBMS2 expression inhibitor.

19. The inhibitor of the expression of an inflammation promoting factor according to item 18, wherein the RBMS2 expression inhibitor contains at least one RBMS2 expression inhibitor selected from the group consisting of RBMS2-specific siRNA, RBMS2-specific miRNA, a RBMS2-specific antisense nucleic acid and expression vectors for these components.

20. The inhibitor of the expression of an inflammation promoting factor according to item 18, wherein the RBMS2 expression inhibitor is IL-10.

21. The inhibitor of the expression of an inflammation promoting factor according to any one of items 17 to 20, wherein the inflammation promoting factor of which the expression is to be inhibited is at least one component selected from the group consisting of IL-6, COX-2, IL-8, IL-1β, TNF-α, MMP1, IL-24 and c-Myc.

22. The inhibitor of the expression of an inflammation promoting factor according to any one of items 17 to 21, wherein the inhibitor is used as a prophylactic or therapeutic agent for at least one disease selected from the group consisting of immune diseases, inflammatory diseases and painful diseases.

23. The inhibitor of the expression of an inflammation promoting factor according to any one of items 17 to 22, wherein the inhibitor is used as a prophylactic or therapeutic agent for at least one disease selected from the group consisting of autoimmune diseases, rheumatic diseases, rheumatoid arthritis, degenerative arthritis disease, arthritis, sepsis, lymphoproliferative diseases, demyelinating diseases in the central nervous system, spondyloarthropathy, inflammatory pain, postoperative pain and allergic diseases.

24. A diagnostic agent for a disease which can be developed or worsened by an inflammation promoting factor, which contains a RBMS2 gene expression product detecting agent.

25. The diagnostic agent according to item 24, wherein the disease is a disease which can be developed or worsened by an inflammation promoting factor.

26. The diagnostic agent according to item 24 or 25, wherein the disease is at least one disease selected from the group consisting of immune diseases, inflammatory diseases and painful diseases.

27. The diagnostic agent according to item 25 or 26, wherein the inflammation promoting factor is at least one component selected from the group consisting of IL-6, COX-2, IL-1β, IL-8, TNF-α, MMP1, IL-24 and c-Myc.

28. The diagnostic agent according to any one of items 24 to 27, wherein the RBMS2 gene expression product detecting agent is a probe or a primer for RBMS2 mRNA or a nucleic acid derived from the RBMS2 mRNA or an antibody capable of recognizing RBMS2 protein.

29. The diagnostic agent according to any one of items 24 to 28, wherein the disease that is a disease to be diagnosed is at least one disease selected from the group consisting of autoimmune diseases, rheumatic disease, rheumatoid arthritis, degenerative arthritis diseases, arthritis, sepsis, lymphoproliferative diseases, demyelinating diseases in the central nervous system, spondyloarthropathy, inflammatory pain, postoperative pain and allergic diseases.

30. The diagnostic agent according to item 29, wherein the disease that is a disease to be diagnosed is rheumatoid arthritis.

31. The diagnostic agent according to any one of items 24 to 30, wherein the item to be diagnosed is the presence or absence of the disease.

32. The diagnostic agent according to any one of items 24 to 30, wherein the item to be diagnosed is the degree of progression of the disease.

33. A method for detecting an immune disease, an inflammatory disease or a painful disease, comprising the steps of:
(a1) measuring the expression amount/level of interest of a RBMS2 gene expression product in a sample collected from a subject; and
(b1) comparing the expression amount/level of interest measured in step (a1) with a control expression amount/level of the RBMS2 gene expression product in a sample collected from a control subject which does not suffer from any one of the immune disease, the inflammatory disease and the painful disease,
wherein
(c1) the matter that the expression amount/level of interest is larger than the control expression amount/level is employed as an index for the determination that the subject has the immune disease, the inflammatory disease or the painful disease.

34. A method for determining the degree of progression of an immune disease, an inflammatory disease or a painful disease, comprising the steps of:
(a2) measuring the expression amount/level of interest of a RBMS2 gene expression product in a sample collected from a subject suffering from the immune disease, the inflammatory disease or the painful disease; and
(b2) comparing the expression amount/level of interest measured in step (a2) with a control expression amount/level of a RBMS2 gene expression product in a sample collected from a control subject suffering from the immune disease, the inflammatory disease or the painful disease,
wherein
(c3) the matter that the expression amount/level of interest is larger than the control expression amount/level is employed as an index for the determination that the subject has a higher degree of progression of the immune disease, the inflammatory disease or the painful disease than that of the control subject.

35. The method according to item 33 or 34, wherein the sample to be used in each of step (a1) and step (a2) is a blood sample.

36. The method according to any one of items 33 to 35, wherein the sample to be used in each of step (a1) and step (a2) is a blood cell component in a blood sample.

37. The method according to any one of items 33 to 36, wherein the immune disease, the inflammatory disease and the painful disease can be developed or can be worsened by at least one component selected from the group consisting of IL-6, COX-2, IL-1β, IL-8, TNF-α, MMP1, IL-24 and c-Myc.

38. The method according to any one of items 33 to 37, wherein the expression amount/level of interest of the RBMS2 gene expression product and the control expression amount/level are measured using a probe or primer directed against RBMS2 mRNA or a nucleic acid derived from the RBMS2 mRNA or an antibody capable of recognizing RBMS2 protein.

Advantages of the Invention

According to the present invention, it becomes possible to provide a novel inhibitor of the expression of an inflammation promoting factor, a novel prophylactic or therapeutic agent for an immune disease, an inflammatory disease, a painful disease or the like, and a tool for developing the inhibitor or the prophylactic or therapeutic agent (e.g., a method for screening for an active ingredient, an expression cassette useful for the method), all of which utilize a novel target factor that affects the expression amount/level of an inflammation promoting factor. According to the present invention, it also becomes possible to provide a diagnostic agent and a diagnosis method for an immune disease, an inflammatory disease, a painful disease or the like, which rely on a novel mechanism.

BRIEF DESCRIPTION OF DRAWINGS

FIG. 1A illustrates a schema of screening of Example 1A.

FIG. 1B illustrates the results of Example 1B. In the left side of the graph, an upper schematic diagram illustrates a partial structure of a control reporter vector (without an IL-6 3'UTR) used, and a lower schematic diagram illustrates a partial structure of a reporter vector (with an IL-6 3'UTR) used. A white column represents a case where an empty vector (pcDNA3.1) is introduced, and a black column represents a case where a RBMS2 expression vector (pcDNA3.1 FLAG-RBMS2) is introduced. The transverse axis represents a relative value of a measured luciferase activity.

FIG. 1C illustrates the results of Example 1C. The vertical axis on the left side in the drawings represents a relative value of the amount/level of RBMS2 mRNA relative to the amount/level of GAPDH mRNA, the vertical axis on the right side in the drawings represents a relative value of the amount/level of IL-6 mRNA relative to the amount/level of GAPDH mRNA. In the transverse axis, "N.C." represents a case where control siRNA is introduced, and "RBMS2-1" and "RBMS2-2" respectively represent cases where siRNA for different region of RBMS2 is introduced. A white column represents a case where IL-1β is not added, and a black column represents a case where IL-1β is added.

FIG. 1D illustrates the results of Example 1D. The vertical axis represents the concentration of IL-6 protein in a supernatant. In the transverse axis, "N.C." represents a case where control siRNA is introduced, and "RBMS2-1" and "RBMS2-2" respectively represent cases where siRNA for different region of RBMS2 is introduced. A white column represents a case where IL-1β is not added, and a black column represents a case where IL-1β is added.

FIG. 1E illustrates the results of Example 1E. The vertical axis on the left side of the drawings represents a relative value of a amount/level of RBMS2 mRNA relative to the amount/level of GAPDH mRNA, and the vertical axis on the right side of the drawings represents a relative value of a amount/level of IL-6 mRNA relative to a amount/level of GAPDH mRNA. In each of the transverse axes, "Empty" represents a case where a control retrovirus is allowed to infect, and "RBMS2" represents a case where a retrovirus capable of expressing RBMS2 is allowed to infect. A white column represents a case where IL-1β is not added, and a black column represents a case where IL-1β is added.

FIG. 1F illustrates the results of Example 1F. The vertical axis represents a relative value of a measured luciferase activity. In the transverse axes, "Empty" represents a case where an empty vector is introduced, and "RBMS2" represents a case where a RBMS2 expression vector is introduced.

FIG. 2A illustrates the results of Example 2A. The vertical axis represents a relative value of a amount/level of IL-6 mRNA relative to a amount/level of β-actin (Actb) mRNA. In the transverse axis, "−" represents a cell sample collected 48 hours after the introduction of an expression vector, "LPS" represents a cell sample collected 5 hours after the addition of LPS, and "ActD" represents a cell sample collected 3 hours after the addition of actinomycin D. The black column represents a case where an empty vector is introduced, "●" represents a case where a RBMS2 expression vector is introduced.

FIG. 2B illustrates the results of Example 2B. In the transverse axis, "0" represents a cell sample collected 24 hours after the introduction of a vector (during which doxycycline is not added yet), and "2" represents a cell sample collected 2 hours after the addition of doxycycline. The vertical axis represents a relative ratio of a amount/level of luciferase mRNA (when 0, the relative ratio is 100%). The black column represents a case where an empty vector is introduced, and "●" represents a case where a RBMS2 expression vector is introduced.

FIG. 2C illustrates the results of Example 2C. The schematic diagrams on the left side of the graph show the partial structures of a mutant 3'UTR reporter vector. The transverse axis represents a relative value of a luciferase activity. A white column represents a case where an empty vector is introduced, and a black column represents a case where a RBMS2 expression vector is introduced. "*" represents the fact that a p value was 0.05 or less as the result of a t-test.

FIG. 3A illustrates the results of Example 3A. The vertical axis represents a relative value of a amount/level of luciferase mRNA in an immunoprecipitation product, wherein the amount/level of luciferase mRNA in a cell lysate before immunoprecipitation is 100%. In the transverse axis, "ARE WT" represents a case where a reporter vector having, linked thereto, a wild-type 3'UTR of IL-6 downstream from a luciferase ORF (Example 1A), and "ARE Mut" represents a case where a mutant 3'UTR reporter vector (Example 2C: ARE mutant) is introduced. A black column represents a case where immunoprecipitation is performed with an anti-FLAG antibody, and a white column represents a case where immunoprecipitation is performed by a non-specific IgG.

FIG. 3B illustrates the results of Example 3B. The vertical axis represents a relative value of a amount/level of luciferase mRNA in an immunoprecipitation product, wherein the amount/level of luciferase mRNA in a cell lysate before immunoprecipitation is 100%. In the transverse axis, "PBMS2 WT" represents a case where an expression vector for FLAG-tagged wild-type RBMS2 is introduced, and "RBMS2 ΔRRM1" represents a case where an expression vector for FLAG-tagged RRM1 domain-deleted RBMS2 is introduced. A black column represents a case where immunoprecipitation is performed with an anti-FLAG antibody, and a white column represents a case where immunoprecipitation is performed by a non-specific IgG.

FIG. 3C illustrates the results of Example 3C. The schematic diagrams on the left side of the graph show the structures of RBMS2 which can be expressed with the used expression vectors. The transverse axis represents a relative value of a luciferase activity.

FIG. 4A illustrates the results of Example 4A. The vertical axis in each drawing represents a relative value of a amount/level of mRNA of each of genes indicated in upper parts of the drawings relative to a amount/level of GAPDH mRNA. In each of the transverse axes, "N.C." represents a case where control siRNA is introduced, and "RBMS2" represents a case where siRNA for RBMS2 is introduced. A white column represents a case where IL-1β is not added, and a black column represents a case where IL-1β is added.

FIG. 4B illustrates the results of Example 4B. The upper row represents cases where LPS is used, the middle row represents cases where Pam3CSK4 is used, and the lower row represents cases where IL-1β is used. The vertical axis in each drawing represents a relative value of a amount/level of mRNA of each of genes indicated in upper parts of the drawings relative to a amount/level of GAPDH mRNA. In each of the transverse axes, "N.C." represents a case where control siRNA is introduced, and "RBMS2" represents a case where siRNA for RBMS2 is introduced. A white column represents a case where no one of LPS, Pam3CSK4 and IL-1β is added, and a black column represents a case where LPS, Pam3CSK4 or IL-1β is added.

FIG. 4C illustrates the results of Example 4C. The vertical axis represents a relative value of a luciferase activity in the case where a reporter vector in which a wild-type 3'-UTR (or an ARE mutant 3'-UTR) of a gene indicated in the upper part of each drawing is located downstream from a luciferase ORF is used. In each of the transverse axes, "WT" represents a case where a wild-type 3'UTR is used, and "Mut" represents a case where an ARE mutant 3'UTR is used. A white column represents a case where an empty vector is introduced, and a black column represents a case where a RBMS2 expression vector is introduced.

FIG. 5A illustrates the scheme of the production of a RBMS2-deficient mouse in Example 5A.

FIG. 5B illustrates the results of Example 5B. The vertical axis in each drawing represents an expression amount/level of IL-6 when each of factors indicated in the upper parts of the drawings is added to a culture medium (a relative value relative to a amount/level of GAPDH mRNA). In each of the transverse axes, "0" represents the fact that the factor indicated in each of the upper parts of the drawings is not added, and each of "1", "3", "5" and "9" represents the time lapsed after the addition of the factor indicated in each of the upper parts of the drawings. A white column represents a case where a cell derived from a wild-type mouse is used, a gray column represents a case where a cell derived from a RBMS2 heterozygously deficient mouse is used, and a black column represents a case where a cell derived from a RBMS2 homozygously deficient mouse is used.

FIG. 5C illustrates the results of Example 5C. The vertical axis in each drawing represents an expression amount/level of mRNA for a gene indicated in each of the upper parts of the drawings (a relative value relative to a amount/level of GAPDH mRNA). In each of the transverse axes, "0" represents the fact that Pam3CSK4 is not added yet, and each of "1", "3", "5," and "9" represents a time lapsed after the addition of Pam3CSK4. A white column represents a case where a cell derived from a wild-type mouse is used, a gray column represents a case where a cell derived from a RBMS2 heterozygously deficient mouse is used, and a black column represents a case where a cell derived from a RBMS2 homozygously deficient mouse is used.

FIG. 6A illustrates the results of the measurement of survival times in Example 6. The vertical axis represents a survival rate, and the transverse axis represents a time lapsed after the administration of LPS. "WT" represents a survival rate of a wild-type mouse, and "KO" represents a survival rate of a RBMS2 homozygously deficient mouse.

FIG. 6B illustrates the results of the measurement of the concentration of IL-6 in Example 6. The vertical axis represents a concentration of IL-6 in serum. In the transverse axis, "WT" represents a wild-type mouse, and "KO" represents a RBMS2 homozygously deficient mouse. In the graph, each plot represents a concentration of IL-6 in serum from each individual, and each of the bars represents an average value.

FIG. 7 illustrates the results of Example 7. The vertical axis represents a relative value of an expression amount/level of RBMS2. The transverse axis represents a relative value of an expression amount/level of IL-6.

FIG. 8 illustrates the results of Example 8. The vertical axis represents a relative value of an expression amount/level of RBMS2 mRNA relative to an expression amount/level of HPRT mRNA. The transverse axis represents a time lapsed after the addition of IL-10 protein or TGFβ protein. A white column represents a case where IL-10 protein is added, and a black column represents a case where TGFI3 protein is added.

FIG. 9 illustrates the results of Example 9. The vertical axis on the left side of the drawings represents a luciferase activity obtained in the case where an IL-6 3'UTR is linked downstream from a luciferase ORF, and the vertical axis on the right side of the drawings represents a luciferase activity obtained in the case where a PTGS2(COX2) 3'UTR is linked downstream from a luciferase ORF. In each of the transverse axes, "Empty" represents a case where an empty vector is introduced, and "RBMS2" represents a case where a RBMS2 expression vector is introduced, and "HuR" represents a case where a HuR expression vector is introduced.

FIG. 10A illustrates the results of Example 10A. The vertical axis represents a relative value of a luciferase activity. In each of the transverse axes, "Empty" represents a case where an empty vector is introduced, "FL" represents a case where a wild-type RBMS2 expression vector is introduced, "dR1" represents a case where a RRM1 domain deficient expression vector is introduced, and "F101A F104A" represents a case where an expression vector in which F101A and F104A are double-mutated is introduced. "**" represents the fact that a P value<0.01.

FIG. 10B illustrates the results of Example 10B. The left drawing represents the results of the measurement of a amount/level of IL-6 mRNA, and the right drawing represents the results of the measurement of a amount/level of IL-8 mRNA. The vertical axis in each of the drawings represents a relative value of a amount/level of IL-6 mRNA or IL-8 mRNA relative to a amount/level of GAPDH mRNA. In each of the transverse axes, "empty" represents a case where a control lentivirus is allowed to infect, "FL" represents a case where a lentivirus capable of expressing wild-type RBMS2 is allowed to infect, "RRM1" represents a case where a lentivirus capable of expressing a RRM1 domain-deficient body is allowed to infect, and "FF" represents a case where a lentivirus capable of expressing a F101A/F104A double mutant is allowed to infect.

FIG. 10C illustrates the results of Example 10C. The vertical axis represents a relative value of a amount/level of luciferase mRNA in an immunoprecipitation product, wherein the amount/level of luciferase mRNA in a cell lysate before immunoprecipitation is 100%. In the transverse axis, "WT FL" represents a case where an expression vector for FLAG-tagged wild-type RBMS2 is introduced, "WT dR1" represents a case where an expression vector for FLAG-tagged RRM1 domain-deleted RBMS2 is introduced, and "WT F101/F104A" represents a case where an expression vector for a F101A/F104A double mutant is introduced. A black column represents a case where immunoprecipitation is performed with an anti-FLAG antibody, and a white column represents a case where immunoprecipitation is performed by a non-specific IgG.

FIG. 11 illustrates the results of Example 11. The vertical axis represents a value produced by subtracting a value of the thickness of an auricle before the test from a value of the thickness of the auricle after the test (i.e., an index indicating the swelling of the auricle). In the transverse axis, "Het" represents a RBMS2 gene heterozygously deficient mouse, and "KO" represents a RBMS2 gene homozygously deficient mouse.

FIG. 12 illustrates the results of Example 12. The vertical axis represents an expression amount/level of mRNA in the case where siRNA for RBMS2 is allowed to transfect, and the transverse axis represents an expression amount/level of mRNA in the case where non-specific siRNA (negative control) is allowed to transfect. Each plot represents a gene of which the expression amount/level is 2-fold or more increased or is 2-fold or more decreased by the knockdown of RBMS2.

MODE FOR CARRYING OUT THE INVENTION

1. Definitions

The wordings "contain" and "comprise" as used herein include all of the concepts of "contain", "comprise", "substantially consisting of" and "consisting only of".

The amino acid sequence "identity" refers to the degree of amino acid sequence agreement between at least two amino acid sequences that can be compared with each other. Therefore, the identity or similarity of two amino acid sequences becomes higher with the increase in the degree of amino acid sequence agreement between the amino acid sequences. The level of amino acid sequence identity can be determined using FASTA as a sequence analysis tool and employing a default parameter. Alternatively, the level of amino acid sequence identity can also be determined using an algorithm BLAST established by Karlin and Altschul (Karlin S, Altschul S F. "Methods for assessing the statistical significance of molecular sequence features by using general scoringschemes" Proc Natl Acad Sci USA. 87:2264-2268 (1990), Karlin S, Altschul S F. "Applications and statistics for multiple high-scoring segments in molecular sequences." Proc Natl Acad Sci USA. 90:5873-7 (1993)). A program called "BLASTX" which relies on the algorithm BLAST has been developed. Specific techniques for these analysis methods are known, and see a web site of National Center of Biotechnology Information (NCBI) (ncbi.nlm.nih.gov/). The nucleotide sequence "identity" can also be defined accordingly as mentioned above.

The term "conservative substitution" as used herein refers to the matter that an amino acid residue is substituted by an amino acid residue having a similar side chain. For example, the substitution between amino acid residues each having a basic side chain, e.g., lysine, arginine, histidine, is included within the scope of the conservative substitution. In addition, the substitution between amino acid residues each having an acidic side chain, e.g., aspartic acid, glutamic acid, the substitution between amino acid residues each having an uncharged polar side chain, e.g., glycine, asparagine, glutamine, serine, threonine, tyrosine and cysteine, the substitution between amino acid residues each having a non-polar side chain, e.g., alanine, valine, leucine, isoleucine, proline, phenylalanine, methionine and tryptophan, the substitution between amino acid residues each having a β-branched side chain, e.g., threonine, valine and isoleucine, and the substitution between amino acid residues each having an aromatic side chain, e.g., tyrosine, phenylalanine, tryptophan and histidine, are included within the scope of the conservative substitution.

In the description, the expression "RBMS2" means RBMS2 protein.

In the description, each of "a nucleotide", "an oligonucleotide" and "a polynucleotide" has the same meaning as "a nucleic acid", and both of DNA and RNA are included. Each of these substances may be in a double-stranded form or a single-stranded form. The term a "nucleotide" (or an "oligonucleotide" or a "polynucleotide") having a given sequence also includes a "nucleotide" (or an "oligonucleotide" or a "polynucleotide") having a sequence complementary to the sequence therefor comprehensively, unless otherwise stated. In addition, in the case where the "nucleotide" (or an "oligonucleotide" or a "polynucleotide") is RNA, the nucleotide symbol "T" shown in a sequence for the nucleotide is to be read "U".

2. Expression Cassette

The present invention relates to an expression cassette (also sometimes referred to as an "expression cassette of the present invention", hereinafter) which contains a RBMS2 gene expression regulation region and a gene arranged in such a manner that the expression thereof can be regulated by the region. Hereinbelow, the expression cassette will be described.

In the present application, the term an "expression cassette" refers to a polynucleotide having such a function that a gene contained in the expression cassette can be expressed in a cell (e.g., a eukaryotic cell, preferably an animal cell, more preferably a mammalian cell).

In the present application, the "RBMS2 gene expression regulation region" is not particularly limited, as long as the region is a DNA region capable of regulating the expression of endogenous RBMS2 gene in a cell or a DNA region having the same regulation ability as that of the aforementioned DNA region. An example of the region is a promoter that contains a transcription initiation site for RBMS2 gene, a sequence located upstream (5' side) from the transcription initiation site, and optionally a sequence located downstream (3' side) from the transcription initiation site. A specific example of the promoter is a DNA region lying between −10000 to +2000, preferably −5000 to +1000, more preferably −2000 to +500, further preferably −1000 to +200, still further preferably −500 to +100, especially preferably −200 to +50, wherein a nucleotide corresponding to the transcription initiation site for RBMS2 gene is expressed as "+1", a nucleotide located downstream (3' side) from the aforementioned nucleotide is expressed by a positive value, and a nucleotide located upstream from the aforementioned nucleotide is expressed by 0 or a negative value. The promoter may have a mutation, as long as the promoter has the same level of expression regulation ability as that of a promoter capable of regulating the expression of endogenous RBMS2 gene in a cell. In this case, the nucleotide sequence for the promoter having a mutation has, for example, a 70% or more, preferably 80% or more, more preferably 90% or more, further preferably 95% or more, still further preferably 97% or more, especially preferably 99% or more identity to a nucleotide sequence for a promoter capable of regulating the expression of endogenous RBMS2 gene in a cell. It is desirable that the position of the mutation is a position other than the position of a known expression regulation element (e.g., a basic transcription factor binding region, any one of various activator binding regions). The consensus sequence for the expression regulation element is already known, and can be searched easily on various data base.

In the present application, "RBMS2 gene" is not particularly limited, and examples of the gene include those from animals including various mammals such as human, monkey, mouse, rat, dog, cat, rabbit, pig, horse, cow, sheep, goat and deer.

RBMS2 genes derived from various animals are known. Specific examples of RBMS2 mRNA and RBMS2 protein which are expression products of the RBMS2 genes include human RBMS2 mRNA such as mRNA consisting of the nucleotide sequence represented by SEQ ID NO: 3 (NCBI Reference Sequence: NM_002898.3); murine RBMS2 mRNA such as mRNA consisting of the nucleotide sequence represented by SEQ ID NO: 4 (NCBI Reference Sequence: NM_019711.2); human RBMS2 protein such as a protein consisting of the amino acid sequence represented by SEQ ID NO: 2 (NCBI Reference Sequence: NP_002889.1); and murine RBMS2 protein such as a protein consisting of the amino acid sequence represented by SEQ ID NO: 5 (NCBI Reference Sequence: NP_062685.2). The RBMS2 protein includes, within the scope thereof, a type in which the N-terminal is deleted. Specific examples of the RBMS2 protein of this type include a mouse-derived protein, which is consisting of the amino acid sequence represented by SEQ ID NO: 6 (NCBI Reference Sequence: NP_001034169.1) (whose mRNA is consisting of the nucleotide sequence represented by SEQ ID NO: 7 (NCBI Reference Sequence: NM_001039080.1)).

RBMS2 protein, which is an expression product of RBMS2 gene, may have an amino acid mutation such as substitution, deletion, addition and insertion, as long as the RBMS2 protein can have an activity to promote the expression of mRNA having a 3'UTR derived from inflammation promoting factor mRNA (e.g., IL-6 mRNA, COX-2 mRNA, IL-8 mRNA, IL-1β mRNA, TNF-α mRNA, MMP1 mRNA, IL-24 mRNA, c-Myc mRNA) or a protein translated from the mRNA (wherein the activity is also referred to as an "inflammation promoting factor expression promoting activity", hereinafter). From the viewpoint that the inflammation promoting factor expression promoting activity is less likely to be deteriorated, the type of the mutation is preferably substitution, more preferably conservative substitution.

RBMS2 mRNA, which is a transcription product of RBMS2 gene, may have a nucleotide mutation, such as substitution, deletion, addition and insertion, as long as a protein translated from the mRNA can have an inflammation promoting factor expression promoting activity. The type of the mutation is preferably a mutation by which an amino acid substitution does not occur in a protein translated from the mRNA or a mutation by which a conservative substitution of an amino acid residue can occur.

The presence or absence of an inflammation promoting factor expression promoting activity can be determined by or in accordance with a known method. For example, this presence or absence can be determined by or in accordance with the methods described in the section "Examples". A specific example is as follows: in Example 1B, when an expression vector for a test protein is used as the expression vector, it is determined that the test protein has an inflammation promoting factor expression promoting activity when the luciferase activity is higher than that achieved when an empty vector is used as the expression vector.

A preferred specific example of RBMS2 protein which is an expression product of RBMS2 gene is at least one protein selected from the group consisting of a protein mentioned in (a) and a protein mentioned in (b):

(a) a protein which is consisting of an amino acid sequence represented by SEQ ID NO: 2, 5 or 6; and (b) a protein which has 85% or more identity to an amino acid sequence represented by SEQ ID NO: 2, 5 or 6 and has an inflammation promoting factor expression promoting activity.

In (b), the degree of identity is more preferably 90% or more, further preferably 95% or more, still further preferably 98% or more.

An example of the protein mentioned in (b) is:

(b') a protein which is consisting of an amino acid sequence having the substitution, deletion, addition or insertion of one or several amino acid residues in an amino acid sequence represented by SEQ ID NO: 2, 5 or 6 and has an inflammation promoting factor expression promoting activity.

In (b'), the wording "several amino acid residues" refers to, for example, 2 to 30 amino acid residues, preferably 2 to 10 amino acid residues, more preferably 2 to 5 amino acid residues, still further preferably 2 or 3 amino acid residues.

A preferred specific example of RBMS2 mRNA which is a transcription product of RBMS2 gene is at least one component selected from the group consisting of mRNA mentioned in (c) and mRNA mentioned in (d):

(c) mRNA consisting of a nucleotide sequence represented by SEQ ID NO: 3, 4 or 7; and (d) mRNA which has 85% or more identity to a nucleotide sequence represented by SEQ ID NO: 3, 4 or 7 and encodes a protein having an inflammation promoting factor expression promoting activity.

In (d), the degree of identity is more preferably 90% or more, further preferably 95% or more, still further preferably 98% or more.

An example of the protein mentioned in (d) is:

(d') a protein which is consisting of a nucleotide sequence having the substitution, deletion, addition or insertion of one or several nucleotides in a nucleotide sequence represented by SEQ ID NO: 3, 4 or 7 and has an inflammation promoting factor expression promoting activity.

In (d'), the wording "several nucleotides" refers to, for example, 2 to 500 nucleotides, preferably 2 to 100 nucleotides, more preferably 2 to 50 nucleotides, still further preferably 2 to 10 nucleotides.

In the present application, the term "gene" which is arranged so that the expression of the gene can be regulated by a RBMS2 gene expression regulation region is not particularly limited, as long as an expression product of the gene can be detected. In this regard, the term "gene" has a concept that a sequence encoding a protein that is an expression product of the gene is included, other sequence in the gene (e.g., an intron sequence) may be included, but a promoter is not contained. Examples of the gene include a reporter gene, a drug-resistant gene, an enzyme gene, a structural gene, a transport gene, a storage gene, a contractile gene, a defense gene, a regulatory gene, and modified genes thereof. Examples of the modified gene include a gene produced by mutating a nucleotide so that an amino acid mutation, e.g., substitution, deletion, addition and insertion, can occur in a part of a protein that is an expression product of the above-mentioned gene; and a gene which can express a protein that is a fusion of expression products of some of the above-mentioned genes. Among these genes, a reporter gene, a drug-resistant gene or the like is preferred, and a reporter gene is more preferred.

In the present application, the "reporter gene" is not particularly limited, as long as the gene is, for example, a gene encoding a light-emitting (color-developing) protein capable of reacting with a specific substrate to emit light (develop a color) or a fluorescent protein capable of emitting fluorescence by the action of excited light. Examples of the light-emitting (color-developing) protein include luciferase, β-galactosidase, chloramphenicol acetyltransferase and β-glucuronidase. Examples of the fluorescent protein include GFP, Azami-Green, ZsGreen, GFP2, HyPer, Sirius, BFP, CFP, Turquoise, Cyan, TFP1, YFP, Venus, ZsYellow, Banana, KusabiraOrange, RFP, DsRed, AsRed, Strawberry, Jred, KillerRed, Cherry, HcRed and mPlum.

In the present application, the "drug-resistant gene" is not particularly limited, as long as the gene is a gene capable of imparting resistance to a drug, e.g., an antibacterial drug, to a cell in which the gene is expressed. Specific examples of the drug-resistant gene include a chloramphenicol-resistant gene, a tetracycline-resistant gene, a neomycin-resistant gene, an erythromycin-resistant gene, a spectinomycin-resistant gene, a kanamycin-resistant gene, a hygromycin-resistant gene and a puromycin-resistant gene.

With respect to the above-mentioned "gene", the wording "(being) arranged so that the expression of the gene can be regulated" means that the gene is arranged so that a protein encoded by the gene can be expressed. A specific example of the arrangement is an aspect in which the gene expression regulating region and the gene are arranged in this order as observed from the 5'-side.

If necessary, the expression cassette of the present invention may contain other element (e.g., a multi-cloning site (MCS)). For example, in the case where a RBMS2 gene expression regulation region and the above-mentioned "gene" are arranged in this order as observed from the 5'-side, an aspect can be mentioned in which a MCS is arranged on the 5'-side of the RBMS2 gene expression regulation region (preferably adjacent to the region), or between the RBMS2 gene expression regulation region and the above-mentioned "gene" (preferably adjacent to one or both of the region and the gene), or on the 3'-side of the above-mentioned "gene" (preferably adjacent to the gene). The MCS is not particularly limited, as long as multiple (e.g., 2 to 50, preferably 2 to 20, more preferably 2 to 10) restriction enzyme sites are contained.

The expression cassette of the present invention may constitute a vector by itself or in conjunction with other sequence. The vector (also referred to as a "vector of the present invention", hereinafter) is also included within the scope of the present invention. The "other sequence" is not particularly limited, and any one of various known sequences that can be contained in an expression vector can be used. Examples of the sequence include a replication origin and a drug-resistant gene. With respect to the type of the drug-resistant gene, the above-mentioned types can be mentioned. The type of the vector is not particularly limited, and examples of the vector include a plasmid vector such as an animal cell expressing plasmid; and a virus vector such as a retrovirus, a lentivirus, an adenovirus, an adeno-associated virus, a herpesvirus and a Sendai virus.

The vector according to the present invention may be contained in a cell. The cell (also referred to as "a cell of the present invention", hereinafter) is also included within the scope of the present invention. In the cell of the present invention, the vector of the present invention may be present outside of the genome or may be present in such a form that the vector is integrated in the genome. The organism species from which the cell is derived is not particularly limited, and examples of the species include various mammals such as human, monkey, mouse, rat, dog, cat, rabbit, pig, horse, cow, sheep, goat and deer. The type of the cell is not particularly limited, and cells derived from various tissues or having various properties can be mentioned, such as a blood cell, a hematopoietic stem cell/progenitor cell, a gamete (a sperm, an ovum), a fibroblast, an epithelial cell, a vascular endothelial cell, a nerve cell, a liver cell, a keratin generating cell, a muscle cell, an epidermal cell, an endocrine cell, an ES cell, an iPS cell, a tissue stem cell and a cancer cell.

At least one component selected from the group consisting of the expression cassette of the present invention, the vector of the present invention and the cell of the present invention can be used preferably in the below-mentioned screening method of the present invention. From this viewpoint, the present invention also relates to a reagent for use in the screening for a substance capable of inhibiting the expression or function of RBMS2 (preferably an active ingredient of an inhibitor of the expression of an inflammation promoting factor) (wherein the reagent is also referred to as a "reagent of the present invention", hereinafter), which contains at least one component selected from the group consisting of the expression cassette of the present invention, the vector of the present invention and the cell of the present invention.

The reagent of the present invention is not particularly limited, as long as at least one component selected from the group consisting of the expression cassette of the present invention, the vector of the present invention and the cell of the present invention is contained. In addition, the reagent may also contain, for example, a substance necessary for the detection of an expression product from the expression cassette of the present invention. Specific examples of the substance include a reagent for hybridization, a label for a probe, a labeled body detection agent, a buffer solution and a device. The reagent of the present invention may be in the form of a screening kit including these components.

3. A Screening Method

The present invention relates to a method for screening for a substance capable of inhibiting the expression or function of RBMS2 by employing at least one item selected from the group consisting of items (i) to (iii) as an index in the presence of a test substance:

(i) the expression amount/level of a gene of which the expression can be regulated by a RBMS2 gene expression regulation region;

(ii) the binding amount/level of RBMS2 to RNA containing an AU-rich element; and (iii) the amount/level of mRNA containing an AU-rich element in a 3'-UTR thereof or the amount/level of a protein derived from the mRNA in a RBMS2-overexpressing cell. Hereinbelow, the expression cassette will be described (wherein the reagent is also referred to as a "screening method of the present invention", hereinafter).

As the "test substance (i.e., substance to be tested)" to be used in the present application, any one of wide varieties of compounds can be used, regardless of the fact that the compound is a naturally occurring compound or an artificially produced compound. Alternatively, a purified compound, a composition prepared by mixing many types of compounds together, or an extract of an animal or plant origin may also be used. The compound includes a low-molecular-weight compound as well as a high-molecular-weight compound such as a protein, a nucleic acid and a polysaccharide.

More specific examples of the screening method, when the value of the index in the presence of a test substance is smaller than the value of the index in the absence of the test substance, the test substance can be selected as a substance capable of inhibiting the expression or function of RBMS2.

The screened "substance capable of inhibiting the expression or function of RBMS2" can be selected as an active ingredient for an inhibitor of the expression of an inflammation promoting factor or a candidate substance for the active ingredient.

Herein below, specific screening methods for the aspects which utilize the indices (i) to (iii), respectively, will be described.

3-1. Screening Method Using Index (i)

A screening method using index (i) includes steps (a1) to (c1):

(a1) bringing an expression system which contains an expression cassette containing a RBMS2 gene expression regulation region and a gene arranged in such a manner that the expression thereof can be regulated by the region into contact with a test substance;

(b1) measuring, as an expression amount/level of interest, the amount/level of the gene expressed in the expression system that has been contacted with the test substance and then comparing the expression amount/level of interest with a control expression amount/level that is the expression amount/level of the gene in an expression system that has not been contacted with the test substance; and (c1) selecting the test substance as a substance capable of inhibiting the expression of RBMS2 when the expression amount/level of interest is smaller than the control expression amount/level.

In step (a1), the "expression cassette containing a RBMS2 gene expression regulation region and a gene arranged in such a manner that the expression thereof can be regulated by the region" is as mentioned in the section "2. Expression cassette". However, the expression cassette in step (al) is different from the expression cassette in the section "2. Expression cassette" in that the expression cassette in step (al) includes an expression cassette containing an endogenous RBMS2 gene expression regulation region in the genome of a cell and RBMS2 gene located downstream from the region.

In step (a1), the "expression system" is not particularly limited, as long as a component necessary for the expression of a gene from the expression cassette is contained. Examples of the expression system include a cell-free protein expression system and a cell. The cell-free protein expression system is generally consisting of a solution (e.g., a liquid extract from cells) containing a factor necessary for transcription and translation (e.g., an RNA polymerase, a ribosome, any one of various ribonucleotides), and a commercially available product may be used. The cell is not particularly limited, as long as a gene can be expressed from the expression cassette in the cell. Examples of the cell include a cell derived from any one of various tissues or a cell having any one of various properties, such as a blood cell, a hematopoietic stem cell/progenitor cell, a gamete (a sperm, an ovum), a fibroblast, an epithelial cell, a vascular endothelial cell, a nerve cell, a liver cell, a keratin generating cell, a muscle cell, an epidermal cell, an endocrine cell, an ES cell, an iPS cell, a tissue stem cell and a cancer cell. From the viewpoint that the screening can be performed more easily, the expression system is preferably a cell.

In step (a1), in the case where the expression system containing the expression cassette is a cell-free protein expression system, it is preferred that the expression cassette is contained in the solution in the system. In the case where the expression system is a cell, there are an aspect where the expression cassette is integrated into the genome of the cell, an aspect where the expression cassette is present outside of the genome of the cell (e.g., in the form of a plasmid), and the like.

In step (a1), the aspect of bringing the test substance into contact is not particularly limited. In the case where the expression system is a cell-free protein expression system, it is preferred to add the test substance to the solution in the system, for example. In the case where the expression system is a cell, it is preferred to add the test substance to a cell culture medium, for example.

In step (a1), the contacting time of the test substance is not particularly limited, and can be set appropriately depending on the type of the test substance, the type of the expression system and others. The time is, for example, 5 minutes to 72 hours.

In step (b1), the measurement of the expression amount/level of interest and the control expression amount/level can be carried out in accordance with or based on a known method. It is preferred to carry out the measurement using the diagnostic agent of the present invention mentioned above. In the case where the substance to be measured is a nucleic acid (RBMS2 mRNA or a nucleic acid derived therefrom (e.g., cDNA)), the measurement can be carried out by a northern blotting method, a RT-PCR method, a DNA chip analysis method, an in situ hybridization analysis method or the like using the nucleic acid as a probe or a primer, for example. In the case where the substance to be measured is a protein, the measurement can be carried out by a western blotting method, an ELISA method or the like using a specific antibody. In the case where the substance to be measured is a reporter protein, the measurement can be carried out by a method capable of detecting a reporter signal (e.g., a fluorescence, a developed color, emitted light) coming from the reporter protein (e.g., the microscopic observation of fluorescence, a luciferase assay). In the case where the substance to be measured is a drug-resistant protein, the measurement can be carried out indirectly by counting the number of cells surviving in the presence of the drug.

In the case where a northern blotting method is employed, concretely, a method can be exemplified, in which a probe is labeled with a radioactive isotope (e.g., $^{32}$P, $^{33}$P: RI), a fluorescent substance or the like, then the labeled probe is hybridized with mRNA derived from the expression system and transferred onto a nylon membrane or the like in the conventional manner, and then a double strand formed by the diagnostic agent and mRNA derived from the sample from the subject is subjected to the detection and measurement of a signal coming from a labeled probe (a labeling substance such as an RI or a fluorescent substance) using a radioactive ray detector BAS-1800II (manufactured by Fujifilm Corporation), a fluorescence detector or the like. Alternatively, a method may also be employed, in which the diagnostic agent is labeled using AlkPhos Direct Labelling and Detection System (manufactured by Amersham Pharmacia Biotech) in accordance with the protocol, then the labeled diagnostic agent is hybridized with mRNA derived from the expression system, and then a signal coming from a labeled product of the diagnostic agent is detected and measured using a multibioimager STORM860 (manufactured by Amersham Pharmacia Biotech).

In the case where a RT-PCR method is employed, concretely, a method can be exemplified, in which cDNA is prepared from RNA derived from the expression system in the conventional manner, then a pair of primers prepared from the diagnostic agent of the present invention (i.e., a positive strand capable of binding to the cDNA (− strand), a negative strand capable of binding to + strand) are hybridized with the cDNA to perform a PCR method so that a target region can be amplified using the cDNA as a template, and then amplified double-stranded DNA thus produced is detected. For the detection of the amplified double-stranded DNA, a method in which the above-mentioned PCR is carried out using a primer that is labeled with an RI or a fluorescent substance in advance to detect labeled double-stranded DNA produced; a method in which double-stranded DNA thus produced is transferred onto a nylon membrane or the like in the conventional manner, then the labeled probe is used as a probe and is hybridized with the double-stranded DNA, and then a hybridized product is detected; and other method can be employed. In this regard, a labeled double-stranded DNA product thus produced can be measured using an arrangement 2100 bioanalyzer (manufactured by Yokogawa Analytical Systems, Inc.) or the like. Alternatively, it is also possible to prepare a RT-PCR reaction solution using SYBR Green RT-PCR Reagents (manufactured by Applied Biosystems) in accordance with the protocol, then react the reaction solution using ABI PRISM 7700 Sequence Detection System (manufactured by Applied Biosystems), and then detect a reaction product.

In the case where DNA chip analysis is utilized, a method can be mentioned, in which a DNA chip to which a (single-stranded or double-stranded) DNA probe is attached is provided, then the DNA chip is hybridized with cRNA prepared from RNA derived from the expression system in the conventional manner to produce a double-stranded product formed from the DNA and the cRNA, then the double-stranded product is bonded to a labeling probe prepared from the diagnostic agent of the present invention, and then the bonded product is detected.

As the western blotting method, a method can be exemplified, in which a primary antibody is used, then a labeled antibody (an antibody capable of binding to the primary antibody) that is labeled with a radioactive isotope such as $^{125}$I, a fluorescent substance, an enzyme such as horseradish peroxidase (HRP) or the like is used as a secondary antibody, and a signal coming from the labeling substance, e.g., the radioactive isotope, the fluorescent substance or the like, in the labeled compound is detected using a radioactive ray measurement device BAS-1800II (manufactured by Fujifilm Corporation), a fluorescence detector or the like. Alternatively, it is also possible to use a primary antibody, then the signal is detected using ECL Plus Western Blotting Detection System (manufactured by Amersham Pharmacia Biotech) in accordance with the protocol and is then measured using multibioimager STORM860 (manufactured by Amersham Pharmacia Biotech).

In step (c1), for example, in the case where the expression amount/level of interest is smaller than the control expression amount/level, the test substance can be selected as a substance capable of inhibiting the expression of RBMS2 when the expression amount/level of interest is smaller by ½, ⅕, ¹⁄₁₀, ¹⁄₂₀, ¹⁄₅₀ ¹⁄₁₀₀ than the control expression amount/level.

3-2. Screening Method Using Index (ii)

A screening method using index (ii) includes steps (a2) to (c2):

(a2) bringing RNA containing an AU-rich element into contact with RBMS2 in the presence of a test substance;

(b2) measuring the binding amount/level between the RNA and the RBMS2 which are contacted with each other in the presence of a test substance as a binding amount/level of interest, and then comparing the binding amount/level of interest with a control binding amount/level that is the binding amount/level between the RNA and the RBMS2 which are contacted with each other in the absence of the test substance; and (c2) selecting the test substance as a substance capable of inhibiting the function of RBMS2 when the binding amount/level of interest is smaller than the control binding amount/level.

In step (a2), the "AU-rich element" refers to an element in which a nucleotide sequence represented by general formula: $(U)_n W^1 (U)_m W^2 (U)_o$ [wherein U represents an uracil; $W^1$ and $W^2$ may be the same as or different from each other and independently represent an adenine or uracil (provided that a case where each of $W^1$ and $W^2$ represents an uracil is excluded); n represents an integer of 0 to 3; o represents an integer of 0 to 3; and m represents an integer of 3 to 5 (preferably 3)] typified by a sequence AUUUA is a consensus sequence. The AU-rich element is preferably an AU-rich element derived from mRNA of an inflammation promoting factor (e.g., at least one type of mRNA selected from the group consisting of IL-6 mRNA, COX-2 mRNA, IL-8 mRNA, IL-1β mRNA, TNF-α mRNA, MMP1 mRNA, IL-24 mRNA and c-Myc mRNA). In other words, the term "an AU-rich element derived from . . . " refers to an AU-rich element contained in each of these mRNA.

In step (a2), the RNA containing an AU-rich element is not particularly limited, as long as the RNA contains the AU-rich element. The number of the AU-rich elements in the RNA is, for example, 1 to 20, preferably 2 to 15, more preferably 3 to 12, further preferably 4 to 10, still further preferably 6 to 9. When the number of the AU-rich elements in the RNA is multiple, it is desirable that the AU-rich elements are present in a relatively narrow region (e.g., 20 to 400 bp, preferably 40 to 200 bp, more preferably 60 to 150 bp, further preferably 80 to 120 bp). It is preferred that the region is U-rich. The degree of U-richness is as follows: the rate of the number of U residues relative to the total number of nucleotides in the region is, for example, 20% or more, preferably 30% or more, more preferably 50% or more. The upper limit of the ratio is not particularly limited, and examples of the upper limit include 90%, 80%, 70% and the like.

In step (a2), the RBMS2 is the same as that in the RBMS2 protein mentioned in the section "2. Expression cassette".

In step (a2), the aspect of bringing the test substance into contact is not particularly limited, as long as the three components, i.e., the RNA containing an AU-rich element, RBMS2 and the test substance, can be contacted with one another. For example, an aspect where the three components are mixed together in a proper solvent, an aspect where the three components are allowed to co-exist in a cell, and the like can be mentioned.

In step (a2), the contacting time of the test substance is not particularly limited, and can be set appropriately depending on the type of the test substance, whether the contact is achieved in a test tube or in a cell, or the like. The time is, for example, 5 minutes to 72 hours.

In step (b2), the measurement of the binding amount/level of interest and the control binding amount/level can be carried out by or in accordance with a known method. For example, the measurement can be carried out by an immunoprecipitation method, a gel shift method or the like.

The immunoprecipitation method can be carried out typically in the following manner. A cell lysate each containing RNA containing an AU-rich element and RBMS2 (and being in contact with the test substance or being not in contact with the test substance) is prepared, then the lysate is immunoprecipitated with an antibody directed against RBMS2 or an antibody directed against a tag in the case where the tag is attached to the RBMS2, and then the amount/level of "RNA containing an AU-rich element" contained in a precipitate is measured by a PCR. It is demonstrated that the binding amount/level of interest or the control binding amount/level becomes larger with the increase in the measured amount/level.

A gel shift method can be carried out typically in the following manner. A solution containing the RNA containing an AU-rich element and RBMS2 (and further containing the test substance or not containing the test substance) is electrophoresed using a proper gel (e.g., an acrylamide gel), and then a signal of a band that indicates a complex of the RNA containing an AU-rich element and RBMS2 which are bonded together is measured. It is demonstrated that the binding amount/level of interest or the control binding amount/level becomes larger with the increase in the measured amount/level.

In step (c2), for example, in the case where the binding amount/level of interest is smaller than the control binding amount/level, the test substance can be selected as a substance capable of inhibiting the expression of RBMS2 when the binding amount/level of interest is smaller by ½, ⅕, ¹/₁₀, ¹/₂₀, ¹/₅₀ ¹/₁₀₀ than the control binding amount/level.

3-3. Screening Method Using Index (iii)

A screening method using index (iii) includes steps (a3) to (c3):

(a3) bringing a cell which contains mRNA containing an AU-rich element in a 3'-UTR thereof and in which RBMS2 is overexpressed into contact with a test substance;

(b3) measuring the amount/level of the mRNA or a protein derived from the mRNA in the cell that has been contacted with the test substance as an amount/level of interest, and then comparing the amount/level of interest with a control amount/level that is the amount/level of the mRNA or a protein derived from the mRNA in a cell that is not contacted with the test substance; and (c3) selecting the test substance as a substance capable of inhibiting the function of RBMS2 when the amount/level of interest is smaller than the control amount/level.

In step (a3), the AU-rich element is the same as that mentioned in the section "3-2. Screening method using index (ii)".

In step (a3), the mRNA containing an AU-rich element in a 3'-UTR thereof is not particularly limited, as long as the mRNA contains an AU-rich element in a 3'-UTR thereof. The number of AU-rich elements in the 3'-UTR of the mRNA is, for example, 1 to 20, preferably 2 to 15, more preferably 3 to 12, further preferably 4 to 10, and still further preferably 6 to 9. In the case where the number if AU-rich elements in the mRNA is multiple, it is desirable that the AU-rich elements are present in a relatively narrow region (e.g., 20 to 400, preferably 40 to 200, more preferably 60 to 150, further preferably 80 to 120).

In step (a3), the mRNA containing an AU-rich element in the 3'-UTR thereof is preferably mRNA for an inflammation promoting factor, more preferably IL-6 mRNA, COX-2 mRNA, IL-8 mRNA, IL-1β mRNA, TNF-α mRNA, MMP1 mRNA, IL-24 mRNA, c-Myc mRNA or the like, or a variant of any one of these mRNA molecules. As the variant, mRNA in which one or several (e.g., 2 to 50, preferably 2 to 20, more preferably 2 to 10, further preferably 2 to 5, still further preferably 2 or 3) nucleotides are substituted, deleted, added or inserted preferably in a sequence other than the AU-rich element or a part of the AU-rich element can be mentioned.

In step (a3), the RBMS2 is the same as the RBMS2 protein in the section "2. Expression cassette".

In step (a3), the cell is the same as the cell in the section "3-1. Screening method using index (i)".

In step (a3), the aspect of bringing the test substance into contact is not particularly limited. For example, an aspect where the test substance is added to the cell culture medium can be mentioned.

In step (a3), the contacting time of the test substance is not particularly limited, and can be set appropriately depending on the type of the test substance and the like. The time is, for example, 5 minutes to 72 hours.

In step (b3), the measurement of the amount/level of interest and the control amount/level is carried out in the same manner as in the measurement of the expression amount/level of interest and the control expression amount/level in the section "3-1. Screening method using index (i)".

In step (c3), in the case where the amount/level of interest is smaller than the control amount/level, the test substance can be selected as a substance capable of inhibiting the expression of RBMS2 when the amount/level of interest is smaller by ½, ⅕, ¹/₁₀, ¹/₂₀, ¹/₅₀ or ¹/₁₀₀ than the control amount/level.

4. Inhibitor of Expression of Inflammation Promoting Factor

The present invention relates to an inhibitor of the expression of an inflammation promoting factor (wherein the inhibitor is also referred to as "the agent of the present invention" in the description) which contains at least one component selected from the group consisting of a RBMS2 expression inhibitor and a RBMS2 function inhibitor. Hereinbelow, the inhibitor will be described.

The RBMS2 of which the expression and function are to be inhibited is the same as the RBMS2 protein in the section "2. Expression cassette" above.

The RBMS2 expression inhibitor is not particularly limited, as long as the inhibitor can reduce the expression amount/level of RBMS2 protein. Specific examples of the inhibitor include RBMS2-specific small interfering RNA (siRNA), RBMS2-specific microRNA (miRNA), a RBMS2-specific antisense nucleic acid, and expression vectors therefore. In addition, it is mentioned in the section "Examples" that IL-10 protein can act as a RBMS2 expression inhibitor.

The RBMS2-specific siRNA is not particularly limited, as long as the siRNA is a double-stranded RNA molecule capable of specifically inhibiting the expression of a gene encoding RBMS2. In one embodiment, the siRNA preferably has a length of 18 nucleotides or more, 19 nucleotides or more, 20 nucleotides or more, or 21 nucleotides or more. The siRNA preferably has a length of, for example, 25 nucleotides or less, 24 nucleotides or less, 23 nucleotides or less, or 22 nucleotides or less. It is conceived that the value of the upper limit and the value of the lower limit of the length of the siRNA which are mentioned herein can be combined arbitrarily. For example, the following combinations of the length can be conceived: a length in which the lower limit is 18 nucleotides and the upper limit is 25 nucleotides, 24 nucleotides, 23 nucleotides, or 22 nucleotides; a length in which the lower limit is 19 nucleotides and the upper limit is 25 nucleotides, 24 nucleotides, 23 nucleotides, or 22 nucleotides; a length in which the lower limit is 20 nucleotides and the upper limit is 25 nucleotides, 24 nucleotides, 23 nucleotides, or 22 nucleotides; and a length in which the lower limit is 21 nucleotides and the upper limit is 25 nucleotides, 24 nucleotides, 23 nucleotides, or 22 nucleotides.

The siRNA may be shRNA (small hairpin RNA). The shRNA can be designed so that a part thereof forms a stem loop structure. For example, when a sequence lying in a specific region is named "sequence a" and a complementary strand to the sequence a is named "sequence b", the shRNA can be designed in such a manner that the sequence a, a spacer and the sequence b are arranged in this order on a single RNA strand and the whole length becomes 45 to 60 nucleotides. The sequence a is a sequence for a partial region of the nucleotide sequence encoding the target RBMS2, and the target region is not limited particularly, and an arbitrary region can be employed as a candidate. The length of the sequence a is 19 to 25 nucleotides, preferably 19 to 21 nucleotides.

The RBMS2-specific siRNA may have additional nucleotides at the 5'- or 3'-terminal thereof. The length of the additional nucleotides is generally about 2 to 4 nucleotides. The additional nucleotides may be in the form of DNA or RNA. When additional nucleotides are in the form of DNA, the stability of the nucleic acid may be improved. Examples of the sequence for the additional nucleotides include, but are not limited to, ug-3', uu-3', tg-3', tt-3', ggg-3', guuu-3', gttt-3', ttttt-3' and uuuuu-3'.

The siRNA may have an overhang at the 3'-terminal thereof, and a specific example of the overhang is dTdT (wherein dT represents a deoxythymidine). Alternatively, the siRNA may have a blunt end without the addition of a terminal. In the siRNA, the number of nucleotides in a sense strand may be different from that in an antisense strand. For example, the siRNA may be "asymmetrical interfering RNA (aiRNA)" in which the antisense strand has an overhang at each of the 3'-terminal and the 5'-terminal. Typical aiRNA is one in which the antisense strand is consisting of 21 nucleotides, the sense strand is consisting of 15 nucleotides, and an overhang structure consisting of 3 nucleotides is formed at each terminal of the antisense strand.

The position of the target sequence in the RBMS2-specific siRNA is not particularly limited. In one embodiment, it is desirable to select the target sequence from a 5'-UTR and a sequence lying between the initiation codon and about 50th nucleotide from the initiation codon and not to select the target sequence from a 3'-UTR. It is preferred that candidates for the selected target sequence are determined with respect to the matter that there is no homology in a sequence consisting of contiguous 16 to 17 nucleotides in mRNA other than the target sequence using a homology search software such as BLAST (ncbi.nlm.nih.gov/BLAST/), and the specificity of the selected target sequence is confirmed. With respect to a target sequence of which the specificity has been confirmed, double-stranded RNA which is consisting of a sense strand having a 3'-terminal TT or UU overhang in a sequence lying between 19st nucleotide and 21st nucleotide following AA (or NA) and an antisense strand which is consisting of a sequence complementary to the sequence lying between 19st nucleotide and 21st nucleotide and a 3'-terminal TT or UU overhang may be designed as the siRNA. shRNA, which is a precursor of the siRNA, can be designed by appropriately selecting an arbitrary linker sequence (e.g., about 5 to 25 nucleotides) that can form a loop structure and then connecting the sense strand to the antisense strand with the linker sequence interposed therebetween.

The sequence for the siRNA and/or the shRNA can be searched using various search software which is provided for free on web sites. Examples of the sites are as follows. siRNA Target Finder (ambion.com/jp/techlib/misc/siRNA_finder.html) provided by Ambion, pSilencer (registered trademark) Insert design tool for Expression Vectors (ambion.com/jp/techlib/mise/psilencer_converter.html) GeneSeer (codex.cshl.edu/scripts/newsearchhairpin.cgi) provided by RNAi Codex.

The siRNA can be prepared by separately synthesizing an sense strand and an antisense strand in the target sequenced on mRNA using a DNA/RNA automatic synthesizer, then denaturing these strands in a proper annealing buffer solution at about 90 to 95° C. for about 1 minute and then annealing the resultant product at about 30 to about 70° C. for about 1 to about 8 hours. Alternatively, the siRNA may also be prepared by synthesizing shRNA that is a precursor of the siRNA and then cutting the shRNA with a RNA cutting protein dicer.

The RBMS2-specific miRNA may be any one, as long as the miRNA can inhibit the translation of a gene encoding RBMS2. For example, the miRNA may inhibit the translation of target mRNA by forming a pair with a 3'-untranslated region (UTR) in the target rather than by cutting the target mRNA like siRNA. The miRNA may be any one of pri-miRNA (primary miRNA), pre-miRNA (precursor miRNA) and mature miRNA. The length of the miRNA is not particularly limited, and the length of the pri-miRNA is generally several hundreds to several thousands of nucleotides, the length of the pre-miRNA is generally 50 to 80 nucleotides, and the length of the mature miRNA is generally 18 to 30 nucleotides. In one embodiment, the RBMS2-specific miRNA is preferably pre-miRNA or mature miRNA, more preferably mature miRNA. The RBMS2-specific miRNA may be synthesized by a known procedure, or may be purchased from a synthetic RNA supplier company.

The RBMS2-specific antisense nucleic acid contains a nucleotide sequence complementary or substantially complementary to the nucleotide sequence for mRNA of a gene encoding RBMS2 or a part of the nucleotide sequence, and has a function to form a specific and stable double strand with the mRNA and bind to the mRNA so as to inhibit the synthesis of RBMS2 protein. The antisense nucleic acid may be any one selected from DNA, RNA and DNA/RNA chimera. In the case where the antisense nucleic acid is DNA, an RNA:DNA hybrid formed from a target RNA and the antisense DNA can be recognized by endogenous ribonuclease H (RNase H) to cause the selective degradation of the target RNA. Therefore, in the case of antisense DNA that directs the degradation with RNase H, the target sequence may be contained in mRNA as well as a sequence for an intron region in an RBMS2 initial translation product. The intron sequence can be determined by comparing the genome sequence with cDNA nucleotide sequence in RBMS2 gene using a homology search program such as BLAST and FASTA.

The length of the target region in the RBMS2-specific antisense nucleic acid is not particularly limited, as long as the antisense nucleic acid can hybridize with the target region so as to inhibit the translation into RBMS2 protein. The RBMS2-specific antisense nucleic acid may be the full length or a partial sequence of mRNA encoding RBMS2. From the viewpoint of easiness of the synthesis and the problems of antigenicity and intracellular migration and the like, an oligonucleotide having a length of about 10 to about 40 nucleotides, particularly about 15 to about 30 nucleotides, is preferred, but the oligonucleotide is not limited thereto. More concretely, a preferred target region for the antisense nucleic acid can be selected from a 5'-terminal hairpin loop, a 5'-terminal untranslated region, a translation initiation codon, a protein coding region, an ORF translation stop codon, a 3'-terminal untranslated region, a 3'-terminal palindrome region and a 3'-terminal hairpin loop of RBMS2 gene, but is not limited thereto.

The RBMS2-specific antisense nucleic acid may also be one which can hybridize with mRNA for RBMS2 gene or an initial transcription product of the mRNA to inhibit the translation into a protein and can also bind to these genes, each of which is double-stranded DNA, to form a triplex so as to inhibit the transcription into RNA (i.e., an antigene).

Each of nucleotide molecules that constitute the RBMS2-specific siRNA, the RBMS2-specific miRNA and the RBMS2-specific antisense nucleic acid may contain various chemical modification for the purpose of improving (chemical and/or enzymatical) stability or specific activity (affinity for RNA). For example, in order to prevent the degradation caused by a hydrolysis enzyme such as a nuclease, a phosphate residue (phosphate) in each of the nucleotides constituting the antisense nucleic acid may be substituted by, for example, a chemically modified phosphate residue such as phosphorothioate (PS), methylphosphonate and phosphorodithioate. Alternatively, the hydroxyl group at 2'-position in a ribose in each nucleotide may be substituted by —OR (R=CH$_3$(2'-O-Me), CH$_2$CH$_2$OCH$_3$(2'-O-MOE), CH$_2$CH$_2$NHC(NH)NH$_2$, CH$_2$CONHCH$_3$, or CH$_2$CH$_2$CN, etc.). In addition, the base moiety (pyrimidine, purine) may be chemically modified. For example, the introduction of a methyl group or a cationic functional group to the 5'-position in a pyrimidine base, the substitution of a carbonyl group at 2'-position by a thiocarbonyl group, or the like may be applied. In addition, a part of each of the nucleotide molecules that constitute siRNA and miRNA may be substituted by naturally occurring DNA.

The RBMS2-specific siRNA, the RBMS2-specific miRNA, the RBMS2-specific antisense nucleic acid and the like can be prepared by determining mRNA or a target sequence for an initial transcription product on the basis of the cDNA sequence or the genomic DNA sequence for RBMS2 gene and then synthesizing a sequence complementary to the sequence using a commercially available DNA/RNA automatic synthesizer. The antisense nucleic acid containing the above-mentioned modifications can also be chemically synthesized by a known technique.

The expression vector for the RBMS2-specific siRNA, the RBMS2-specific miRNA or the RBMS2-specific antisense nucleic acid is not particularly limited, as long as the RBMS2-specific siRNA, the RBMS2-specific miRNA or the RBMS2-specific antisense nucleic acid is integrated in an expressible state. Typically, the expression vector contains a promoter sequence, a polynucleotide containing a sequence encoding the RBMS2-specific siRNA, the RBMS2-specific miRNA or the RBMS2-specific antisense nucleic acid (optionally also containing a transcription stop signal sequence) and optionally other sequence. The promoter is not particularly limited, and examples of the promoter include an RNA polymerase II (polII)-type promoter, such as a CMV promoter, an EF1 promoter, an SV40 promoter, a MSCV promoter, a hTERT promoter, a β-actin promoter and a CAG promoter; and a RNA polymerase III (polIII)-type promoter, such as a mouse or human U6-snRNA promoter, a human H1-RNase P RNA promoter and a human valine-tRNA promoter. Among these promoters, a polIII-type promoter is preferred from the viewpoint of the correct transcription ability of short RNA. The "other sequence" is not particularly limited, and any one of various known sequences which can be contained in expression vectors can be employed. Examples of the sequence include a replication origin and a drug-resistant gene. As the types of the drug-resistant gene and the vector, those mentioned above can be exemplified.

Another example of the RBMS2 expression inhibitor is a RBMS2-specific ribozyme. The term "ribozyme" refers to RNA having an enzymatic activity to cleave a nucleic acid in the narrow sense. In the present application, however, DNA can also be included, as long as the DNA has a sequence-specific nucleic acid cleavage activity. The ribozyme having the broadest utility as a ribozyme nucleic acid is self-splicing RNA that is found in infectious RNA such as a viroid and a virusoid, and a hammerhead-type, hairpin-type and the like are known. A hammerhead-type ribozyme nucleic acid can exhibit the enzymatic activity thereof when the length is about 40 nucleotides, and can cleave only target mRNA specifically by converting several nucleotides located in both ends adjacent to a hammerhead structure-forming part (about 10 nucleotides in total) into sequences complementary to a desired cleavage site in mRNA. The ribozyme nucleic acid of this type can utilize only RNA as the substrate thereof, and therefore has such an advantage that the ribozyme nucleic acid never attacks genomic DNA. In the case where the mRNA for the RBMS2 gene forms a double-stranded structure by itself, the target sequence can be made into a single strand by using a hybrid ribozyme to which an RNA motif derived from a viral nucleic acid and capable of binding specifically to an RNA helicase is linked [Proc. Natl. Acad. Sci. USA, 98(10): 5572-5577 (2001)]. In the case where it is intended to use the ribozyme in the form of an expression vector containing DNA encoding the ribozyme, the ribozyme may be used in the form of a hybrid ribozyme to which a tRNA-modified sequence is linked in order to accelerate the migration of a transcript into a cell cytoplasm [Nucleic Acids Res., 29(13): 2780-2788 (2001)].

The RBMS2 function inhibitor is not limited particularly, as long as the inhibitor can inhibit the function of RBMS2 protein. The wording "inhibition of the function of RBMS2 protein" refers to (x) the matter that the binding amount/level between RBMS2 and RNA containing an AU-rich element is reduced and/or (y) the matter that the amount/level of mRNA containing an AU-rich element in the 3'-UTR thereof or the amount/level of a protein derived from the mRNA in an RBMS2-overexpressing cell is reduced. Whether or not the function of RBMS2 protein is inhibited can be determined by, for example, the methods mentioned in the sections "3-2. Screening method using index (ii)" and "3-3. Screening method using index (iii)" below.

The inflammation promoting factor of which the expression is to be inhibited by the agent of the present invention is not particularly limited, as long as the inflammation promoting factor is a factor involved in the induction or worsening of an inflammatory reaction in vivo. Examples of the factor include IL-6, COX-2, IL-1β, IL-8, TNF-α, MMP1, IL-24 and c-Myc.

The agent of the present invention can be used as a prophylactic or therapeutic agent for a disease which can be developed or worsened by an inflammation promoting factor (e.g., IL-6, COX-2, IL-1β, IL-8, TNF-α, MMP1, IL-24, c-Myc). Specific examples of the disease include an immune disease, an inflammatory disease, a painful disease and the like. More specific examples of the disease to be diagnosed include an autoimmune disease, a rheumatic disease, rheumatoid arthritis, a degenerative arthritis disease, arthritis, sepsis, a lymphoproliferative disease, a demyelinating disease in the central nervous system, spondyloarthropathy, inflammatory pain, postoperative pain, allergic disease, preferably an autoimmune disease, rheumatoid arthritis, a lymphoproliferative disease, a demyelinating disease in the central nervous system, postoperative pain and an allergic disease, more preferably rheumatoid arthritis.

Examples of the autoimmune disease in the present application include, but are not limited to Guillain-Barre syndrome, ulcerative colitis, Crohn's disease, Graves' disease, rheumatoid arthritis, systemic lupus erythematosus, polymyositis, scleroderma and Sjogren's syndrome.

Examples of the rheumatic disease in the present application include, but are not limited to rheumatoid arthritis, juvenile idiopathic arthritis, systemic lupus erythematosus, scleroderma, polymyositis, vasculitis syndrome, Behcet's disease, Sjogren's syndrome and psoriatic arthritis.

Examples of the degenerative arthritis disease in the present application include, but are not limited to osteoarthritis of the knee, osteoarthritis of the hip, osteoarthritis of the elbow, osteoarthritis of the shoulder, osteoarthritis of the wrist and osteoarthritis of the foot.

Examples of the lymphoproliferative disease in the present application include, but are not limited to lymphedema, lymphadenitis, malignant lymphoma and Castleman's disease.

Examples of the demyelinating disease in the central nervous system in the present application include, but are not limited to multiple sclerosis, acute disseminated encephalomyelitis and inflammatory diffuse sclerosis.

Examples of the spondyloarthropathy in the present application include, but are not limited to ankylosing spondylitis, reactive arthritis and psoriatic arthritis.

Examples of the inflammatory pain in the present application include, but are not limited to osteoarthritis, low back pain, shoulder periarthritis, cervico-omo-brachial syndrome, flexor tenosynovitis and dental pain.

Examples of the allergic disease in the present application include, but are not limited to an allergic skin disease such as contact dermatitis, eczema, hives, Quincke's edema, erythema nodosum and atopic dermatitis, allergic rhinitis, bronchial asthma, drug allergy and food allergy.

The agent of the present invention is not particularly limited, as long as the agent contains at least one component selected from the group consisting of a RBMS2 expression inhibitor and a RBMS2 function inhibitor (wherein the component is also simply referred to as an "active ingredient" in the description). The agent may additionally contain other component, if necessary. The "other component" is not particularly limited, as long as the component is a pharmaceutically acceptable component. Examples of the "other component" include a base material, a carrier, a solvent, a dispersant, an emulsifying agent, a buffering agent, a stabilizer, an excipient, a binder, a disintegrating agent, a lubricant, a thickening agent, a moisturizing agent, a coloring agent, a fragrance and a chelating agent.

The mode of the usage of the agent of the present invention is not particularly limited, and a proper usage mode can be selected depending on the type of the agent. The agent of the present invention may be used in vitro (e.g., may be added to a culture medium for cultured cells) or may be used in vivo (e.g., may be administered to an animal).

The subject to which the agent of the present invention is to be applied is not particularly limited, and examples of the subject include various mammals such as human, monkey, mouse, rat, dog, cat, rabbit, pig, horse, cow, sheep, goat and deer; and animal cells. The type of the cell is not particularly limited, either. For example, a blood cell, a hematopoietic stem cell/progenitor cell, a gamete (a sperm, an ovum), a fibroblast, an epithelial cell, a vascular endothelial cell, a nerve cell, a liver cell, a keratin generating cell, a muscle cell, an epidermal cell, an endocrine cell, an ES cell, an iPS cell, a tissue stem cell, a cancer cell and the like can be mentioned.

The dosage form of the agent of the present invention is not particularly limited, and a proper dosage form may be selected depending on the mode of the usage of the agent. For example, in the case where it is intended to administer the agent to an animal, examples of the dosage form include an oral preparation such as a tablet, a capsule, a granule, a powder, a fine granule, a syrup, an enteric preparation, a sustained release capsule, a chewable tablet, a drop, a pill, a liquid or solution for oral application, a lozenge, a sustained-release preparation and sustained-release granule; and a preparation for cutaneous application such as a nasal preparation, an inhalation, a suppository for rectal application, a pessary, an enema and a jelly. The agent of the present invention may have any dosage form selected from a solid dosage form, a semi-solid dosage form and a liquid dosage form.

The content of the active ingredient in the agent of the present invention is not limited and varies depending on the intended use of the agent, a subject of the application of the agent, the condition of a subject of the application of the agent, and the like. The content is, for example, 0.0001 to 100% by weight, preferably 0.001 to 50% by weight.

In the case where it is intended to administer the agent to an animal, the amount/level of the agent to be administered is not particularly limited, as long as the amount/level is an amount/level effective for developing the pharmacological activity of the agent. The amount/level is generally 0.1 to 1000 mg/kg body weight per day, preferably 0.5 to 500 mg/kg body weight per day, in terms of the weight of the active ingredient for oral administration, and is generally 0.01 to 100 mg/kg body weight, preferably 0.05 to 50 mg/kg body weight per day, in terms of the weight of the active ingredient for parenteral administration. The dose amount/level is preferably administered in 1, 2 or 3 divided doses, per day, and may be increased or decreased appropriately depending on the age, clinical condition and disease conditions of a subject.

5. Diagnostic Agent

The present invention relates to a diagnostic agent for a disease in an animal, which contains a RBMS2 gene expression product detecting agent (wherein the diagnostic agent is also referred to as a "diagnostic agent of the present invention" in the present description). Hereinbelow, the diagnostic agent will be described.

The RBMS2 gene expression product which is to be detected with the RBMS2 gene expression product detecting agent is not particularly limited, as long as the RBMS2 gene expression product is one which is expressed in a living body of an organism to be diagnosed. Examples of the RBMS2 gene expression product include RBMS2 mRNA or a nucleic acid (e.g., cDNA) derived from the RBMS2 mRNA, RBMS2 protein and the like.

The animal to be diagnosed is not particularly limited, as long as the animal can express RBMS2 gene in vivo. Examples of the animal include various mammals such as human, monkey, mouse, rat, dog, cat and rabbit.

A sequence of RBMS2 mRNA and RBMS2 protein derived from various animals are known. Specific examples of RBMS2 mRNA and RBMS2 protein which are expression products of the RBMS2 genes include human RBMS2 mRNA such as mRNA consisting of the nucleotide sequence represented by SEQ ID NO: 3 (NCBI Reference Sequence: NM_002898.3); murine RBMS2 mRNA such as mRNA consisting of the nucleotide sequence represented by SEQ ID NO: 4 (NCBI Reference Sequence: NM_019711.2); human RBMS2 protein such as a protein consisting of the amino acid sequence represented by SEQ ID NO: 2 (NCBI Reference Sequence: NP_002889.1); and murine RBMS2 protein such as a protein consisting of the amino acid sequence represented by SEQ ID NO: 5 (NCBI Reference Sequence: NP_062685.2). The RBMS2 protein includes, within the scope thereof, a type in which the N-terminal is deleted. Specific examples of the RBMS2 protein of this type include a mouse-derived protein, which is consisting of the amino acid sequence represented by SEQ ID NO: 6 (NCBI Reference Sequence: NP_001034169.1) (whose mRNA is consisting of the nucleotide sequence represented by SEQ ID NO: 7 (NCBI Reference Sequence: NM_001039080.1)).

RBMS2 protein to be detected may have an amino acid mutation such as substitution, deletion, addition and insertion, as long as the RBMS2 protein can have an activity to promote the expression of mRNA having a 3'UTR derived from inflammation promoting factor mRNA (e.g., IL-6 mRNA, COX-2 mRNA, IL-8 mRNA, IL-1β mRNA, TNF-α mRNA, MMP1 mRNA, IL-24 mRNA, c-Myc mRNA) or a protein translated from the mRNA (inflammation promoting factor expression promoting activity). From the viewpoint that the inflammation promoting factor expression promoting activity is less likely to be deteriorated, the type of the mutation is preferably substitution, more preferably conservative substitution.

RBMS2 mRNA which is to be detected may have a nucleotide mutation, such as substitution, deletion, addition and insertion, as long as a protein translated from the mRNA can have an inflammation promoting factor expression promoting activity. The type of the mutation is preferably a mutation by which an amino acid substitution does not occur in a protein translated from the mRNA or a mutation by which a conservative substitution of an amino acid residue can occur.

The presence or absence of an inflammation promoting factor expression promoting activity can be determined by or in accordance with a known method. For example, this presence or absence can be determined by or in accordance with the methods described in the section "Examples". A specific example is as follows: in Example 1B, when an expression vector for a test protein is used as the expression vector, it is determined that the test protein has an inflammation promoting factor expression promoting activity when the luciferase activity is higher than that achieved when an empty vector is used as the expression vector.

A preferred specific example of RBMS2 protein to be detected is at least one protein selected from the group consisting of a protein mentioned in (a) and a protein mentioned in (b):

(a) a protein which is consisting of an amino acid sequence represented by SEQ ID NO: 2, 5 or 6; and (b) a protein which has 85% or more identity to an amino acid sequence represented by SEQ ID NO: 2, 5 or 6 and has an inflammation promoting factor expression promoting activity.

In (b), the degree of identity is more preferably 90% or more, further preferably 95% or more, still further preferably 98% or more.

An example of the protein mentioned in (b) is:

(b') a protein which is consisting of an amino acid sequence having the substitution, deletion, addition or insertion of one or several amino acid residues in an amino acid sequence represented by SEQ ID NO: 2, 5 or 6 and has an inflammation promoting factor expression promoting activity.

In (b'), the wording "several amino acid residues" refers to, for example, 2 to 30 amino acid residues, preferably 2 to 10 amino acid residues, more preferably 2 to 5 amino acid residues, still further preferably 2 or 3 amino acid residues.

A preferred specific example of RBMS2 mRNA which is to be detected is at least one component selected from the group consisting of mRNA mentioned in (c) and mRNA mentioned in (d):

(c) mRNA consisting of a nucleotide sequence represented by SEQ ID NO: 3, 4 or 7; and (d) mRNA which has 85% or more identity to a nucleotide sequence represented by SEQ ID NO: 3, 4 or 7 and encodes a protein having an inflammation promoting factor expression promoting activity.

In (d), the degree of identity is more preferably 90% or more, further preferably 95% or more, still further preferably 98% or more.

An example of the protein mentioned in (d) is:

(d') a protein which is consisting of a nucleotide sequence having the substitution, deletion, addition or insertion of one or several nucleotides in a nucleotide sequence represented by SEQ ID NO: 3, 4 or 7 and has an inflammation promoting factor expression promoting activity.

In (d'), the wording "several nucleotides" refers to, for example, 2 to 500 nucleotides, preferably 2 to 100 nucleotides, more preferably 2 to 50 nucleotides, still further preferably 2 to 10 nucleotides.

The RBMS2 gene expression product detecting agent is not particularly limited, as long as the detection and the quantification of the RBMS2 gene expression product as mentioned above can be achieved. In the case where the RBMS2 gene expression product is a nucleic acid (e.g., RBMS2 mRNA, a nucleic acid derived therefrom (e.g., cDNA)), examples of the RBMS2 gene expression product detecting agent include a primer and a probe. In the case where the RBMS2 gene expression product is a protein, an example of the RBMS2 gene expression product detecting agent is an antibody.

The primer, the probe or the like is not particularly limited, as long as RBMS2 mRNA, a nucleic acid derived therefrom or the like can be recognized selectively (specifically). The wording "recognize (recognizing) selectively (specifically)" as used herein refers to, but is not limited to, the matter that RBMS2 mRNA can be detected specifically in a northern blotting method, the matter that RBMS2 mRNA or a nucleic acid derived therefrom (e.g., cDNA) can be amplified specifically in a RT-PCR method, for example. The primer, the probe or the like may be any one, as long as a person skilled in the art can determine that the above-mentioned detected substance or amplified product is derived from RBMS2 mRNA.

Specific examples of the primer or the probe include at least one substance selected from the group consisting of a polynucleotide mentioned in item (e) and a polynucleotide mentioned in item (f):

(e) a polynucleotide having at least 15 contiguous nucleotides in the nucleotide sequence for RBMS2 mRNA and/or a polynucleotide complementary to the polynucleotide; and (f) a polynucleotide which can hybridize with the nucleotide sequence for RBMS2 mRNA or a nucleotide sequence complementary to the nucleotide sequence for RBMS2 mRNA under stringent conditions and has at least 15 nucleotides.

The term "a complementary polynucleotide" or "a complementary nucleotide sequence (a complementary strand, a negative strand) refers to a polynucleotide or a nucleotide sequence which is complementary to the full length sequence of a polynucleotide consisting of the nucleotide sequence for RBMS2 mRNA or a partial sequence of the full length sequence which has a nucleotide sequence consisting of at least 15 contiguous nucleotides in the above-mentioned nucleotide sequence (wherein each of the full length sequence and the partial sequence is referred to as a "positive strand" for convenience) on the basis of the nucleotide base pair relationship of A:T and G:C. In this regard, the complementary strand is not limited to one that can form a completely complementary sequence with the nucleotide sequence for the positive strand, and may also be one which has a complementary relationship with the positive strand of interest to such an extent that the complementary strand can hybridize with the positive strand under stringent conditions. The stringent conditions can be determined on the basis of the melting temperature (Tm) of a nucleic acid to which a complex or a probe is to be bonded, as taught by Berger and Kimmel (1987, Guide to Molecular Cloning Techniques Methods in Enzymology, Vol. 152, Academic Press, San Diego CA). For example, as the washing conditions after hybridization, the conditions around "1×SSC, 0.1% SDS, 37° C." can be mentioned. It is preferred that the complementary strand can be maintained in such a state that the complementary strand is hybridized with the positive strand of interest even when the complementary strand is washed under these conditions. Examples of the washing conditions include, but are not limited to around "0.5×SSC, 0.1% SDS, 42° C." as more stringent hybridization conditions, around "0.1×SSC, 0.1% SDS, 65° C." as still more stringent conditions. Concrete examples of the complementary strand include a strand consisting of a nucleotide sequence completely complementary to the nucleotide sequence for the positive strand of interest, and a strand consisting of a nucleotide sequence having at least 90%, preferably 95%, more preferably 98% or more, further preferably 99% or more identity to the strand.

The primer, the probe or the like can be designed by utilizing a vector NTI (manufactured by Infomax) on the basis of the nucleotide sequence for RBMS2 mRNA, such as a nucleotide sequence represented by SEQ ID NO: 3, 4, or 7. Concretely, the probe or the like can be obtained by applying the nucleotide sequence for RBMS2 mRNA to software of vector NTI. It is also possible to use a candidate sequence for the primer or probe or a sequence containing at least the sequence as a part thereof, as the primer or probe.

The nucleotide length of the primer, probe or the like is not particularly limited, as long as the primer, probe or the like has a length consisting of at least contiguous 15 nucleotides as mentioned above. The length of the primer, probe or the like can be set appropriately depending on the intended use. For example, in the case where it is intended to use as a primer, the nucleotide length is, for example, 15 to 100 nucleotides, preferably 15 to 50 nucleotides, more preferably 15 to 35 nucleotides. In the case where it is intended to use as a probe, the nucleotide length is, for example, 15 nucleotides to total number of nucleotides in the entire sequence, preferably 15 to 1000 nucleotides, more preferably 100 to 1000 nucleotides.

The primer, probe or the like may be modified, as long as the function thereof cannot be impaired significantly. Examples of the modification include the addition of a labeling substance, such as a fluorescent dye, an enzyme, a protein, a radioactive isotope, a chemiluminescent substance and biotin.

As the fluorescent dye to be used in the present invention, one which can label a nucleotide and can be used for the detection or quantification of a nucleic acid can be generally used. Specific examples of the fluorescent dye include, but are not limited to HEX (4,7,2',4',5',7'-hexachloro-6-carboxylfluorescein, a green fluorescent dye), fluorescein, NED (product name, manufactured by Applied Biosystems, a yellow fluorescent dye), 6-FAM (product name, manufactured by Applied Biosystems, a greenish yellow fluorescent dye), and rhodamine and a derivative thereof [e.g., tetramethyl rhodamine (TMR)]. As the method for labeling the nucleotide with a fluorescent dye, a proper method among known labeling methods can be employed [see Nature Biotechnology, 14, 303-308 (1996)]. Alternatively, a commercially available fluorescent labeling kit may also be used (e.g., an oligonucleotide ECL 3'-oligolabeling system, manufactured by Amersham Pharmacia).

The primer may also be immobilized onto an arbitrary solid phase upon use. Therefore, in the diagnostic agent of the present invention, the probe (an oligo- or polynucleotide) can be provided in the form of an immobilized probe (e.g., a DNA chip, a cDNA microarray, an oligo DNA array, a membrane filter or the like, on each of which the probe is immobilized; which are collectively named "a DNA chip or the like", hereinafter).

The solid phase to be used for the immobilization is not particularly limited, as long as an oligo- or polynucleotide can be immobilized thereon. Specific examples of the solid phase include a glass plate, a nylon membrane, microbeads, a silicon chip, a capillary and other substrates. The immobilization of the oligo- or polynucleotide onto the solid phase may be performed by a method in which a previously synthesized oligo- or polynucleotide is applied on a solid phase or by a method in which a desired oligo- or polynucleotide is synthesized on a solid phase. The immobilization method to be employed is well known in the art depending on the type of the probe to be immobilized, such as a method in which a commercially available spotter (manufactured by Amersham) is used in a DNA microarray technique [e.g., in situ synthesis of an oligonucleotide by a photolithographic technique (Affymetrix) or an inkjet technique (Rosetta Inpharmatics)].

The antibody or the like is not particularly limited, as long as the antibody or the like can recognize RBMS2 protein selectively (specifically). The wording "recognize selectively (specifically)" refers to the matter that RBMS2 protein can be detected specifically in, for example, a western blotting method or an ELISA method. The antibody or the like is not limited to the above-mentioned one, and may be any one as long as a person skilled in the art can determine that the substance to be detected is derived from RBMS2 protein.

The antibody includes a polyclonal antibody, a monoclonal antibody, a chimeric antibody, a single-stranded antibody, or a part of the antibody which has an antigen-binding property, such as a Fab fragment and a fragment produced by a Fab expression library. An antibody having an antigen-binding property to a polypeptide generally consisting of at least contiguous 8 amino acid residues, preferably 15 amino acid residues, more preferably 20 amino acid residues, contained in the amino acid sequence for RBMS2 protein can also be included within the scope of the antibody of the present invention.

The method for producing these antibodies is already known, and the antibody of the present invention can be produced by this conventional method (Current protocols in Molecular Biology, Chapter 11.12 to 11.13(2000)). Concretely, in the case where the antibody of the present invention is a polyclonal antibody, the antibody can be obtained by using RBMS2 protein that is expressed in *Escherichia coli* or the like and then purified in the conventional manner, or by synthesizing an oligopeptide having a partial amino acid sequence of the RBMS2 protein in the conventional manner, then immunizing a non-human animal, e.g., a domestic rabbit, with the RBMS2 protein or the oligopeptide and then collecting the antibody from serum from the immunized animal in the conventional manner. On the other hand, in the case where the antibody is a monoclonal antibody, the antibody can be obtained by immunizing a non-human animal, e.g., a mouse, with RBMS2 protein that is expressed in *Escherichia coli* or the like and then purified in the conventional manner or an oligopeptide having a partial amino acid sequence of the RBMS2 protein to produce a spleen cell, then performing cell fusion of the spleen cell to a myeloma cell to prepare a hybridoma cell, and then collecting the antibody from the hybridoma cell (Current protocols in Molecular Biology edit. Ausubel et al. (1987) Publish. John Wiley and Sons. Section 11.4 to 11.11).

The RBMS2 protein to be used as an immunizing antigen in the production of the antibody can be obtained on the basis of known gene sequence information by procedures including the cloning of DNA, the construction of plasmids, the transfection into a host cell, the culture of a transformant and the collection of a protein from a culture. These procedures can be carried out by a method known to a person skilled in the art or a method disclosed in a document (Molecular Cloning, T. Maniatis et al., CSH Laboratory (1983), DNA Cloning, DM. Glover, IRL PRESS (1985)) or the like.

Concretely, a protein that can be used as an immunizing antigen for the production of the antibody of the present invention can be obtained by producing recombinant DNA (expression vector) which enables the expression of a gene encoding RBMS2 to be expressed in a desired host cell, then introducing the recombinant DNA into a host cell to transform the host cell with the recombinant DNA to produce a transformant, then culturing the transformant to produce a culture, and then collecting the desired protein from the culture. Alternatively, a partial peptide of RBMS2 protein can also be produced by a conventional chemical synthesis method (peptide synthesis) in accordance with known gene sequence information.

The antibody of the present invention may be prepared by using an oligopeptide having a partial amino acid sequence of RBMS2 protein. The oligo(poly)peptide to be used for the production of the antibody is not required to have a functional biological activity but desirably has the same immunogenic property as that of RBMS2 protein. An example of the antibody is an oligo(poly)peptide that preferably has the immunogenic property and is consisting of at least 8 contiguous amino acid residues, preferably 15 amino acid residues, more preferably 20 amino acid residues, in the amino acid sequence for the RBMS2 protein.

The production of the antibody against the oligo(poly) peptide can be achieved by enhancing an immunological reaction using any one of various adjuvants depending on a host to be used. Examples of the adjuvant include, but are not limited to Freund's adjuvant; a mineral gel such as aluminum hydroxide; a surface-active substance such as lysolecithin, pluronic polyol, a polyanion, a peptide, an oil emulsifying agent, keyhole limpet hemocyanin and dinitrophenol; and a human adjuvant such as BCG (Bacille Calmette-Guerin) and *Corynebacterium parvum*.

The diagnostic agent of the present invention is not particularly limited, as long as the above-mentioned RBMS2 gene expression product detecting agent is contained. The diagnostic agent may be consisting of only the detection agent, or may additionally contain a substance necessary for the detection of a RBMS2 gene expression product in addition to the detection agent. Specific examples of the substance include a hybridization reagent, a label for a probe, a detection agent for a labeled substance, a buffer solution and a device. The diagnostic agent of the present invention may be in the form of a diagnostic agent kit including the above-mentioned components.

The diseases to be diagnosed with diagnostic agent of the present invention is not particularly limited, as long as a diseases which can be developed or worsened by an inflammation promoting factor (e.g., IL-6 mRNA, COX-2 mRNA, IL-8 mRNA, IL-1β mRNA, TNF-α mRNA, MMP1 mRNA, IL-24 mRNA, c-Myc mRNA). Specific examples of the disease include an immune disease, an inflammatory disease, a painful disease and the like. More specific examples of the disease to be diagnosed include an autoimmune disease, a rheumatic disease, rheumatoid arthritis, a degenerative arthritis disease, arthritis, sepsis, a lymphoproliferative disease, a demyelinating disease in the central nervous system, spondyloarthropathy, inflammatory pain, postoperative pain, allergic disease, preferably an autoimmune disease, rheumatoid arthritis, a lymphoproliferative disease, a demyelinating disease in the central nervous system, postoperative pain and an allergic disease, more preferably rheumatoid arthritis.

Examples of the autoimmune disease in the present application include, but are not limited to Guillain-Barre syndrome, ulcerative colitis, Crohn's disease, Graves' disease, rheumatoid arthritis, systemic lupus erythematosus, polymyositis, scleroderma and Sjogren's syndrome.

Examples of the rheumatic disease in the present application include, but are not limited to rheumatoid arthritis, juvenile idiopathic arthritis, systemic lupus erythematosus, scleroderma, polymyositis, vasculitis syndrome, Behcet's disease, Sjogren's syndrome and psoriatic arthritis.

Examples of the degenerative arthritis disease in the present application include, but are not limited to osteoarthritis of the knee, osteoarthritis of the hip, osteoarthritis of the elbow, osteoarthritis of the shoulder, osteoarthritis of the wrist and osteoarthritis of the foot.

Examples of the lymphoproliferative disease in the present application include, but are not limited to lymphedema, lymphadenitis, malignant lymphoma and Castleman's disease.

Examples of the demyelinating disease in the central nervous system in the present application include, but are not limited to multiple sclerosis, acute disseminated encephalomyelitis and inflammatory diffuse sclerosis.

Examples of the spondyloarthropathy in the present application include, but are not limited to ankylosing spondylitis, reactive arthritis and psoriatic arthritis.

Examples of the inflammatory pain in the present application include, but are not limited to osteoarthritis, low back pain, shoulder periarthritis, cervico-omo-brachial syndrome, flexor tenosynovitis and dental pain.

Examples of the allergic disease in the present application include, but are not limited to an allergic skin disease such as contact dermatitis, eczema, hives, Quincke's edema, erythema nodosum and atopic dermatitis, allergic rhinitis, bronchial asthma, drug allergy and food allergy.

The diagnostic agent of the present invention can be used for the diagnosis about the occurrence of the above-mentioned disease of interest (i.e., whether or not a subject is suffering from the disease) and the diagnosis about the degree of progression of the above-mentioned disease of interest, as mentioned in the sections "2. Method for detection of disease" and "3. Method for determination of degree of progression of disease" below.

2. Method for Detection of Disease

The present invention relates to a method for detecting an immune disease, an inflammatory disease or a painful disease (which is also referred to as the "disease detection method of the present invention" in the description), using the expression amount/level of RBMS2 as an index. Hereinbelow, the method will be described.

As a specific aspect of the disease detection method of the present invention, the following aspect can be mentioned:

(a1) measuring the expression amount/level of interest of a RBMS2 gene expression product in a sample collected from a subject; and (b1) comparing the expression amount/level of interest measured in step (a1) with a control expression amount/level of the RBMS2 gene expression product in a sample collected from a control subject which does not suffer from any one of the immune disease, the inflammatory disease and the painful disease, wherein (c1) the matter that the expression amount/level of interest is higher than the control expression amount/level is employed as an index for the determination that the subject has the immune disease, the inflammatory disease or the painful disease.

The subject is a target to which the disease detection method of the present invention is to be applied, and the species of the subject is not particularly limited. Examples of the subject include various mammals including human, monkey, mouse, rat, dog, cat, rabbit and the like.

The sample is not particularly limited, as long as a RBMS2 gene expression product is contained. The sample can be selected appropriately depending on the type of the disease to be detected and the like. Specific examples of the sample include a blood sample, a urine sample, and various tissue grafts. As the sample, a sample collected from a living organism may be used without any modification, and a sample produced by purifying and concentrating a RBMS2 gene expression product to be detected in the conventional manner is preferred. In the case where the RBMS2 gene expression product to be detected is a nucleic acid, it is possible to prepare a nucleic acid (e.g., cDNA) that reflects the sequence information of RBMS2 mRNA from the mRNA and use the resultant product as the sample.

The measurement of the expression amount/level of interest and the control expression amount/level of the RBMS2 gene expression product can be carried out by or in accordance with a known method. It is preferred to carry out the measurement using the diagnostic agent of the present invention mentioned below. In the case where the substance to be measured is a nucleic acid (RBMS2 mRNA or a nucleic acid derived therefrom (e.g., cDNA)), the measurement can be carried out by a northern blotting method, a RT-PCR method, a DNA chip analysis method, an in situ hybridization analysis method or the like using the nucleic acid as a probe or a primer, for example. In the case where the substance to be measured is a protein, the measurement can be carried out by a western blotting method, an ELISA method or the like using a specific antibody.

In the case where a northern blotting method is employed, the presence or absence or the amount/level of RBMS2 mRNA or a nucleic acid derived therefrom in a sample can be determined using the diagnostic agent of the present invention as a probe. Concretely, a method can be exemplified, in which the diagnostic agent of the present invention (complementary strand) is labeled with a radioactive isotope (e.g., $^{32}$P, $^{33}$P: RI), a fluorescent substance or the like, then the labeled product is hybridized with mRNA derived from a sample from a subject and transferred onto a nylon membrane or the like in the conventional manner, and then a double strand formed by the diagnostic agent and mRNA derived from the sample from the subject is subjected to the detection and measurement of a signal coming from a labeled product of the diagnostic agent (a labeling substance such as an RI or a fluorescent substance) using a radioactive ray detector BAS-1800II (manufactured by Fujifilm Corporation), a fluorescence detector or the like. Alternatively, a method may also be employed, in which the diagnostic agent is labeled using AlkPhos Direct Labelling and Detection System (manufactured by Amersham Pharmacia Biotech) in accordance with the protocol, then the labeled diagnostic agent is hybridized with mRNA derived from a sample from a subject, and then a signal coming from a labeled product of the diagnostic agent is detected and measured using a multibioimager STORM860 (manufactured by Amersham Pharmacia Biotech).

In the case where a RT-PCR method is employed, the presence or absence or the amount/level of RBMS2 mRNA or a nucleic acid derived therefrom in a sample can be determined by using the diagnostic agent of the present invention as a primer. Concretely, a method can be exemplified, in which cDNA is prepared from RNA derived from a biological tissue of a subject in the conventional manner, then a pair of primers prepared from the diagnostic agent of the present invention (i.e., a positive strand capable of binding to the cDNA (− strand), a negative strand capable of binding to + strand) are hybridized with the cDNA to perform a PCR method so that a target region can be amplified using the cDNA as a template, and then amplified double-stranded DNA thus produced is detected. For the detection of the amplified double-stranded DNA, a method in which the above-mentioned PCR is carried out using a primer that is labeled with an RI or a fluorescent substance in advance to detect labeled double-stranded DNA produced; a method in which double-stranded DNA thus produced is transferred onto a nylon membrane or the like in the conventional manner, then the labeled diagnostic agent is used as a probe and is hybridized with the double-stranded DNA, and then a hybridized product is detected; and other method can be employed. In this regard, a labeled double-stranded DNA product thus produced can be measured using an arrangement 2100 bioanalyzer (manufactured by Yokogawa Analytical Systems, Inc.) or the like. Alternatively, it is also possible to prepare a RT-PCR reaction solution using SYBR Green RT-PCR Reagents (manufactured by Applied Biosystems) in accordance with the protocol, then react the reaction solution using ABI PRISM 7700 Sequence Detection System (manufactured by Applied Biosystems), and then detect a reaction product.

In the case where DNA chip analysis is utilized, a method can be mentioned, in which a DNA chip in which the diagnostic agent of the present invention is attached as a (single-stranded or double-stranded) DNA probe is provided, then the DNA chip is hybridized with cRNA prepared from RNA derived from a biological tissue from a subject in the conventional manner to produce a double-stranded product formed from the DNA and the cRNA, then the double-stranded product is bonded to a labeling probe prepared from the diagnostic agent of the present invention, and then the bonded product is detected.

As the western blotting method, a method can be exemplified, in which the diagnostic agent of the present invention is used as a primary antibody, a labeled antibody (an antibody capable of binding to the primary antibody) that is labeled with a radioactive isotope such as $^{125}$I, a fluorescent substance, an enzyme such as horseradish peroxidase (HRP) or the like is used as a secondary antibody, and a signal coming from the labeling substance, e.g., the radioactive isotope, the fluorescent substance or the like, in the labeled compound is detected using a radioactive ray measurement device BAS-1800II (manufactured by Fujifilm Corporation), a fluorescence detector or the like. Alternatively, it is also possible to use the diagnostic agent of the present invention as a primary antibody, then the signal is detected using ECL Plus Western Blotting Detection System (manufactured by Amersham Pharmacia Biotech) in accordance with the protocol and is then measured using multibioimager STORM860 (manufactured by Amersham Pharmacia Biotech).

The control expression amount/level, which is to be compared with the expression amount/level of interest, may be a control expression amount/level of a single sample. However, it is preferred to employ an average value or a mean value of control expression amount/levels of multiple samples.

The determination whether or not a subject is suffering from an immune disease, an inflammatory disease or a painful disease is carried out by employing the matter that an expression amount/level of interest is larger compared with a control expression amount/level as a criterion. Concretely, for example, the determination can be carried out by employing, as an index, the matter that an expression amount/level of interest is increased by 50% or more, preferably 100% or more, more preferably 200% or more, relative to a control expression amount/level.

3. Method for Determination of Degree of Progression of Disease

The present invention relates to a method for determining the degree of progression of an immune disease, an inflammatory disease or a painful disease employing the expression amount/level of RBMS2 as an index (wherein the method also referred to as "the method for determining the degree of progression of the present invention" in the description). Hereinbelow, the method will be described.

As a specific aspect of the method for determining the degree of progression of the present invention, the following aspect can be mentioned:

(a2) measuring the expression amount/level of interest of a RBMS2 gene expression product in a sample collected from a subject suffering from the immune disease, the inflammatory disease or the painful disease; and (b2) comparing the expression amount/level of interest measured in step (a2) with a control expression amount/level of a RBMS2 gene expression product in a sample collected from a control subject suffer from the immune disease, the inflammatory disease or the painful disease, wherein (c3) the matter that the expression amount/level of interest is larger than the control expression amount/level is employed as an index for the determination that the subject has a higher degree of progression of the immune disease, the inflammatory disease or the painful disease than that of the control subject.

The subject, the sample, the measurement of the expression amount/level of interest and the control expression amount/level, the control expression amount/level to be compared with the expression amount/level of interest, and the like are as described in the section "2. Method for detection of disease" above.

The degree of progression of a disease can be defined as the severity of a condition associated with the expression of an inflammation promoting factor such as IL-6, COX-2, IL-1β, IL-8, TNF-α, MMP1, IL-24 and c-Myc.

The determination as at whether or not the degree of progression of an immune disease, an inflammatory disease or a painful disease in a subject is higher than that in a control subject can be determined by employing, as an index, the matter that the expression amount/level of interest is higher compared with the control expression amount/level. Concretely, the determination can be carried out by employing, as an index, the matter that the expression amount/level of interest is higher compared with the control expression amount/level by 50% or more, preferably 100% or more, more preferably 200% or more.

EXAMPLES

Hereinbelow, the present invention will be described in detail with reference to examples. However, the present invention is not limited to these examples.

Example 1

Identification of RBMS2 as IL-6 Post-Transcriptional Regulatory Factor

Example 1A

For the purpose of discovering an IL-6 post-transcriptional regulatory factor, screening was carried out. The schema is shown in FIG. 1A. Concretely, the following procedures were carried out. First, a reporter vector in which a luciferase ORF and an IL-6 3'UTR (SEQ ID NO: 1) were arranged downstream from a SV40 promoter in this order as observed from the 5' side was produced. The reporter vector and an expression vector for each of various genes were transfected into a HEK293T cell on a 384-well plate using a transfection reagent (Fugene HD, manufactured by Promega Corporation). 48 hours after the transfection, the luciferase activity in each well was measured. A measurement value thus obtained was compared with a measurement value of a control (i.e., a sample in which an empty vector was introduced as an expression vector), and an expression vector of which the measurement value was changed compared with the control was screened (primary screening). About 100 gene expression vectors which was correlated with RNA was picked up from the selected expression vectors, and the screening was carried out in the same manner as mentioned above (secondary screening).

As a result of the secondary screening, RBMS2 (NP_002889.1, SEQ ID NO: 2) was identified as an IL-6 post-transcriptional regulatory factor.

Example 1B

The reporter vector produced in Example 1A or a control reporter vector which was produced by removing a human IL-6 3'UTR from the reporter vector was introduced into a HEK 293 T cell together with a RBMS2 expression vector or an empty vector. 48 hours after the transfection, a luciferase activity was measured. The results are shown in FIG. 1B.

As shown in FIG. 1B, RBMS2 increased a luciferase activity in an IL-6 3'UTR-dependent manner.

Example 1C siRNA for RBMS2 (Human RBMS2-1 (Thermo Fisher Scientific (Ambion), Silencer Select, siRNA ID No. s11867, SEQ ID NO: 8)), or Human RBMS2-2 (Thermo Fisher Scientific (Ambion), Silencer Select, siRNA ID No. s11868, SEQ ID NO: 9), or control siRNA (Negative control (Thermo Fisher Scientific (Ambion), Silencer Select Negative Control No. 1 siRNA, Product number: 4390843)) was introduced into a MDA-MB-231 cell. 48 hours after the introduction, IL-1β was added to a culture medium (final concentration: 20 ng/ml), and the cell was collected 3 hours after the addition. In this regard, a MDA-MB-231 cell can constantly produce IL-6, and can express IL-6 in a larger amount/level upon the stimulation with IL-1β. cDNA was prepared from the cell, and the expression amount/levels of RBMS2 mRNA (PCR primer: Forward: SEQ ID NO: 12, Reverse: SEQ ID NO: 13) and IL-6 mRNA (PCR primer: Forward: SEQ ID NO: 14, Reverse: SEQ ID NO: 15) were measured by quantitative PCR. The results are shown in FIG. 1C.

As shown in FIG. 1C, in a MDA-MB-231 cell, the expression amount/level of IL-6 mRNA was significantly decreased by inhibiting the expression of RBMS2.

Example 1D

The procedure as in Example 1C was carried out, except that IL-1β was added 36 hours after the introduction, a culture supernatant was collected 16 hours after the addition, and the expression amount/level of IL-6 protein in the supernatant was measured by ELISA. The results are shown in FIG. 1D.

As shown in FIG. 1D, in a MDA-MB-231 cell, the expression amount/level of IL-6 protein was decreased significantly by the inhibition of the expression of RBMS2.

Example 1E

A MDA-MB-231 cell was transfected by a retrovirus capable of expressing RBMS2 or a control retrovirus and was then cultured for 1 week in the presence of puromycin to produce a forcibly RBMS2-expressing cell. The cell was stimulated with IL-1β for 3 hours, then the cell was collected, and then cDNA was prepared from the cell. The expression amount/level of IL-6 mRNA in the cell was measured by quantitative PCR. The results are shown in FIG. 1E.

As shown in FIG. 1E, the expression amount/level of IL-6 mRNA was increased by the forcible expression of RBMS2.

Example 1F

A reporter vector in which an ORF of luciferase gene was arranged downstream from a promoter (SEQ ID NO: 36) for IL-6 gene was produced. The reporter vector was transfected together with a RBMS2 expression vector or an empty vector into a MDA-MB-231 cell. 48 hours after the transfection, a luciferase activity was measured. The results are shown in FIG. 1F.

As shown in FIG. 1F, the expression of RBMS2 did not affect the luciferase activity induced by an IL-6 promoter.

Results of Example 1

From the above-mentioned results, it was strongly suggested that RBMS2 regulated the expression of IL-6 positively through the post-transcriptional regulation of IL-6 mRNA rather than the transcriptional regulation of IL-6 mRNA.

Example 2

Stabilization of IL-6 mRNA by RBMS2 via ARE

Example 2A

A RBMS2 expression vector or an empty vector was transfected into a THP-1 cell. 48 hours after the transfection, LPS was added to a culture medium (final concentration: 1 μg/ml) to induce the expression of IL-6 mRNA, and then actinomycin D was added to the culture medium (final concentration: 5 μg/ml) 5 hours after the addition to terminate the synthesis of mRNA. The cells were collected 48 hours after the transfection of the expression vector, 5 hours after the addition of LPS and 3 hours after the addition of actinomycin D, and the amount/level of IL-6 mRNA was measured by quantitative PCR. The results are shown in FIG. 2A.

As shown in FIG. 2A, when an empty vector was transfected, although the expression of IL-6 mRNA was induced by LPS, IL-6 mRNA was decomposed rapidly and the amount/level of IL-6 mRNA was decreased when the transcription was inhibited by the treatment with actinomycin D. In contrast, when RBMS2 was forcibly expressed, IL-6 mRNA remained in a high amount/level after the treatment with actinomycin D. These results suggested that the half-life of IL-6 mRNA was prolonged by RBMS2.

Example 2B

A tetracycline response expression vector in which a luciferase ORF and a IL-6 3'UTR were arranged downstream from a tetracycline response factor (TRE) and a promoter in this order as observed from the 5'-side was produced. The tetracycline response expression vector was transfected together with a RBMS2 expression vector or an empty vector into a HEK293T cell having a Tet-off regulation plasmid integrated therein. 24 hours after the transfection, doxycycline was added to the culture medium (final concentration: 10 μg/ml). 24 hours after the transfection of the vector and 2 hours after the addition of doxycycline, the cell was collected, and the amount/level of luciferase mRNA was measured by quantitative PCR (PCR primer: Forward: SEQ ID NO: 16, Reverse: SEQ ID NO: 17). The results are shown in FIG. 2B.

As shown in FIG. 2B, when an empty vector was introduced, the amount/level of luciferase mRNA containing IL-6 3'UTR was decreased by the addition of doxycycline (the termination of synthesis of mRNA). In contrast, when RBMS2 was forcibly expressed, it was confirmed that a high amount/level of luciferase mRNA containing IL-6 3'UTR remained after the addition of doxycycline. From these results, it was suggested that the half-life of luciferase mRNA containing IL-6 3'UTR was prolonged by RBMS2.

Example 2C

A mutant 3'UTR reporter vector in which a luciferase ORF and a mutant 3'UTR of IL-6 (97-267 (nucleotide sequence: SEQ ID NO: 37), 122-193 (nucleotide sequence: SEQ ID NO: 38), ΔARE1 (nucleotide sequence: SEQ ID NO: 39), ΔARE2 (nucleotide sequence: SEQ ID NO: 40) or an ARE mutant (nucleotide sequence: SEQ ID NO: 41)) were arranged downstream from a promoter in this order as observed from the 5' region was produced. The mutant 3'UTR reporter vector was transfected into a HEK293T cell together with a RBMS2 expression vector or an empty vector. 48 hours after the transfection, a luciferase activity was measured. The results are shown in FIG. 2C.

In a 3'UTR in IL-6 mRNA, there are a stem loop structure involved in the stabilization of mRNA and an AU-rich element (ARE) that is rich in AU. The stem loop structure is an element critical for the recognition by Regnase-1 (ZC3H12A) that is an RNase and the subsequent degradation. It is reported that ARID5a contributes to the stabilization of IL-6 mRNA by antagonizing the function of Regnase-1. However, as shown in FIG. 2C, RBMS2 increased the activity of a reporter (97-267 and 122-193) in which the stem loop structure was deleted in a 3'UTR.

In IL-6 mRNA, there are two adjacent AREs that are close to each other. It is known that an ARE binding protein, e.g. TTP, is involved in the degradation of mRNA through this area. As shown in FIG. 2C, when one of the ARE regions is deleted, the increase in the reporter activity caused by RBMS2 was not observed (ΔARE1 and ΔARE2). When the sequence for ARE was mutated (by substituting U by G), the increase in the reporter activity by RBMS2 was not observed, either (ARE mutant). From these results, it was suggested that RBMS2 was involved in the stabilization of mRNA through the ARE regions.

Results of Example 2

From the above-mentioned results, it was strongly suggested that RBMS2 regulated the expression of IL-6 at a post-transcriptional amount/level through a mRNA stabilization mechanism through the ARE regions.

Example 3

Binding of RBMS2 to IL-6 mRNA through ARE

Example 3A

The reporter vector produced in Example 1A (wild-type 3'UTR of IL-6 downstream from a luciferase ORF) or the ARE mutant 3'UTR reporter vector produced in Example 2C (an ARE mutant) was transfected into a HEK293T cell together with a RBMS2 expression vector labeled with FLAG. 48 hours after the introduction, the cell was collected to prepare a cell lysate. The cell lysate was immunoprecipitated with an anti-FLAG antibody or a non-specific IgG, and the amount/level of luciferase mRNA contained in an immunoprecipitation product was measured by quantitative PCR. The results are shown in FIG. 3A.

As shown in FIG. 3A, as the result of the immunoprecipitation with an anti-FLAG antibody, extreme concentration of luciferase mRNA containing a wild-type 3'UTR of IL-6 was observed. In contrast, luciferase mRNA containing ARE mutant 3'UTR was not concentrated. From these results, it was suggested that RBMS2 was bonded through an ARE.

Example 3B

The reporter vector produced in Example 1A (a wild-type 3'UTR of IL-6 downstream from a luciferase ORF) was transfected into a HEK293T cell together with an expression vector for FLAG-tagged wild-type RBMS2 or RRM1 domain-deleted RBMS2 (amino acid sequence: SEQ ID NO: 46). 48 hours after the transfection, the cell was collected to prepare a cell lysate. The cell lysate was immunoprecipitated with an anti-FLAG antibody or a non-specific IgG, and the amount/level of luciferase mRNA contained in the immunoprecipitation product was measured by quantitative PCR. The results are shown in FIG. 3B.

As shown in FIG. 3B, even when a RRM1 domain-deleted mutant of RBMS2 was overexpressed, the concentration of RNA was not observed. From this result, it was suggested that a RRM1 domain was critical for the binding to an ARE.

Example 3C

The reporter vector produced in Example 1A (a wild-type 3'UTR of IL-6 downstream from a luciferase ORF) was transfected into a HEK 293 T cell together with an expression vector for FLAG-tagged wild-type RBMS2 or RRM domain-deleted RBMS2 (RBMS2 ΔRRM1 (amino acid sequence: SEQ ID NO: 46), RBMS2 ΔRRM2 (amino acid sequence: SEQ ID NO: 47), or RBMS2 ΔRRM1/2 (amino acid sequence: SEQ ID NO: 48)) or an empty vector. 48 hours after the introduction, a luciferase activity was measured. The results are shown in FIG. 3C.

As shown in FIG. 3C, in a RRM1 domain-deleted RBMS2 mutant, the IL-6 3'UTR-dependent increase in luciferase activity was not observed.

Results of Example 3

As mentioned above, it was suggested that RBMS2 enhanced the expression of IL-6 through the binding to an ARE occurring in a 3'UTR of IL-6 mRNA through a RRM1 domain.

Example 4

Regulation of Expression of ARE-Containing Gene by RBMS2

Example 4A siRNA for RBMS2 (Human RBMS2-1 (Thermo Fisher Scientific (Ambion), Silencer Select, siRNA ID No. s11867, SEQ ID NO: 8)), or Human RBMS2-2 (Thermo Fisher Scientific (Ambion), Silencer Select, siRNA ID No. s11868, SEQ ID NO: 9), or control siRNA (Negative control (Thermo Fisher Scientific (Ambion), Silencer Select Negative Control No. 1 siRNA, Product number: 4390843)) was introduced into a MDA-MB-231 cell. 48 hours after the introduction, IL-1β was added to the culture medium (final concentration: 20 ng/ml), and then the cell was collected 3 hours after the addition. cDNA was prepared from the cell, and the expression amount/levels of RBMS2 mRNA (PCR primer: Forward: SEQ ID NO: 12, Reverse: SEQ ID NO: 13), IL-6 mRNA (PCR primer: Forward: SEQ ID NO: 14, Reverse: SEQ ID NO: 15), PTGS2(COX-2) mRNA (PCR primer: Forward: SEQ ID NO: 20, Reverse: SEQ ID NO: 21), IL-8 mRNA (PCR primer: Forward: SEQ ID NO: 22, Reverse: SEQ ID NO: 23), IL-1β mRNA (PCR primer: Forward: SEQ ID NO: 18, Reverse: SEQ ID NO: 19), NFKBIA mRNA (PCR primer: Forward: SEQ ID NO: 24, Reverse: SEQ ID NO: 25) and ZC3H12A mRNA (PCR primer: Forward: SEQ ID NO: 26, Reverse: SEQ ID NO: 27) were measured by quantitative PCR. The results are shown in FIG. 4A.

As shown in FIG. 4A, in a MDA-MB-231 cell, the expression of IL-1β, IL-8 and COX-2 each having an ARE region in a 3'UTR was suppressed by the inhibition of the expression of RBMS2. In contrast, no difference in expression was observed between NFKBIA and ZC3H12A each having no ARE in a 3'-UTR thereof.

Example 4B siRNA for RBMS2 (Mouse RBMS2-1 (Thermo Fisher Scientific (Ambion), Silencer Select, siRNA ID No. s80716, SEQ ID NO: 10), or Mouse RBMS2-2 (Thermo Fisher Scientific (Ambion), Silencer Select, siRNA ID No. s80717, SEQ ID NO: 11)), or control siRNA (Negative control (Thermo Fisher Scientific (Ambion), Silencer Select Negative Control No. 1 siRNA, Product number: 4390843)) was introduced into a MEF cell. 48 hours after the introduction, LPS, Pam3CSK4 or IL-1β was added to a culture medium (final concentration of LPS: 1 µg/ml, final concentration of Pam3CSK4: 1 µg/ml, or final concentration of IL-1β: 20 ng/ml), and then the cell was collected 3 hours after the addition. cDNA was prepared from the cell, and the expression amount/levels of RBMS2 mRNA (PCR primer: Forward: SEQ ID NO: 28, Reverse: SEQ ID NO: 29), IL-6 mRNA (PCR primer: Forward: SEQ ID NO: 30, Reverse: SEQ ID NO: 31), IL-1β mRNA (PCR primer: Forward: SEQ ID NO: 32, Reverse: SEQ ID NO: 33) and TNF-α mRNA (PCR primer: Forward: SEQ ID NO: 34, Reverse: SEQ ID NO: 35) were measured by quantitative PCR. The results are shown in FIG. 4B.

As shown in FIG. 4B, in a mouse embryonic fibroblast (MEF), the increase in expression of TNF-α, IL-1β and IL-6 caused by the stimulation with LPS, Pam3CSK4 or IL-1β was suppressed by the inhibition of the expression of RBMS2.

Example 4C

A reporter vector in which a luciferase ORF, a 3'UTR (a wild-type 3'UTR of IL-8 (nucleotide sequence: SEQ ID NO: 42), an ARE mutant 3'UTR of IL-8 (nucleotide sequence: SEQ ID NO: 43), a wild-type 3'UTR of IL-1β (nucleotide sequence: SEQ ID NO: 44) and an ARE mutant 3'UTR of IL-1β (nucleotide sequence: SEQ ID NO: 45)) were arranged downstream from a promoter in this order as observed from the 5'-side was produced. The reporter vector thus produced, the reporter vector produced in Example 1A (a wild-type 3'UTR of IL-6 downstream from a luciferase ORF), or the IL-6 ARE mutant 3'UTR reporter vector (ARE mutant) produced in Example 2C was transfected into a HEK293T cell together with a RBMS2 expression vector or an empty vector. 48 hours after the introduction, a luciferase activity was measured. The results are shown in FIG. 4C.

As shown in FIG. 4C, when a mutation was caused in an ARE contained in a 3'UTR of IL-6, IL-8, IL-1β or the like, the increase in luciferase activity caused by RBMS2 was not observed.

Results of Example 4

From the above-mentioned results, it was demonstrated that RBMS2 was involved in not only the regulation of IL-6 mRNA but also the regulation of mRNA having an ARE. It was also demonstrated that the expression amount/level of an inflammation promoting factor such as IL-6 mRNA was able to be decreased by inhibiting RBMS2.

Example 5

Decrease in Expression of Inflammatory Cytokine in RBMS2-Deficient Mouse

Example 5A

A RBMS2-deficient mouse was produced by genome editing using TALEN. As a result, a mutant mouse from which 110 nucleotides including the second exon were deleted was produced successfully. The production scheme is illustrated in FIG. 5A.

Example 5B

A cell obtained from bone marrow of a RBMS2 homozygously deficient mouse, a RBMS2 heterozygously deficient mouse or a wild-type mouse was cultured for 7 days in the presence of M-CSF to produce a bone marrow-derived macrophage (BMDM). LPS (final concentration: 100 ng/ml), Pam3CSK4 (final concentration: 300 ng/ml) or poly I:C (final concentration: 10 µg/ml) was added to a culture medium of the BMDM. The cells were collected before the addition or 1 hour, 3 hours, 5 hours or 9 hours after the addition, and the expression amount/level of IL-6 was measured by quantitative PCR. The results are shown in FIG. 5B.

As shown in FIG. 5B, the expression of IL-6 induced by the stimulation with Pam3CSK4 was significantly decreased in a RBMS2-deficient mouse.

Example 5C

The same procedure as in Example 5B was carried out, except that Pam3CSK4 was added to a BMDM culture medium and the expression amount/levels of IL-1β, COX-2 and TNF-α were measured.

As shown in FIG. 5C, the same results as in Example 5B were obtained with respect to a gene other than IL-6.

Example 6

Resistance of RBMS2-Deficient Mouse to Sepsis

LPS (15 mg/kg) was administered intraperitoneally to each of PBMS2 homozygously deficient mice (n=7) or wild-type mice (n=5). 5 hours after the administration, serum was collected, and the survival time of each mouse was measured. The concentration of IL-6 in the serum was measured by quantitative PCR. The results of the measurement of the survival time are shown in FIG. 6A, and the results of the measurement of the concentration of IL-6 are shown in FIG. 6B.

As shown in FIGS. 6A and 6B, 60% or more of the wild-type mice were dead within 81 hours after the intraperitoneal administration of LPS, while 80% or more of the RBMS2 knockout mice survived because the expression level of IL-6 that was an inflammation promoting factor was reduced. From these results, it was demonstrated that RBMS2 was involved in the worsening of inflammatory responses in vivo.

Example 7

Correlation Between Expression Amount/Level of RBMS2 and Expression Amount/Level of IL-6 in Rheumatoid Arthritis Patient RNA was reverse-transcribed from a peripheral blood mononuclear cell from each of rheumatoid arthritis patients (n=12), and then the expression amount/levels of RBMS2 and IL-6 were measured by quantitative PCR. The results are shown in FIG. 7.

As shown in FIG. 7, the expression of RBMS2 and the expression of IL-6 were positively correlated with each other in peripheral blood mononuclear cells collected from rheumatoid arthritis patients.

With taking the fact that the expression amount/level of IL-6 in a non-rheumatoid arthritis patient was lower than that in a rheumatoid arthritis patient and the fact that the expression amount/level of IL-6 in a rheumatoid arthritis patient correlated with the degree of progression of the disease into consideration, these results suggested that it was possible to diagnose rheumatoid arthritis (with respect to the occurrence of the disease, the degree of progression of the disease) employing the expression amount/level of RBMS2 as an index.

Example 8

Search for Factor Capable of Regulating Expression of RBMS2

IL-10 protein or TGFβ protein was added to a culture medium of a Jurkat cell that was a human T cell strain (final concentration: IL-10 protein→20 ng/mL, TGFβ protein→10 ng/mL). cDNA from the cell before the addition and 8 hours after the addition and 24 hours after the addition was prepared, and the expression amount/levels of RBMS2 mRNA and HPRT (control) mRNA were measured by quantitative PCR. The results are shown in FIG. 8.

As shown in FIG. 8, the expression amount/level of RBMS2 mRNA was decreased by the addition of IL-10 protein. This result demonstrated that IL-10 protein had an effect to inhibit the expression of RBMS2.

Example 9

Comparison of Activity to Regulate Expression of ARE-Containing Gene

From the results of Example 4C, it was demonstrated that the activity of RBMS2 depended on an AU-rich element (ARE) rather than a stem loop structure in IL-6 3'UTR. On the other hand, it has been reported that HuR can positively regulate the expression of an inflammatory cytokine through an ARE, and therefore it has been believed that the role of HuR is similar to that of RBMS2. Then, the activities of RBMS2 and HuR were compared with each other by a luciferase assay.

Concretely, a reporter vector in which a luciferase ORF and an IL-6 3'UTR or PTGS2 (COX-2) 3'UTR were arranged downstream from a promoter in this order as observed from the 5'-region was produced. The reporter vector was transfected into a HEK293T cell together with a RBMS2 expression vector, a HuR expression vector or an empty vector. 48 hours after the transfection, a luciferase activity was measured. The results are shown in FIG. 9.

As a result, it was demonstrated that, when an IL-6 3'UTR was used, the luciferase activity was enhanced by RBMS2, while that types of enhancement was not observed when HuR was used. When a PTGS2 (COX-2) 3'UTR, on which it has been reported that HuR can act, was used, although the enhancement of the luciferase activity was observed by HuR, it was found that RBMS2 enhanced the activity more strongly compared with HuR. These results strongly suggested that RBMS2 targeted different mRNA from mRNA targeted by HuR and had stronger activity against the same target mRNA than HuR.

Example 10

Binding of RBMS2 to ARE through RRM1 Domain Example 10A

Heretofore, it has been reported that a β-sheet in a RRM domain is essential for a RNA binding activity and an aromatic amino acid is necessary for the formation of the β-sheet. Then, a protein β-sheet in a RRM1 domain was estimated using a secondary structure estimation program, and an expression vector for a mutant of the β-sheet in which an amino acid was mutated. The expression vector or an empty vector was trasfected into a MDA-MB-231 cell together with the reporter vector produced in Example 1A (a wild-type 3'UTR of IL-6 downstream from a luciferase ORF). 48 hours after the transfection, a luciferase activity was measured. The results are shown in FIG. 10A.

As a result, it was demonstrated that two phenylalanine residues (F101 and F104) in a RRM1 domain were required for the enhancement of a reporter activity by RBMS2.

Example 10B

A lentivirus capable of expression a F101/F104A mutant was transfected into a MDA-MB-231 cell, cDNA was prepared from the cell after 5 days, and the expression amount/levels of IL-6 mRNA and IL-8 mRNA were measured by quantitative PCR. The results are shown in FIG. 10B.

As shown in FIG. 10B, even when the F101/F104A mutant was overexpressed, the expression amount/levels of endogenous IL-6 and IL-8 could not be improved.

Example 10C

The reporter vector produced in Example 1A (a wild-type 3'UTR of IL-6 downstream from a luciferase ORF) was transfected into a HEK 293 T cell together with an expression vector for a FLAG-tagged F101/F104A mutant. 48 hours after the transfection, the cell was collected to prepare a cell lysate. The cell lysate was immunoprecipitated with an anti-FLAG antibody or a non-specific IgG, and the amount/level of luciferase mRNA contained in the immunoprecipitation product was measured by quantitative PCR. The results are shown in FIG. 10C.

As shown in FIG. 10C, the binding to an IL-6 3'UTR was significantly impaired by double mutation in F101A and F104A.

Example 11

A 2,4-dinitrofluorobenzene solution (wherein a solvent was a mixed solution of acetone and olive oil (acetone 4: olive oil 1)) was applied onto an abdominal part of each of RBMS2 homozygously deficient mice (n=15). After 1 week, a 2,4-dinitrofluorobenzene solution (wherein a solvent was a mixed solution of acetone and olive oil (acetone 4: olive oil 1)) or only the mixed solvent was applied onto an ear of each of the mice. After 6 hours, the thickness of the auricle was measured, and a value obtained by subtracting the thickness of the auricle before the test from the measured value was employed as an index for the swelling of the auricle. The results are shown in FIG. 11.

As shown in FIG. 11, the degree of swelling of the auricle in a RBMS2 homozygously deficient mouse was smaller. This result suggested that RBMS2 was involved in an allergic disease such as contact dermatitis.

Example 12

A MDA-MB-231 cell was transfected with siRNA for a negative control or RBMS2 (n=3 for each). After 48 hours, RNA was prepared, an RNA sequencing library was prepared in accordance with a protocol (Illumina, Inc.), and RNA sequencing was carried out using Next-seq. Genes each of which the expression amount/level increased two-fold or more or decreased two-fold or more by the knock-down of RBMS2 are shown in FIG. 12.

As shown in FIG. 12, it was demonstrated that the expression amount/level of mRNA having an ARE in a 3' UTR thereof, such as IL-6, IL-8, MMP 1, c-myc and IL-24 mRNA, was decreased by the knockdown of RBMS2.

As demonstrated in Examples 1 to 12 above, RBMS2 regulated the expression of IL-6 as well as the expression of other inflammation promoting factors (genes each having an ARE in a 3' UTR thereof, such as IL-1β, IL-8, COX-2, TNF-α, MMP1, IL-24 and c-Myc). Therefore, it was suggested that it became possible to diagnose the occurrence and the degree of progression of a disease of which the development and progression was associated with any one of these inflammation promoting factors (e.g., an immune disease, an inflammatory disease, a painful disease) by employing the expression amount/level of RBMS2 as an index.

The invention claimed is:

1. A method for inhibiting the expression of an inflammation promoting factor comprising administering at least one RBMS2 expression inhibitor and/or at least one RBMS2 function inhibitor to a patient in need of inhibition of the expression of an inflammation promoting factor, wherein the inflammation promoting factor is selected from the group consisting of IL-6, COX-2, IL-8, IL-1B, MMP1, and IL-24; and wherein the at least one RBMS2 expression inhibitor and/or the at least one RBMS2 function inhibitor is selected from the group consisting of a RBMS2-specific siRNA, a RBMS2-specific antisense nucleic acid, and expression vectors thereof.

2. The method according to claim 1, wherein the patient has at least one disease selected from the group consisting of immune diseases and inflammatory diseases.

* * * * *

UNITED STATES PATENT AND TRADEMARK OFFICE
CERTIFICATE OF CORRECTION

PATENT NO. : 12,066,429 B2
APPLICATION NO. : 16/913376
DATED : August 20, 2024
INVENTOR(S) : Hiroshi Asahara, Tomoki Chiba and Kentaro Abe Page 1 of 1

It is certified that error appears in the above-identified patent and that said Letters Patent is hereby corrected as shown below:

In the Claims

Column 89, Line 64 in Claim 1, "IL-1B" should read --IL-1β--

Signed and Sealed this
Twenty-second Day of October, 2024

Katherine Kelly Vidal
*Director of the United States Patent and Trademark Office*

SEQUENCE LISTING

```
<160> NUMBER OF SEQ ID NOS: 50

<210> SEQ ID NO 1
<211> LENGTH: 446
<212> TYPE: DNA
<213> ORGANISM: Homo sapiens

<400> SEQUENCE: 1
catgggcacc tcagattgtt gttgttaatg ggcattcctt cttctggtca gaaacctgtc     60
cactgggcac agaacttatg ttgttctcta tggagaacta aaagtatgag cgttaggaca    120
ctattttaat tattttaat ttattaatat ttaaatatgt gaagctgagt taatttatgt    180
aagtcatatt tatattttta agaagtacca cttgaaacat tttatgtatt agttttgaaa    240
taataatgga aagtggctat gcagtttgaa tatcctttgt ttcagagcca gatcatttct    300
tggaaagtgt aggcttacct caaataaatg gctaacttat acatattttt aaagaaatat    360
ttatattgta tttatataat gtaaaatgg tttttatacc aataaatggc attttaaaaa    420
attcagcaaa aaaaaaaaaa aaaaaa                                         446

<210> SEQ ID NO 2
<211> LENGTH: 407
<212> TYPE: PRT
<213> ORGANISM: Homo sapiens

<400> SEQUENCE: 2

Met Leu Leu Ser Val Thr Ser Arg Pro Gly Ile Ser Thr Phe Gly Tyr
1               5                   10                  15

Asn Arg Asn Asn Lys Lys Pro Tyr Val Ser Leu Ala Gln Gln Met Ala
            20                  25                  30

Pro Pro Ser Pro Ser Asn Ser Thr Pro Asn Ser Ser Ser Gly Ser Asn
        35                  40                  45

Gly Asn Asp Gln Leu Ser Lys Thr Asn Leu Tyr Ile Arg Gly Leu Gln
    50                  55                  60

Pro Gly Thr Thr Asp Gln Asp Leu Val Lys Leu Cys Gln Pro Tyr Gly
65                  70                  75                  80

Lys Ile Val Ser Thr Lys Ala Ile Leu Asp Lys Thr Thr Asn Lys Cys
                85                  90                  95

Lys Gly Tyr Gly Phe Val Asp Phe Asp Ser Pro Ser Ala Ala Gln Lys
            100                 105                 110

Ala Val Thr Ala Leu Lys Ala Ser Gly Val Gln Ala Gln Met Ala Lys
        115                 120                 125

Gln Gln Glu Gln Asp Pro Thr Asn Leu Tyr Ile Ser Asn Leu Pro Leu
    130                 135                 140

Ser Met Asp Glu Gln Glu Leu Glu Gly Met Leu Lys Pro Phe Gly Gln
145                 150                 155                 160

Val Ile Ser Thr Arg Ile Leu Arg Asp Thr Ser Gly Thr Ser Arg Gly
                165                 170                 175

Val Gly Phe Ala Arg Met Glu Ser Thr Glu Lys Cys Glu Ala Ile Ile
```

```
            180                 185                 190
Thr His Phe Asn Gly Lys Tyr Ile Lys Thr Pro Pro Gly Val Pro Ala
            195                 200                 205
Pro Ser Asp Pro Leu Leu Cys Lys Phe Ala Asp Gly Gly Pro Lys Lys
            210                 215                 220
Arg Gln Asn Gln Gly Lys Phe Val Gln Asn Gly Arg Ala Trp Pro Arg
225                 230                 235                 240
Asn Ala Asp Met Gly Val Met Ala Leu Thr Tyr Asp Pro Thr Thr Ala
                245                 250                 255
Leu Gln Asn Gly Phe Tyr Pro Ala Pro Tyr Asn Ile Thr Pro Asn Arg
            260                 265                 270
Met Leu Ala Gln Ser Ala Leu Ser Pro Tyr Leu Ser Ser Pro Val Ser
            275                 280                 285
Ser Tyr Gln Arg Val Thr Gln Thr Ser Pro Leu Gln Val Pro Asn Pro
            290                 295                 300
Ser Trp Met His His His Ser Tyr Leu Met Gln Pro Ser Gly Ser Val
305                 310                 315                 320
Leu Thr Pro Gly Met Asp His Pro Ile Ser Leu Gln Pro Ala Ser Met
                325                 330                 335
Met Gly Pro Leu Thr Gln Gln Leu Gly His Leu Ser Leu Ser Ser Thr
            340                 345                 350
Gly Thr Tyr Met Pro Thr Ala Ala Ala Met Gln Gly Ala Tyr Ile Ser
            355                 360                 365
Gln Tyr Thr Pro Val Pro Ser Ser Ser Val Ser Val Glu Glu Ser Ser
            370                 375                 380
Gly Gln Gln Asn Gln Val Ala Val Asp Ala Pro Ser Glu His Gly Val
385                 390                 395                 400
Tyr Ser Phe Gln Phe Asn Lys
            405

<210> SEQ ID NO 3
<211> LENGTH: 8504
<212> TYPE: DNA
<213> ORGANISM: Homo sapiens

<400> SEQUENCE: 3
gagctcattc tctgcccgca gccccccttc atctctctcc tcctgctcct tttctcctcc    60
tttctcctcc ccctcccttt tttcctccct ccctctcccc ctttccctcg ctccctcct   120
ccctccctcc ccgtctttct taccccctcc ctttctctct ctctctctct ctcgctcgtt   180
ccctaacatt aaagagaaaa tgctgctatc cgtgacttcc aggcccggga tttcgacttt   240
tggctacaat agaaacaaca agaagccata tgtgtcattg gctcagcaga tggcaccacc   300
tagcccaagc aacagtacac ctaacagcag tagtggaagc aatggaaatg accagctgag   360
caaaaccaac ctatacatcc gaggattgca accaggcact actgaccaag atcttgtcaa   420
gctgtgtcag ccatatggca aagattgttt cactaaggcc atactggaca agaccacaaa   480
caaatgtaaa ggctatggct ttgtagattt tgacagccct tcagcagcac agaaagctgt   540
aacagcactg aaggccagcg gtgtacaggc acagatggca aagcaacagg acaggaccc   600
cacaaattta tacatctcaa acctcccact gtcaatggat gagcaggaac tggaggggat   660
gctgaagccc tttggccagg ttatctccac ccgtatcctt cgagatacca gtgggaccag   720
cagaggtgtt ggctttgcaa ggatggagtc cacagagaag tgtgaagcca tcatcaccca   780
ctttaatgga aaatatatta agacaccccc tggagtacca gccccatccg atcccttgct   840
```

```
ttgcaaattt gctgatggcg ggccaaagaa acgacagaac caaggaaaat ttgtgcaaaa    900
tggacgggct tggccaagga atgcagacat gggcgtcatg gccttgacct atgacccac     960
cacagctctt cagaatgggt tttacccagc cccctataac atcaccccca acaggatgct   1020
tgctcagtct gcactctccc catacctttc ctctcctgtg tcttcgtatc agagagtgac   1080
tcagacatct cctctacaag tacctaaccc atcctggatg caccaccatt catacctcat   1140
gcagccttca ggttcagttc tgacaccagg gatggaccat cccatttctc tccagcctgc   1200
ctccatgatg ggacccctta cccagcaact gggccatctc tccctcagca gcacaggcac   1260
gtatatgccg acggctgcag ctatgcaagg agcttacatc tcccagtaca cccctgtgcc   1320
ttcttccagt gtttcagtcg aggagagcag cggccaacag aaccaagtgg cagtggacgc   1380
accctcagag catggggtct attctttcca gttcaacaag taacagtggg attcccctcc   1440
ccatctttac tgaatagaaa tgaattcttg agatactca tgctcccaga ttccagaggg    1500
ttaaccagga atggagacca tccgtcggcc ctgctaagga ctaacactta gccatcgttt   1560
ttcacaggcc tgggcctgga aaaagaaatc tctacgttcc tgccctttac tattgctgat   1620
ggagcctggg ggaaccatca cttttttttgt gtgctacatt caaggagatc aaaaaaactt   1680
ttcttctttt gcaaagaaag cttttgtttt ttaactgcaa cgtacttttc ccctaccttg   1740
aagagacatg gtggtcgcag cttctcatct atatgaaaaa gttttcgatg tattggaatt   1800
atttgggaat gcttttaaaa caatttgtaa ttatttcttt acaaaccaaa acagaacaga   1860
aaggtgtggt gctggaacat cgatgaagga gccctactta ctgagcttag ttatggactt   1920
ttttgatgca tgtgtgtatg tgttttaaaa agtatgcagg ctctaaaaat gttatttttgt   1980
aaagctctca gctcatgcac cccatctcct cttcacccat attatgcctt ctttctcttg   2040
tccagattct tcttttttctc ttttctaaac agctgagcct gcctactttg ccctttaca   2100
gcttttaatt ttatggattt ttaaaaatga aatttcatgt ggaatttggg gttgggggc    2160
aggctgggca aggaacaagg cagaaacacta agtaggccat ggaagtggct gttctttccc   2220
ccaccctgcc acaccctggg agaaaaaact agactttggc ttcagaaagc acagatgtga   2280
cccaggctta ctaaagagac aactccacag ccctgggaac acaccttga gccaaacttg    2340
gttgaagact aggtcttccc tggcaagttc cggaagaatg gacttactga cttttatcaa   2400
ctcttctcac tgccaaggcc aacagcatct gaggtatagc ttttttgggag tacctgcttt   2460
cttgcctcct ggaggatatt ttctgtcctg ggcttcatgg cccctctctt ccctgttaca   2520
cattgctgtg ctcagagcct ttgcagctgc gacctagttg aatccacata ggctccttcc   2580
acacggtgga agatctgctg cttcactcac agaccaggag ttctcaatca gaggtggttt   2640
tgtccctcag gcctttggca acatctagag acagttttga ttgccacgcc tggaggtggg   2700
atgtgtgtgc tactggcatc tagtggctgc taaacatcct acactgcata ggatagtccc   2760
cactacccc agccaagaat tatctgactc caggggtcaa tattgccaag actgggaaac    2820
actgatatag acagtgttgt ccctgcctcc tgggttaggg taaattttca ccccaaccct   2880
ggacaaacag tgccttttga cactcatgca actgttgggg aaggactgga ctgggatcct   2940
tgaattctcc ccagactttg acttttgata actctgcata tagcaagagt gattcttgaa   3000
agagctgtgg ctccatgctg aatgcacaca tgtactcaga gggattcagg tgggcattgt   3060
tctggtgtgt gctgtgcaat ggtgggaaag gacaaagctc tctaaactgt ccagagcaac   3120
ctgccctgcc ccggtgtgct tggacccttt gcccagggaa ccaggacatc agaaataatg   3180
```

```
ttccttctgt ggaaggacaa cggggagcta gggtagcaaa gagcaataaa ttccaactct    3240
ttatgaggtc aggagtcctt taaaaaagcc tatgtcttgg tctttaactg tccccttctg    3300
caagatgtga ctctatacac atggagacag attgaagaaa gacttcaccc atcttctagg    3360
aaataaaatc ctgctcttgt cttctcccag tcactccctt atgcactgaa aggagaattt    3420
gactcccttg cacttcaagg ccaggtgcct ctccactaga cagtcagaca aaggcaaata    3480
atggaggata gagagacagg tgttcattag gctggccata gggagaggaa ggggtgaca    3540 gcagggaaa agaaactgta gtatcagttg tcacaagtag agctcggccc agctttccct    3600
cccttcccag ccaccctaga attgagagtc ccagtgcccc tagtgtcgac tttctatgta    3660
catcctaggg gtgagggagt gcgggcaat gggtaggata taaagcgtaa aggacaaatt    3720
gccgcagtct tctaattgat gcttccaaac tcaggaaggg cttatccagt gtaaaatagc    3780
cccaagccca gcaaccttct agagggctct ggctgggcag atagcttttg ttttgagtc    3840 tccagccctc agtcaaggaa aatataccat agctgctttc ttgtcagtgg cctttgagag    3900
aaagagaaaa caaatctaga attctgttca tctgatagac cggggagct ttgctatggt    3960 aggaggttta ggaagggcct ttcacgcata gaaaccattg ttgatattgc cactcccctc    4020
tcctctgcct cacagaactc ctgattctgt cttcttctc tctctatata tatattttaa    4080 aatgttaaa tggctctaat tttttgtttt gaattttgaa tttacctttt ggagttcttc    4140
tcatgtgaat ctacttgtta gattgtatta atgagtgttt ctggtttggg catgggaagt    4200 gatggggcc tgaagttatt ttgcagtggc taatggcact gaggaatttc ttttttggtg    4260
catttggttt acactcattt cctctcctaa ttgttagttc atttgtaaca gtgggtgagt    4320
gtttggagga aaggagggag aagaaaggag ggatactgtt tctcccatga aatagtctaa    4380
ttggttgggt tgatggcaga aggaaacata ggggagcctt ccagctcaca gccaagggtt    4440
gggctcttaa acactatgcc tagtgttttc tgaatgctgt cttcatggag cccagctctt    4500
actctctttg tactttacat ctcacccca ctcattacag atgctcataa cattcttaaa    4560 atatttagt acttggcatt tttctgtttt cagtcagcta gaacacacta gagtcctttc    4620
ctcagatggc ataatccttt ataggctctg agcctgccta gccatctcct atcggtgtta    4680
ttactcctca tctcaggctc tgagatgata ctcagaccct aaactgattg acttttggg    4740 aggagggtgc cagtagagag gtcaggaaga tgtggagatg atgatggaga gagatgtttt    4800 tatttattt tatttttca gacagagtct tgctctgtcg cccaggctgg agtgcaatgg    4860
cacgatctcg gctcactgca acctccgcct cccaggttca agcaattctc ctgcctcagc    4920
ctcccatgta gctgggatta caggcaccca ccaccatgcc cggctaattt ttttatttt    4980 agtagagatg gggtttcacc atgttggcca ggctggtctc gaactcctga cctcaggtga    5040
tctgcccgcc ttagcctccc aaagtgctgg gattacaggc gtgagccacc gcgcccggcc    5100
tttattttat tttttagaga tggtcttgct gtgtcaccca ggctggagtg cagtgatgca    5160
gtcgtagtct actacagtct tgaattcctg ggcccaaggg ttcttcccac ctaagcctcc    5220
caagtagctg gaagtacagg cacatactac caagcccagt tcgttatttt aagttttgt    5280 agagacaggg gtcttactat gttgcccaga ctggtcttga actcctgtca agtgagcctc    5340
ccacctcagc ctcccaaagt gctatgatta caggtgtgag cctccatgct tggatgagat    5400
gttgttttta atgtttttgg ttttttggtt ttgttgtttt gttttttga gacagggtct    5460 cactctgtgg cccaggctgg agtgcagtgg caccataatg gctcactgca gcctcgacct    5520
cccaaggctc aggtgatcct cttgcctcag ccacccctc cccggccacc aagtagctgg    5580
```

```
gactatgggc ttgtgccacc atgcctggct aattttttta tttttagtag agatgggtt    5640 ttaccacgtt ggccaggcta gtgtccaact cctgacctcc aaacagctaa tttttgtatt    5700
tttaatagag acaggttttc gccatgttgc ccagcctcgt ctcgaactcc tgggctcaaa    5760
tgatccaccc acctcggcct cccaaagtgc tgggattata ggcatgagcc accacacctg    5820
gccttttcag ttttttattt tttattttt ctttgagacg gagtctcgct ctgtcgccca    5880
ggctggagtg cagtggcgtg atcttggctc actgaaacct ccatctcctg ggttcaagca    5940
gttctcctgc ctcagcctcc tgagtagctg ggattacagg tgcctgccac catgcctggc    6000
taatttttgt attttagta gagacagggt tttgccacat gcccaggct ggtgttgaac    6060 tcctgggctc aaatgatcca cctgccttgg cctcccaaag tgctgggatt acaggcgtga    6120
gccactgcac ccggcccttt gtagtgtttt taactaaaga atttgtagag ttgcccaggc    6180
caggaagcct ggtggctcta aagggtaata gaccttgtca gtaacagata aggagtggta    6240
agaggacatt actcatattg aagatgaaga ccagactttg ctgcttcaca ggccatgcgc    6300
tgggttgggc cacttcagct ccactccatt cgttttcctt tcctaacttg acaatcagct    6360
cactcaccct cccttagtgc ctccagtgcc tactcctgtc actccaatgt caacccattg    6420
ggagttgagg cctgtcactc caatgtcaac ccgtgggctg ttactttgcg tcatatgatg    6480
ctgtgagagg ccttgctgga atgtcctagg aatccctagt agcagtggct attagtcttc    6540
tagaaaagaa ctattgctgc tgccttgtgc acatgcccca ccttctgggc aagtggcagc    6600
attgcgctca tgagggcttt gcattctta gccaagggca ataaactggg tgggtgatct    6660
ggcccaaact tgcccctagg ctctgctagc cctgaatcag caggcttcag agacgagggt    6720
gggtgttata aaagccagtc tgtaaagggt aaattccaaa tcttgtgcct tgttatacca    6780
atccttcctg attcccgttt aaaccaacta ctctatttct gtgctgccta cattttcaat    6840
cctcccacgc attagcaaat tcctgaaatt tcctcatttg gtaggccttc cataggagtc    6900
agctatggac ttccatagga gttggcagct aaaaccagac tgtgagcttc tgtctccgtt    6960 ctgattttg ctgcacctcc caggggacag tccccacatg attacaaaag ccaggtgccc    7020
tcatcacccg ttaccctga cctgtccact tgttttgaat aaaccttcat tctccaagca    7080
gatccccaaa cttccttgtc cttgttacac gtctacctca caacctcaca attcaacaac    7140
aggtaaatac ctggattcac tgatttcttt actgtccttc tctgagggtt gggaaggtgg    7200
gggctagaaa aggctcataa ttttaaact cttgggaatt aaacttggga atttctattc    7260
ctacagtgtt ttctctggga ttttagctc actgatcgcc ctagaatagt gtgaactctc    7320
cagataggtc ctgctgtgat aggccagggg agtaggctgt gcagtgacgg cttagggtaa    7380
taagtaatgg ttggaggaca ccagcatagg agcagagttt agaacttaag aggacaagaa    7440
agctgctcag tggctggcgt atagctgtga aggtaaccaa acaccaaaga gggagtctgt    7500 cattttata aggctggaag cgaatgttcc ttttctacct aaacatacag tttaggggt    7560 tgcaccaaga caaagtttcc aggctggagg gtaatacata tccagcgcga gtgaagtccc    7620
cactccaaca tataccttt ttgggtgggt aaacacctct ttgcatgtgg acagaaaatg    7680
tttatactta aacagacata ttttgcatat ttttatctgg agcttcttc tagtttata    7740 ctcttcccac atctatgcca atgccaccat tctaaaactt acactccttt tctacccctg    7800
gtcttttcct tgtccttccc tacaacttgg tagaggtcca ttttgtctta cttcacactt    7860
tttttttttt aaataaaaca caaagtctca cgtcttggtg tcttatccgt gagtgggaag    7920
```

| | |
|---|---|
| tggtaagctg gtgatggtcc catatttgct atgacaggaa cacagaggtg gcagcttagg | 7980 |
| aagctggggc cacatctcac aaggcaggac ctggatgcac tgaatccccc tttgctccag | 8040 |
| caactcagcc agacatttag gcaggagcac taatgaccct ttccatccac acagagggta | 8100 |
| tggaacagga gccctgttg ttcccttgcc tgtggtctct taagccagtc atacctatcc | 8160 |
| caacgccgtc tccccctcag gtgtgtagaa gggaagatga atacacagag tcttttgaat | 8220 |
| ctctatcaaa tgtggttttt tttattcaac aactgacaag cacttttcta cagctgcact | 8280 |
| tgtggaacat cacatggcaa aacaggagt tttttcgcta gacttttttt ttcttttaa | 8340 |
| ccttattaaa aatgagattg gtcctaaaaa tatagaaaga aataaattta aattcacaaa | 8400 |
| aaactgtaca ttatcaaaaa gtcactaaaa caccacattt ggttatataa aaagtccctt | 8460 |
| ttgctgtaaa aggaacacag aaacttaaaa aaaaaaaaaa aaaa | 8504 |

<210> SEQ ID NO 4
<211> LENGTH: 5207
<212> TYPE: DNA
<213> ORGANISM: Mus musculus

<400> SEQUENCE: 4

| | |
|---|---|
| ctttctcctc cccctccctt ctcccttccc tccctctttc cctcccttcc tctctccctc | 60 |
| tcctttcccc ctcccctcct ccctcccctct ttctccctcc ctttccttca ctctcttctt | 120 |
| tctctctctc agctccgtaa cagtaaagaa aaaatgctgc tatcagtgac ttccaggcct | 180 |
| gggatttcga cttttggcta taacaagaac aacaagaagc tatatgtggc tcagcaaatg | 240 |
| gcacctccaa gtccaaggaa tagcaccccc aacagcagcg gcggaggcgg cggcgggagt | 300 |
| ggtgggaacg accagctgag caaaaccaac ctgtatatcc gaggactgca gccaggcacc | 360 |
| actgaccagg accttgtcaa gctctgtcag ccgtatggca agattgtctc cactaaggcc | 420 |
| atcctggaca agaccacaaa caagtgcaaa ggctatggct ttgtggactt cgacagtccg | 480 |
| tcatcagcac agaaagctgt aactgcactg aaagccagtg gtgtgcaggc acaaatggca | 540 |
| aagcaacagg agcaagaccc tacaaactta tacatctcaa acctccctct gtcaatggac | 600 |
| gagcaggaac tggaggggat gctgaagccc tttggccagg tcatctctac tcggatcctt | 660 |
| cgagacacta gtggggccag cagaggggtc ggctttgcaa ggatggagtc aacagagaag | 720 |
| tgtgaagcca tcatcaccca ctttaatgga aagtatataa agacaccccc tggagtagca | 780 |
| gcaccttctg accctttgct ttgcaaattt gctgacggtg ggccaaagaa acgacagagc | 840 |
| caaggaagat acgtgcaaaa tggacgggcc tggccaagga acggagacat gggcggtatg | 900 |
| gccttgacct atgaccccac tgctgccctt cagaatgggt tctacgcagc tccttacagt | 960 |
| atcgcccaca gcaggatgct tgctcaatct gcgctagccc cgtatcttcc atctcctgtg | 1020 |
| tcttcctatc agggctcagt tctgacacca gggatggacc accccctctc tctccagcct | 1080 |
| gcctccatga tgggacctct tacccagcaa ctgggtcacc tgtcactcaa cagtctgggc | 1140 |
| acgttcatgc cggcagctgc tgctatgcat ggggcttaca ctcccagta cccagctgtg | 1200 |
| ccttcttcca gtgtttctgc tgaggagagc aatggccagc agaatcaact ggcagtggag | 1260 |
| cccccctcag accacgggt ctatccttc cagttcagca ataatgagg tccagacctg | 1320 |
| gggagagaag cctatgcagt cctccttggg ctccttcctg tggctgatgg aacctgagga | 1380 |
| atcacgttgg ttttttttt tgaatgtgct acattcaaga tcaaaagac ttttttttct | 1440 |
| tttgcaaaag aagtttcttg ctttgtattt aattgcagcg aacctttctc ctaccccaaa | 1500 |
| gacaccagtt gaggtgcttc tcatcttcga gaggtttggg tatgttgggc ttttaaaatg | 1560 |

```
gtttaagaac aatcgcagtg ctgtgaagtc agtgaagggg cgctgcttgc caggttcagt    1620
tagggactat tttcaatgtg tgttttagat atgcaggctt aaaactttg ttttgcaaag     1680 ctctcaacac acactttgca cacacccacc cacctccctc ccacgcactg tttaaggcag    1740
ggtctcacag tgcagtcctg gctggctgac aatgtagacc aggctggctt tgaactcagc   1800
gatccttccc actctgtctg agtgcaccgc catgcctagc tagttgtttt tttttttttg    1860 gtttttttt tttcaagaca gggtttctct gtgtagccct ggctgtcctg cgctcactt      1920 tgtagaccaa gctagcctcg aacttagaaa tccacctgcc tctgcctccc aagtgctggg    1980
attaaaggcg tgcgccacca ccgcccggct agttgttttt taaaacttct ccacaatggt    2040
ctttttttct tttccattta gcttagcctg cctactttgc cttttacaa tttttaattt     2100 tatgaatttg atttaaattt catgtggaat tgggggaagg gagagcaacg cacaggtaga    2160
gaagtgtggc agtagaggtt gctttccctc tgccctcctg gcctaggagg ggttagactt    2220
tgacttcagg aagcagacat gtgacaacca tgcagccttt ggaaaccacc ttcaaccaac    2280
tctggtggca agtgccactg agaagtggca tccagcttca gcatcctgga tacctgctct    2340
gcctcctgga gggtcttggg tcttcatcct gccccaggtc tcacagcccc tgcccctgct    2400
gagcaagttc tgccttccac tttaccagga ggttgttttg tccccgagag gctgctgtct    2460
tgtccatcat catccttgat taccaagcct ggggagtatc atgtgtgctg gtcctgaaca    2520
cctgacagaa cctggcccca ctcctccacc ccttattccc tggcagttat ttggtgtaga    2580
ctaaacccca gtccagcctt ggacatggag cctgttagtt catgtacttg ccagcagtg     2640 acatctgtga ctttgcctcc tggaggatct ttttctgcctg ggttctcaca gcctctcatc   2700
ccagctgcac atggctgtac tcaagtggta cttggctgaa tcacttaatt cagcaggagc    2760
catcttattt agcagggctc acccttggtt gtatgtacat gccaagtgca cacagtttga    2820
agggatgaaa gcaagaactg ttgtgtatac tgtgcatgct tgagaatgga ctgagctttc    2880
tctatgcagc atacccagcc cagccctggt gtttggaccc cttccccagg gaaccagacc    2940
accagaaata atttccttc ttgtggaagg acgacggggt gctaggatag aaaaaggcaa     3000
gactcacagc tccctggcca ctcaaaggtc aggagggact tgtaaacatg cctgccgtta    3060
actattccct tctgcaagac tttcagcaca aaatgtgact tgttacatca catcccttca    3120
cgtcataagt acacctccag tagacaaagc aatggagatg gggaagtgtg tccagaggtc    3180
agtgtgaaag aggaagggca gggcatggtg atggtgagaa actggctcag cagctgtgca    3240
cactacagaa ttgggaatcc tggcctgact gtgctgctgt cgttctaga ctgaggaagg     3300 ggctgaggac aatggacagc ataaagtaca aaatgaccag ttttctcatt ggtgcttcca    3360
acatcaggaa ggtcataccc agttatcgac ctctagccct ctagcactca gtgacagact    3420
cagagctctg tcctgtggaa accctgctga cagtcttgct gccactgctg ctccttcact    3480
gcctattaaa aattgttcct ttttctgtag ttctaaagca atttgaataa ctgacagttt    3540
taaaatttga aattaccttt ttaggttttt cttttgagta tactggttag ggttctagtg    3600
tttctggttg aacaggtgtg agcatgggaa atgagggcaa cctgtaattt tgttttata    3660 gtggttaatg gcactcactg tgtaatttct gcttagtgat ttccatccac tcttttcctc    3720
attagctcat tactcagaaa ggtagcgact gaagacagga agtagtatgc aagccatgag    3780
ggatgagttg taagcctcct ctccatcatc ctgcccaagg ctcctaacag tctcctgagt    3840
cctgtttgca tggaggccag atagatggct ctgcactcta tatctcacct gtactcattt    3900
```

```
tagtacattg tggttttgct tccaatcaat cagagtggac tagagctcac acctgacctc    3960
gtgtgactct tcactaggct ccaggcctat cccatctcat tgggtcagac tgtagatgga    4020
ctggactttt ggagacaggt cctgctatta cttaggaata tgtgggaaca atgatagga    4080
ccaagcttgt gaagcaaaac ggctttggaa agggcaagtg ctcaataata aaaatgggg    4140
tggaagtgaa gcgttatttg ctgagggttt cggaaggact agtttgtttt tgtccctggc    4200
ccttccggtc aagtgggcac ctcccatttt gtcgccaaga gcaatacagt tgagtaggtg    4260
gtagacccaa actcacccag ccatttctag acctgaattc agaggataag gtgagtctag    4320
aggtatatac aaccaatgct tgttagacca attcttacca attcggagca agccggtggc    4380
tctacttctg ggtaacctgc ctcttaaaag tgcctttgat cccagtagta gattcagggt    4440
ctacaggagc cttccctcag cagctaaaac caatttgtct cctctactct ttgctgcacc    4500
tcccggaggt ggtctccatg tggcagtgat gccctcatca ccttgtgac caccgctctg    4560
aatgttcaaa ataagcattt cctgtccaag caaatcccta aactccctcg tcctcattac    4620
tcaactacct cagtctgaca actcaaggca cacaagcacc tacttgcctc ccaccatcct    4680
ttactgccct tgtctttgtg gggttggaac aaatgcaaac tcctcagttc cacaacccaa    4740
aactgctctt tctggatcgt cttctccagt gacgttggct ccctacaaga gcgaactctc    4800
catatgggtc agtccctgta ggacaagcca gggactatgc tgtgcagtca atgccaggt    4860
ttggagcata gcttaagacc gcagagagta aggacttgag tggtggtggt gtgcagtttg    4920
agagagctgg aatggacgtc tctgctcctg ccctctgggc gggtcgggtg atgacttcta    4980
gatgcactcc ttaccctgga gggaagttaa tttatactta agatgcattt tgtacatttc    5040
ccctttaccc agaaacctgt agtttcatac tcccatgtct atgccaacac tacctatcgc    5100
tcactctccg tggctgactt ctggttccat ttccttcctg tgacttggaa gagctttact    5160
tttgctcacg tgaacctttc ttttttaaat aaaacacaaa agcctcc                   5207

<210> SEQ ID NO 5
<211> LENGTH: 383
<212> TYPE: PRT
<213> ORGANISM: Mus musculus

<400> SEQUENCE: 5

Met Leu Leu Ser Val Thr Ser Arg Pro Gly Ile Ser Thr Phe Gly Tyr
1               5                   10                  15

Asn Lys Asn Asn Lys Lys Leu Tyr Val Ala Gln Gln Met Ala Pro Pro
            20                  25                  30

Ser Pro Arg Asn Ser Thr Pro Asn Ser Ser Gly Gly Gly Gly Gly Gly
        35                  40                  45

Ser Gly Gly Asn Asp Gln Leu Ser Lys Thr Asn Leu Tyr Ile Arg Gly
    50                  55                  60

Leu Gln Pro Gly Thr Thr Asp Gln Asp Leu Val Lys Leu Cys Gln Pro
65                  70                  75                  80

Tyr Gly Lys Ile Val Ser Thr Lys Ala Ile Leu Asp Lys Thr Thr Asn
                85                  90                  95

Lys Cys Lys Gly Tyr Gly Phe Val Asp Phe Asp Ser Pro Ser Ser Ala
            100                 105                 110

Gln Lys Ala Val Thr Ala Leu Lys Ala Ser Gly Val Gln Ala Gln Met
        115                 120                 125

Ala Lys Gln Gln Glu Gln Asp Pro Thr Asn Leu Tyr Ile Ser Asn Leu
    130                 135                 140
```

```
Pro Leu Ser Met Asp Glu Gln Glu Leu Glu Gly Met Leu Lys Pro Phe
145                 150                 155                 160

Gly Gln Val Ile Ser Thr Arg Ile Leu Arg Asp Thr Ser Gly Ala Ser
            165                 170                 175

Arg Gly Val Gly Phe Ala Arg Met Glu Ser Thr Glu Lys Cys Glu Ala
            180                 185                 190

Ile Ile Thr His Phe Asn Gly Lys Tyr Ile Lys Thr Pro Pro Gly Val
            195                 200                 205

Ala Ala Pro Ser Asp Pro Leu Leu Cys Lys Phe Ala Asp Gly Gly Pro
            210                 215                 220

Lys Lys Arg Gln Ser Gln Gly Arg Tyr Val Gln Asn Gly Arg Ala Trp
225                 230                 235                 240

Pro Arg Asn Gly Asp Met Gly Gly Met Ala Leu Thr Tyr Asp Pro Thr
            245                 250                 255

Ala Ala Leu Gln Asn Gly Phe Tyr Ala Ala Pro Tyr Ser Ile Ala His
            260                 265                 270

Ser Arg Met Leu Ala Gln Ser Ala Leu Ala Pro Tyr Leu Pro Ser Pro
            275                 280                 285

Val Ser Ser Tyr Gln Gly Ser Val Leu Thr Pro Gly Met Asp His Pro
290                 295                 300

Leu Ser Leu Gln Pro Ala Ser Met Met Gly Pro Leu Thr Gln Gln Leu
305                 310                 315                 320

Gly His Leu Ser Leu Asn Ser Leu Gly Thr Phe Met Pro Ala Ala Ala
            325                 330                 335

Ala Met His Gly Ala Tyr Ile Ser Gln Tyr Pro Ala Val Pro Ser Ser
            340                 345                 350

Ser Val Ser Ala Glu Glu Ser Asn Gly Gln Gln Asn Gln Leu Ala Val
            355                 360                 365

Glu Pro Pro Ser Asp His Gly Val Tyr Pro Phe Gln Phe Ser Lys
            370                 375                 380

<210> SEQ ID NO 6
<211> LENGTH: 355
<212> TYPE: PRT
<213> ORGANISM: Mus musculus

<400> SEQUENCE: 6

Met Ala Pro Pro Ser Pro Arg Asn Ser Thr Pro Asn Ser Ser Gly Gly
1               5                   10                  15

Gly Gly Gly Gly Ser Gly Gly Asn Asp Gln Leu Ser Lys Thr Asn Leu
            20                  25                  30

Tyr Ile Arg Gly Leu Gln Pro Gly Thr Thr Asp Gln Asp Leu Val Lys
            35                  40                  45

Leu Cys Gln Pro Tyr Gly Lys Ile Val Ser Thr Lys Ala Ile Leu Asp
50                  55                  60

Lys Thr Thr Asn Lys Cys Lys Gly Tyr Gly Phe Val Asp Phe Asp Ser
65                  70                  75                  80

Pro Ser Ser Ala Gln Lys Ala Val Thr Ala Leu Lys Ala Ser Gly Val
            85                  90                  95

Gln Ala Gln Met Ala Lys Gln Gln Glu Gln Asp Pro Thr Asn Leu Tyr
            100                 105                 110

Ile Ser Asn Leu Pro Leu Ser Met Asp Glu Gln Glu Leu Glu Gly Met
            115                 120                 125

Leu Lys Pro Phe Gly Gln Val Ile Ser Thr Arg Ile Leu Arg Asp Thr
130                 135                 140
```

```
Ser Gly Ala Ser Arg Gly Val Gly Phe Ala Arg Met Glu Ser Thr Glu
145                 150                 155                 160

Lys Cys Glu Ala Ile Ile Thr His Phe Asn Gly Lys Tyr Ile Lys Thr
                165                 170                 175

Pro Pro Gly Val Ala Ala Pro Ser Asp Pro Leu Leu Cys Lys Phe Ala
            180                 185                 190

Asp Gly Gly Pro Lys Lys Arg Gln Ser Gln Gly Arg Tyr Val Gln Asn
        195                 200                 205

Gly Arg Ala Trp Pro Arg Asn Gly Asp Met Gly Gly Met Ala Leu Thr
    210                 215                 220

Tyr Asp Pro Thr Ala Ala Leu Gln Asn Gly Phe Tyr Ala Ala Pro Tyr
225                 230                 235                 240

Ser Ile Ala His Ser Arg Met Leu Ala Gln Ser Ala Leu Ala Pro Tyr
                245                 250                 255

Leu Pro Ser Pro Val Ser Ser Tyr Gln Gly Ser Val Leu Thr Pro Gly
            260                 265                 270

Met Asp His Pro Leu Ser Leu Gln Pro Ala Ser Met Met Gly Pro Leu
        275                 280                 285

Thr Gln Gln Leu Gly His Leu Ser Leu Asn Ser Leu Gly Thr Phe Met
    290                 295                 300

Pro Ala Ala Ala Ala Met His Gly Ala Tyr Ile Ser Gln Tyr Pro Ala
305                 310                 315                 320

Val Pro Ser Ser Ser Val Ser Ala Glu Glu Ser Asn Gly Gln Gln Asn
                325                 330                 335

Gln Leu Ala Val Glu Pro Pro Ser Asp His Gly Val Tyr Pro Phe Gln
            340                 345                 350

Phe Ser Lys
        355

<210> SEQ ID NO 7
<211> LENGTH: 5390
<212> TYPE: DNA
<213> ORGANISM: Mus musculus

<400> SEQUENCE: 7
acttcctgtc ctgttggaaa tgaaagttag gaattggggg tggtagccgt gcacgtattt      60
attctgcagc atgccggcac tgtctgtttc gttatcacag caaagcagcc gcaggaaaaa     120
cagagagcag agctttgttt tagagagagt ctgggcttga ggtctgttgt gacaaagacg     180
gagttaattt acttctggag aatgtgtgtg gcagcagtgg gaggcctgag gaggggctct     240
gaaggcattc agtctcccct cctgttctag gtggatggat aggcttcttt ggtatcactt     300
gtaagttttc ttttcctgtt ccaactcctc cttggagggc atattggagc tcagagagga     360
ctctgtgaac gtcatttggc ttggccataa attccacacc tgctatatgt ggctcagcaa     420
atggcacctc caagtccaag gaatagcacc cccaacagca gcggcggagg cggcggcggg     480
agtggtggga acgaccagct gagcaaaacc aacctgtata tccgaggact gcagccaggc     540
accactgacc aggaccttgt caagctctgt cagccgtatg gcaagattgt ctccactaag     600
gccatcctgg acaagaccac aaacaagtgc aaaggctatg ctttgtggat cttcgacagt     660
ccgtcatcag cacagaaagc tgtaactgca ctgaaagcca gtggtgtgca ggcacaaatg     720
gcaaagcaac aggagcaaga ccctacaaac ttatacatct caaacctccc tctgtcaatg     780
gacgagcagg aactggaggg gatgctgaag ccctttggcc aggtcatctc tactcggatc     840
```

```
cttcgagaca ctagtggggc cagcagaggg gtcggctttg caaggatgga gtcaacagag    900
aagtgtgaag ccatcatcac ccactttaat ggaaagtata taaagacacc ccctggagta    960
gcagcacctt ctgacccttt gctttgcaaa tttgctgacg gtgggccaaa gaaacgacag   1020
agccaaggaa gatacgtgca aaatggacgg gcctggccaa ggaacggaga catgggcggt   1080
atggccttga cctatgaccc cactgctgcc cttcagaatg ggttctacgc agctccttac   1140
agtatcgccc acagcaggat gcttgctcaa tctgcgctag ccccgtatct tccatctcct   1200
gtgtcttcct atcagggctc agttctgaca ccagggatgg accaccccct ctctctccag   1260
cctgcctcca tgatgggacc tcttacccag caactgggtc acctgtcact caacagtctg   1320
ggcacgttca tgccggcagc tgctgctatg catggggctt acatctccca gtacccagct   1380
gtgccttctt ccagtgtttc tgctgaggag agcaatggcc agcagaatca actggcagtg   1440 gagccccct cagaccacgg ggtctatcct ttccagttca gcaaataatg aggtccagac   1500
ctggggagag aagcctatgc agtcctcctt gggctccttc ctgtggctga tggaacctga   1560
ggaatcacgt tggttttttt ttttgaatgt gctacattca agatcaaaaa gacttttttt   1620
tcttttgcaa aagaagtttc ttgctttgta tttaattgca gcgaaccttt ctcctacccc   1680
aaagacacca gttgaggtgc ttctcatctt cgagaggttt gggtatgttg ggcttttaaa   1740
atggtttaag aacaatcgca gtgctgtgaa gtcagtgaag gggcgctgct tgccaggttc   1800
agttagggac tattttcaat gtgtgtttta gatatgcagg cttaaaactt ttgttttgca   1860
aagctctcaa cacacacttt gcacacaccc acccacctcc ctcccacgca ctgtttaagg   1920
cagggtctca cagtgcagtc ctggctggct gacaatgtag accaggctgg ctttgaactc   1980
agcgatcctt cccactctgt ctgagtgcac cgccatgcct agctagttgt ttttttttt   2040 ttggtttttt ttttttcaag acagggtttc tctgtgtagc cctggctgtc ctggcgctca   2100
ctttgtagac caagctagcc tcgaacttag aaatccacct gcctctgcct cccaagtgct   2160
gggattaaag gcgtgcgcca ccaccgcccg gctagttgtt ttttaaaact tctccacaat   2220 ggtcttttt tcttttccat ttagcttagc ctgcctactt tgccttttta caattttaa   2280 ttttatgaat ttgatttaaa tttcatgtgg aattggggga agggagagca acgcacaggt   2340
agagaagtgt ggcagtagag gttgctttcc ctctgccctc ctggcctagg aggggttaga   2400 cttgacttc aggaagcaga catgtgacaa ccatgcagcc tttggaaacc accttcaacc   2460
aactctggtg gcaagtgcca ctgagaagtg gcatccagct tcagcatcct ggataccttgc   2520 tctgcctcct ggagggtctt gggtcttcat cctgccccag gtctcacagc ccctgccct   2580 gctgagcaag ttctgccttc cactttacca ggaggttgtt ttgtccccga gaggctgctg   2640
tcttgtccat catcatccct gattaccaag cctggggagt atcatgtgtg ctggtcctga   2700
acacctgaca gaacctggcc ccactcctcc accccttatt ccctggcagt tatttggtgt   2760
agactaaacc ccagtccagc cttggacatg gagcctgtta gttcatgtac ttggccagca   2820
gtgacatctg tgactttgcc tcctggagga tcttttctgc ctgggttctc acagcctctc   2880
atcccagctg cacatggctg tactcaagtg gtacttggct gaatcactta attcagcagg   2940
agccatctta tttagcaggg ctcacccttg gttgtatgta catgccaagt gcacacagtt   3000
tgaagggatg aaagcaagaa ctgttgtgta tactgtgcat gcttgagaat ggactgagct   3060
ttctctatgc agcatacccca gcccagccct ggtgtttgga ccccttcccc agggaaccag   3120
accaccagaa ataattttcc ttcttgtgga aggacgacgg ggtgctagga tagaaaaagg   3180
caagactcac agctccctgg ccactcaaag gtcaggaggg acttgtaaac atgcctgccg   3240
```

```
ttaactattc ccttctgcaa gactttcagc acaaaatgtg acttgttaca tcacatccct    3300
tcacgtcata agtacacctc cagtagacaa agcaatggag atggggaagt gtgtccagag    3360
gtcagtgtga aagaggaagg gcagggcatg gtgatggtga gaaactggct cagcagctgt    3420
gcacactaca gaattgggaa tcctggcctg actgtgctgc tgtgcgttct agactgagga    3480
aggggctgag gacaatggac agcataaagt acaaaatgac cagttttctc attggtgctt    3540
ccaacatcag gaaggtcata cccagttatc gacctctagc cctctagcac tcagtgacag    3600
actcagagct ctgtcctgtg gaaaccctgc tgacagtctt gctgccactg ctgctccttc    3660
actgcctatt aaaaattgtt ccttttctg tagttctaaa gcaatttgaa taactgcacag    3720 tttttaaaatt tgaaattacc ttttaggtt tttcttttga gtatactggt tagggttcta    3780
gtgtttctgg ttgaacaggt gtgagcatgg gaaatgaggg caacctgtaa ttttgttttt    3840
atagtggtta atggcactca ctgtgtaatt tctgcttagt gatttccatc cactcttttc    3900
ctcattagct cattactcag aaaggtagcg actgaagaca ggaagtagta tgcaagccat    3960
gagggatgag ttgtaagcct cctctccatc atcctgccca aggctcctaa cagtctcctg    4020
agtcctgttt gcatggaggc cagatagatg gctctgcact ctatatctca cctgtactca    4080
ttttagtaca ttgtggtttt gcttccaatc aatcagagtg gactagagct cacacctgac    4140
ctcgtgtgac tcttcactag gctccaggcc tatcccatct cattgggtca gactgtagat    4200
ggactggact tttggagaca ggtcctgcta ttacttagga atatgtggga acaatgatag    4260
ggaccaagct tgtgaagcaa aacggcttg gaaagggcaa gtgctcaata ataaaaaatg    4320
gggtggaagt gaagcgttat ttgctgaggg tttcggaagg actagtttgt ttttgtccct    4380
ggcccttccg gtcaagtggg cacctcccat tttgtcgcca agagcaatac agttgagtag    4440
gtggtagacc caaactcacc cagccatttc tagacctgaa ttcagaggat aaggtgagtc    4500
tagaggtata tacaaccaat gcttgttaga ccaattctta ccaattcgga gcaagccggt    4560
ggctctactt ctgggtaacc tgcctcttaa aagtgccttt gatcccagta gtagattcag    4620
ggtctacagg agccttccct cagcagctaa accaatttg tctcctctac tctttgctgc    4680
acctcccgga ggtggtctcc atgtggcagt gatgccctca tcacccttgt gaccaccgct    4740
ctgaatgttc aaaataagca tttcctgtcc aagcaaatcc ctaaactccc tcgtcctcat    4800
tactcaacta cctcagtctg acaactcaag gcacacaagc acctacttgc ctcccaccat    4860
cctttactgc ccttgtcttt gtggggttgg aacaaatgca aactcctcag ttccacaacc    4920
caaaactgct ctttctggat cgtcttctcc agtgacgttg gctccctaca agagcgaact    4980
ctccatatgg gtcagtccct gtaggacaag ccagggacta tgctgtgcag tcaaatgcca    5040
ggtttggagc atagcttaag accgcagaga gtaaggactt gagtggtggt ggtgtgcagt    5100
ttgagagagc tggaatggac gtctctgctc ctgccctctg ggcgggtcgg gtgatgactt    5160
ctagatgcac tccttaccct ggagggaagt taatttatac ttaagatgca ttttgtacat    5220
ttccccttta cccagaaacc tgtagtttca tactcccatg tctatgccaa cactacctat    5280
cgctcactct ccgtggctga cttctggttc catttccttc ctgtgacttg gaagagcttt    5340
acttttgctc acgtgaacct ttcttttta aataaaacac aaaagcctcc                 5390
```

<210> SEQ ID NO 8
<211> LENGTH: 21
<212> TYPE: DNA
<213> ORGANISM: Artificial Sequence
<220> FEATURE:

```
<223> OTHER INFORMATION: Human RBMS2-1 siRNA

<400> SEQUENCE: 8
uuugcacaaa uuuccuugg t                                               21

<210> SEQ ID NO 9
<211> LENGTH: 21
<212> TYPE: DNA
<213> ORGANISM: Artificial Sequence
<220> FEATURE:
<223> OTHER INFORMATION: Human RBMS2-2 siRNA

<400> SEQUENCE: 9
ugcucaucca uugacagugg g                                              21

<210> SEQ ID NO 10
<211> LENGTH: 21
<212> TYPE: DNA
<213> ORGANISM: Artificial Sequence
<220> FEATURE:
<223> OTHER INFORMATION: Mouse RBMS2-1 siRNA

<400> SEQUENCE: 10
uaaggagcug cguagaaccc a                                              21

<210> SEQ ID NO 11
<211> LENGTH: 21
<212> TYPE: DNA
<213> ORGANISM: Artificial Sequence
<220> FEATURE:
<223> OTHER INFORMATION: Mouse RBMS2-2 siRNA

<400> SEQUENCE: 11
agauguauaa guuuguaggg t                                              21

<210> SEQ ID NO 12
<211> LENGTH: 20
<212> TYPE: DNA
<213> ORGANISM: Artificial Sequence
<220> FEATURE:
<223> OTHER INFORMATION: HumanRBMS2 Forward primer

<400> SEQUENCE: 12
catctctccc tcagcagcac                                                20

<210> SEQ ID NO 13
<211> LENGTH: 20
<212> TYPE: DNA
<213> ORGANISM: Artificial Sequence
<220> FEATURE:
<223> OTHER INFORMATION: HumanRBMS2 Reverse primer

<400> SEQUENCE: 13
gctgctctcc tcgactgaaa                                                20

<210> SEQ ID NO 14
<211> LENGTH: 20
<212> TYPE: DNA
<213> ORGANISM: Artificial Sequence
<220> FEATURE:
<223> OTHER INFORMATION: Human IL-6 Forward primer

<400> SEQUENCE: 14
ctccaggagc ccagctatga                                                20
```

```
<210> SEQ ID NO 15
<211> LENGTH: 20
<212> TYPE: DNA
<213> ORGANISM: Artificial Sequence
<220> FEATURE:
<223> OTHER INFORMATION: Human IL-6 Reverse primer

<400> SEQUENCE: 15
gaggtgagtg gctgtctgtg                                           20

<210> SEQ ID NO 16
<211> LENGTH: 20
<212> TYPE: DNA
<213> ORGANISM: Artificial Sequence
<220> FEATURE:
<223> OTHER INFORMATION: Luciferase Forward primer

<400> SEQUENCE: 16
gaaatgtccg ttcggttggc                                           20

<210> SEQ ID NO 17
<211> LENGTH: 20
<212> TYPE: DNA
<213> ORGANISM: Artificial Sequence
<220> FEATURE:
<223> OTHER INFORMATION: Luciferase Reverse primer

<400> SEQUENCE: 17
tccgataaat aacgcgccca                                           20

<210> SEQ ID NO 18
<211> LENGTH: 20
<212> TYPE: DNA
<213> ORGANISM: Artificial Sequence
<220> FEATURE:
<223> OTHER INFORMATION: Human IL1B Forward primer

<400> SEQUENCE: 18
cgaggcacaa ggcacaacag                                           20

<210> SEQ ID NO 19
<211> LENGTH: 20
<212> TYPE: DNA
<213> ORGANISM: Artificial Sequence
<220> FEATURE:
<223> OTHER INFORMATION: Human IL1B Reverse primer

<400> SEQUENCE: 19
agaggtccag gtcctggaag                                           20

<210> SEQ ID NO 20
<211> LENGTH: 20
<212> TYPE: DNA
<213> ORGANISM: Artificial Sequence
<220> FEATURE:
<223> OTHER INFORMATION: Human PTGS2 Forward primer

<400> SEQUENCE: 20
gttccacccg cagtacagaa                                           20

<210> SEQ ID NO 21
<211> LENGTH: 20
<212> TYPE: DNA
<213> ORGANISM: Artificial Sequence
<220> FEATURE:
<223> OTHER INFORMATION: Human PTGS2 Reverse primer
```

```
<400> SEQUENCE: 21
agggcttcag cataaagcgt                                                   20

<210> SEQ ID NO 22
<211> LENGTH: 20
<212> TYPE: DNA
<213> ORGANISM: Artificial Sequence
<220> FEATURE:
<223> OTHER INFORMATION: Human IL8 Forward primer

<400> SEQUENCE: 22
accggaagga accatctcac                                                   20

<210> SEQ ID NO 23
<211> LENGTH: 21
<212> TYPE: DNA
<213> ORGANISM: Artificial Sequence
<220> FEATURE:
<223> OTHER INFORMATION: Human IL8 Reverse primer

<400> SEQUENCE: 23
ggcaaaactg caccttcaca c                                                 21

<210> SEQ ID NO 24
<211> LENGTH: 20
<212> TYPE: DNA
<213> ORGANISM: Artificial Sequence
<220> FEATURE:
<223> OTHER INFORMATION: Human NFKBIA Forward primer

<400> SEQUENCE: 24
gggccagctg acactagaaa                                                   20

<210> SEQ ID NO 25
<211> LENGTH: 20
<212> TYPE: DNA
<213> ORGANISM: Artificial Sequence
<220> FEATURE:
<223> OTHER INFORMATION: Human NFKBIA Reverse primer

<400> SEQUENCE: 25
gtcatcatag ggcagctcgt                                                   20

<210> SEQ ID NO 26
<211> LENGTH: 20
<212> TYPE: DNA
<213> ORGANISM: Artificial Sequence
<220> FEATURE:
<223> OTHER INFORMATION: Human ZC3H12A Forward primer

<400> SEQUENCE: 26
gtctgacggg atcgtggttt                                                   20

<210> SEQ ID NO 27
<211> LENGTH: 20
<212> TYPE: DNA
<213> ORGANISM: Artificial Sequence
<220> FEATURE:
<223> OTHER INFORMATION: Human ZC3H12A Reverse primer

<400> SEQUENCE: 27 caggggggcat aaacttgtca                                                  20

<210> SEQ ID NO 28
<211> LENGTH: 21
```

```
<212> TYPE: DNA
<213> ORGANISM: Artificial Sequence
<220> FEATURE:
<223> OTHER INFORMATION: Mouse RBMS2 Forward primer

<400> SEQUENCE: 28
tgctgctatc agtgacttcc a                                              21

<210> SEQ ID NO 29
<211> LENGTH: 22
<212> TYPE: DNA
<213> ORGANISM: Artificial Sequence
<220> FEATURE:
<223> OTHER INFORMATION: Mouse RBMS2 Reverse primer

<400> SEQUENCE: 29
tgctgagcca catatagctt ct                                             22

<210> SEQ ID NO 30
<211> LENGTH: 20
<212> TYPE: DNA
<213> ORGANISM: Artificial Sequence
<220> FEATURE:
<223> OTHER INFORMATION: Mouse IL6 Forward primer

<400> SEQUENCE: 30
aggcataacg cactaggttt                                                20

<210> SEQ ID NO 31
<211> LENGTH: 20
<212> TYPE: DNA
<213> ORGANISM: Artificial Sequence
<220> FEATURE:
<223> OTHER INFORMATION: Mouse IL6 Reverse primer

<400> SEQUENCE: 31
agctggagtc acagaaggag                                                20

<210> SEQ ID NO 32
<211> LENGTH: 25
<212> TYPE: DNA
<213> ORGANISM: Artificial Sequence
<220> FEATURE:
<223> OTHER INFORMATION: Mouse IL1b Forward primer

<400> SEQUENCE: 32
caaccaacaa gtgatattct ccatg                                          25

<210> SEQ ID NO 33
<211> LENGTH: 21
<212> TYPE: DNA
<213> ORGANISM: Artificial Sequence
<220> FEATURE:
<223> OTHER INFORMATION: Mouse IL1b Reverse primer

<400> SEQUENCE: 33
gatccacact ctccagctgc a                                              21

<210> SEQ ID NO 34
<211> LENGTH: 20
<212> TYPE: DNA
<213> ORGANISM: Artificial Sequence
<220> FEATURE:
<223> OTHER INFORMATION: Mouse TNFa Forward primer

<400> SEQUENCE: 34
```
atggcctccc tctcatcagt                                                    20

<210> SEQ ID NO 35
<211> LENGTH: 20
<212> TYPE: DNA
<213> ORGANISM: Artificial Sequence
<220> FEATURE:
<223> OTHER INFORMATION: Mouse TNFa Reverse primer

<400> SEQUENCE: 35
cttggtggtt tgctacgacg                                                    20

<210> SEQ ID NO 36
<211> LENGTH: 1240
<212> TYPE: DNA
<213> ORGANISM: Artificial Sequence
<220> FEATURE:
<223> OTHER INFORMATION: IL-6 promoter

<400> SEQUENCE: 36
cctactttca gcctggaatc attctgaatg ctagctagat atctggagac aggtggacag        60
aaaaccagga actagtctga aaagaaact aaccaaaggg aagaagtctg tttaagtttg        120
acccagccta gaagacttga gcattggagg ggttattcag agtgagacgt accaccttca       180
gattcaaatc ctgtcatcca gtagaaggga gcttcaaaca caagctagct aagatacaat       240
gaggtccttc ttcgatatct ttatcttcca tataccatga atcaaagaaa cttcaacaac       300
atgaggactg caacagacct tcaagcctcc ttgcatgacc tggaaatgtt ttggggtgtc      360
ctggcagcag tgggatcagc actaacagat aagggcaact ctcacagaga ctaaaggtct      420
taactaagaa gatagccaag agaccactgg ggagaatgca gagaataggc ttggacttgg     480
aagccaagat tgcttgacaa cagacagaag atatttctgt acttcaccca ctttacccac       540
ctggcaactc ctggaaacaa ctgcacaaaa tttggaggtg aacaaaccat tagaaacaac       600
tggtcctgac aagacacagg aaaaacaagc aatatgcaac attactgtct gttgtccagg       660
ttgggtgctg ggggtgggag agggagtgtg tgtctttgta tgatctgaaa aaactcaggt       720
cagaacatct gtagatcctt acagacatac aaaagaatcc tagcctctta ttcatgtgtg       780
tgtgtgtgtg tgtgtgtgtg tgtgtgtgtg tgtgtgtgtg tatgtgtgtg tcgtctgtca       840
tgcgcgcgtg cctgcgttta aataacatca gctttagctt ctctttctcc ttataaaaca       900
ttgtgaattt cagttttctt tcccatcaag acatgctcaa gtgctgagtc acttttaaag       960
aaaaaaaga agagtgctca tgcttcttag ggctagcctc aaggatgact taagcacact       1020
ttcccccttcc tagttgtgat tctttcgatg ctaaacgacg tcacattgtg caatcttaat      1080
aaggtttcca atcagcccca cccactctgg ccccaccccc accctccaac aaagattttt      1140
atcaaatgtg ggatttttccc atgagtctca aaattagaga gttgactcct aataaatatg     1200
agactgggga tgtctgtagc tcattctgct ctggagccca                             1240

<210> SEQ ID NO 37
<211> LENGTH: 171
<212> TYPE: DNA
<213> ORGANISM: Artificial Sequence
<220> FEATURE:
<223> OTHER INFORMATION: IL-6 3'UTR 97-267

<400> SEQUENCE: 37
ctaaaagtat gagcgttagg acactatttt aattatttttt aatttattaa tatttaaata      60
tgtgaagctg agttaatttta tgtaagtcat atttatatttt ttaagaagta ccacttgaaa    120

```
catttttatgt attagttttg aaataataat ggaaagtggc tatgcagttt g       171
```

<210> SEQ ID NO 38
<211> LENGTH: 72
<212> TYPE: DNA
<213> ORGANISM: Artificial Sequence
<220> FEATURE:
<223> OTHER INFORMATION: IL-6 3'UTR 122-193

<400> SEQUENCE: 38

```
tattttaatt attttaatt tattaatatt taaatatgtg aagctgagtt aatttatgta    60
agtcatattt at                                                      72
```

<210> SEQ ID NO 39
<211> LENGTH: 39
<212> TYPE: DNA
<213> ORGANISM: Artificial Sequence
<220> FEATURE:
<223> OTHER INFORMATION: IL-6 3'UTR delta ARE1

<400> SEQUENCE: 39

```
tattttaatt attttaatt tattaatatt taaatatgt                          39
```

<210> SEQ ID NO 40
<211> LENGTH: 101
<212> TYPE: DNA
<213> ORGANISM: Artificial Sequence
<220> FEATURE:
<223> OTHER INFORMATION: IL-6 3'UTR delta ARE2

<400> SEQUENCE: 40

```
agttaattta tgtaagtcat atttatattt ttaagaagta ccacttgaaa catttttatgt  60 attagttttg aaataataat ggaaagtggc tatgcagttt g                     101
```

<210> SEQ ID NO 41
<211> LENGTH: 71
<212> TYPE: DNA
<213> ORGANISM: Artificial Sequence
<220> FEATURE:
<223> OTHER INFORMATION: IL-6 3'UTR ARE mutant

<400> SEQUENCE: 41

```
tattttaatt attttaagg gattaatagg gaaatatgtg aagctgagtt aagggatgta   60 agtcatagg a                                                       71
```

<210> SEQ ID NO 42
<211> LENGTH: 357
<212> TYPE: DNA
<213> ORGANISM: Artificial Sequence
<220> FEATURE:
<223> OTHER INFORMATION: IL-8 3'UTR wild type

<400> SEQUENCE: 42

```
ggatccacaa gtccttgttc cactgtgcct tggtttctcc tttatttcta agtggaaaaa   60
gtattagcca ccatcttacc tcacagtgat gttgtgagga catgtggaag cactttaagt  120
tttttcatca taacataaat tattttcaag tgtaacttat taacctatt attattttatg  180 tatttatttta agcatcaaat atttgtgcaa gaatttggaa aaatagaaga tgaatcattg  240
attgaatagt tataaagatg ttatagtaaa tttatttttat tttagatatt aaatgatgtt  300
ttattagata aatttcaatc agggttttta gattaaacaa acaaacaatt gggtacc      357
```

<210> SEQ ID NO 43
<211> LENGTH: 357
<212> TYPE: DNA
<213> ORGANISM: Artificial Sequence
<220> FEATURE:
<223> OTHER INFORMATION: IL-8 3'UTR mutant

<400> SEQUENCE: 43

```
ggatccacaa gtccttgttc cactgtgcct tggtttctcc tttatttcta agtggaaaaa    60
gtattagcca ccatcttacc tcacagtgat gttgtgagga catgtggaag cactttaagt   120
tttttcatca taacataaat tattttcaag tgtaacttat taacctaggg attagggatg   180
tagggaggga agcatcaaat atttgtgcaa gaatttggaa aaatagaaga tgaatcattg   240
attgaatagt tataaagatg ttatagtaaa tttatttat tttagatatt aaatgatgtt   300
ttattagata aatttcaatc agggttttta gattaaacaa acaaacaatt gggtacc     357
```

<210> SEQ ID NO 44
<211> LENGTH: 584
<212> TYPE: DNA
<213> ORGANISM: Artificial Sequence
<220> FEATURE:
<223> OTHER INFORMATION: IL1B 3'UTR wild type

<400> SEQUENCE: 44

```
agagagctgt acccagagag tcctgtgctg aatgtggact caatccctag ggctggcaga    60
aagggaacag aaaggttttt gagtacggct atagcctgga cttttcctgtt gtctacacca   120 atgcccaact gcctgcctta gggtagtgct aagaggatct cctgtccatc agccaggaca   180
gtcagctctc tcctttcagg gccaatcccc agccctttg ttgagccagg cctctctcac    240
ctctcctact cacttaaagc ccgcctgaca gaaaccacgg ccacatttgg ttctaagaaa   300
ccctctgtca ttcgctccca cattctgatg agcaaccgct tccctattta tttatttatt   360
tgtttgtttg ttttattcat tggtctaatt tattcaaagg gggcaagaag tagcagtgtc   420
tgtaaaagag cctagttttt aatagctatg gaatcaattc aatttggact ggtgtgctct   480
cttaaaatca gtcctttaa ttaagactga aaatatataa gctcagatta tttaaatggg   540
aatatttata aatgagcaaa tatcatactg ttcaatggtt ctga                    584
```

<210> SEQ ID NO 45
<211> LENGTH: 584
<212> TYPE: DNA
<213> ORGANISM: Artificial Sequence
<220> FEATURE:
<223> OTHER INFORMATION: IL1B 3'UTR mutant

<400> SEQUENCE: 45

```
agagagctgt acccagagag tcctgtgctg aatgtggact caatccctag ggctggcaga    60
aagggaacag aaaggttttt gagtacggct atagcctgga cttttcctgtt gtctacacca   120 atgcccaact gcctgcctta gggtagtgct aagaggatct cctgtccatc agccaggaca   180
gtcagctctc tcctttcagg gccaatcccc agccctttg ttgagccagg cctctctcac    240
ctctcctact cacttaaagc ccgcctgaca gaaaccacgg ccacatttgg ttctaagaaa   300
ccctctgtca ttcgctccca cattctgatg agcaaccgct tccctattta tttatttatt   360
tgtttgtttg ttttattcat tggtctaatt tattcaaagg gggcaagaag tagcagtgtc   420
tgtaaaagag cctagttttt aatagctatg gaatcaattc aatttggact ggtgtgctct   480
cttaaaatca gtcctttaa ttaagactga aaatatataa gctcagatta tttaaatggg   540
```
aatatttata aatgagcaaa tatcatactg ttcaatggtt ctga            584

<210> SEQ ID NO 46
<211> LENGTH: 304
<212> TYPE: PRT
<213> ORGANISM: Artificial Sequence
<220> FEATURE:
<223> OTHER INFORMATION: 3xFLAG- RBMS2 delta RRM1 domain

<400> SEQUENCE: 46

```
Met Asp Tyr Lys Asp His Asp Gly Asp Tyr Lys Asp His Asp Ile Asp
1               5                   10                  15

Tyr Lys Asp Asp Asp Lys Lys Leu Leu Glu Glu Gln Asp Pro Thr
            20                  25                  30

Asn Leu Tyr Ile Ser Asn Leu Pro Leu Ser Met Asp Glu Gln Glu Leu
        35                  40                  45

Glu Gly Met Leu Lys Pro Phe Gly Gln Val Ile Ser Thr Arg Ile Leu
    50                  55                  60

Arg Asp Thr Ser Gly Thr Ser Arg Gly Val Gly Phe Ala Arg Met Glu
65                  70                  75                  80

Ser Thr Glu Lys Cys Glu Ala Ile Ile Thr His Phe Asn Gly Lys Tyr
                85                  90                  95

Ile Lys Thr Pro Pro Gly Val Pro Ala Pro Ser Asp Pro Leu Leu Cys
            100                 105                 110

Lys Phe Ala Asp Gly Gly Pro Lys Lys Arg Gln Asn Gln Gly Lys Phe
        115                 120                 125

Val Gln Asn Gly Arg Ala Trp Pro Arg Asn Ala Asp Met Gly Val Met
    130                 135                 140

Ala Leu Thr Tyr Asp Pro Thr Thr Ala Leu Gln Asn Gly Phe Tyr Pro
145                 150                 155                 160

Ala Pro Tyr Asn Ile Thr Pro Asn Arg Met Leu Ala Gln Ser Ala Leu
                165                 170                 175

Ser Pro Tyr Leu Ser Ser Pro Val Ser Ser Tyr Gln Arg Val Thr Gln
            180                 185                 190

Thr Ser Pro Leu Gln Val Pro Asn Pro Ser Trp Met His His His Ser
        195                 200                 205

Tyr Leu Met Gln Pro Ser Gly Ser Val Leu Thr Pro Gly Met Asp His
    210                 215                 220

Pro Ile Ser Leu Gln Pro Ala Ser Met Met Gly Pro Leu Thr Gln Gln
225                 230                 235                 240

Leu Gly His Leu Ser Leu Ser Ser Thr Gly Thr Tyr Met Pro Thr Ala
                245                 250                 255

Ala Ala Met Gln Gly Ala Tyr Ile Ser Gln Tyr Thr Pro Val Pro Ser
            260                 265                 270

Ser Ser Val Ser Val Glu Glu Ser Ser Gly Gln Gln Asn Gln Val Ala
        275                 280                 285

Val Asp Ala Pro Ser Glu His Gly Val Tyr Ser Phe Gln Phe Asn Lys
    290                 295                 300
```

<210> SEQ ID NO 47
<211> LENGTH: 321
<212> TYPE: PRT
<213> ORGANISM: Artificial Sequence
<220> FEATURE:
<223> OTHER INFORMATION: 3xFLAG- RBMS2 delta RRM2 domain

<400> SEQUENCE: 47

Met Asp Tyr Lys Asp His Asp Gly Asp Tyr Lys Asp His Asp Ile Asp
1               5                   10                  15

Tyr Lys Asp Asp Asp Lys Lys Leu Ala Pro Pro Ser Pro Ser Asn
            20                  25                  30

Ser Thr Pro Asn Ser Ser Gly Ser Asn Gly Asn Asp Gln Leu Ser
            35                  40                  45

Lys Thr Asn Leu Tyr Ile Arg Gly Leu Gln Pro Gly Thr Thr Asp Gln
            50                  55                  60

Asp Leu Val Lys Leu Cys Gln Pro Tyr Gly Lys Ile Val Ser Thr Lys
65                  70                  75                  80

Ala Ile Leu Asp Lys Thr Thr Asn Lys Cys Lys Gly Tyr Gly Phe Val
                85                  90                  95

Asp Phe Asp Ser Pro Ser Ala Ala Gln Lys Ala Val Thr Ala Leu Lys
                100                 105                 110

Ala Ser Gly Val Gln Ala Gln Met Ala Lys Gln Gln Glu Gln Asp Pro
            115                 120                 125

Cys Lys Phe Ala Asp Gly Gly Pro Lys Lys Arg Gln Asn Gln Gly Lys
130                 135                 140

Phe Val Gln Asn Gly Arg Ala Trp Pro Arg Asn Ala Asp Met Gly Val
145                 150                 155                 160

Met Ala Leu Thr Tyr Asp Pro Thr Thr Ala Leu Gln Asn Gly Phe Tyr
                165                 170                 175

Pro Ala Pro Tyr Asn Ile Thr Pro Asn Arg Met Leu Ala Gln Ser Ala
                180                 185                 190

Leu Ser Pro Tyr Leu Ser Ser Pro Val Ser Ser Tyr Gln Arg Val Thr
            195                 200                 205

Gln Thr Ser Pro Leu Gln Val Pro Asn Pro Ser Trp Met His His
            210                 215                 220

Ser Tyr Leu Met Gln Pro Ser Gly Ser Val Leu Thr Pro Gly Met Asp
225                 230                 235                 240

His Pro Ile Ser Leu Gln Pro Ala Ser Met Met Gly Pro Leu Thr Gln
                245                 250                 255

Gln Leu Gly His Leu Ser Leu Ser Ser Thr Gly Thr Tyr Met Pro Thr
            260                 265                 270

Ala Ala Ala Met Gln Gly Ala Tyr Ile Ser Gln Tyr Thr Pro Val Pro
            275                 280                 285

Ser Ser Ser Val Ser Val Glu Glu Ser Ser Gly Gln Gln Asn Gln Val
            290                 295                 300

Ala Val Asp Ala Pro Ser Glu His Gly Val Tyr Ser Phe Gln Phe Asn
305                 310                 315                 320

Lys

<210> SEQ ID NO 48
<211> LENGTH: 216
<212> TYPE: PRT
<213> ORGANISM: Artificial Sequence
<220> FEATURE:
<223> OTHER INFORMATION: 3xFLAG- RBMS2 delta RRM1/2 domain

<400> SEQUENCE: 48

Met Asp Tyr Lys Asp His Asp Gly Asp Tyr Lys Asp His Asp Ile Asp
1               5                   10                  15

Tyr Lys Asp Asp Asp Asp Lys Lys Leu Leu Glu Asp Gly Gly Pro Lys
            20                  25                  30

```
Lys Arg Gln Asn Gln Gly Lys Phe Val Gln Asn Gly Arg Ala Trp Pro
                35                  40                  45

Arg Asn Ala Asp Met Gly Val Met Ala Leu Thr Tyr Asp Pro Thr Thr
 50                  55                  60

Ala Leu Gln Asn Gly Phe Tyr Pro Ala Pro Tyr Asn Ile Thr Pro Asn
 65                  70                  75                  80

Arg Met Leu Ala Gln Ser Ala Leu Ser Pro Tyr Leu Ser Ser Pro Val
                 85                  90                  95

Ser Ser Tyr Gln Arg Val Thr Gln Thr Ser Pro Leu Gln Val Pro Asn
                100                 105                 110

Pro Ser Trp Met His His His Ser Tyr Leu Met Gln Pro Ser Gly Ser
                115                 120                 125

Val Leu Thr Pro Gly Met Asp His Pro Ile Ser Leu Gln Pro Ala Ser
        130                 135                 140

Met Met Gly Pro Leu Thr Gln Gln Leu Gly His Leu Ser Leu Ser Ser
145                 150                 155                 160

Thr Gly Thr Tyr Met Pro Thr Ala Ala Met Gln Gly Ala Tyr Ile
                165                 170                 175

Ser Gln Tyr Thr Pro Val Pro Ser Ser Ser Val Ser Val Glu Glu Ser
                180                 185                 190

Ser Gly Gln Gln Asn Gln Val Ala Val Asp Ala Pro Ser Glu His Gly
                195                 200                 205

Val Tyr Ser Phe Gln Phe Asn Lys
        210                 215

<210> SEQ ID NO 49
<211> LENGTH: 34
<212> TYPE: PRT
<213> ORGANISM: Artificial Sequence
<220> FEATURE:
<223> OTHER INFORMATION: Deleted RBMS2 sequence

<400> SEQUENCE: 49

Leu Thr Pro Asp Gln Val Val Ala Ile Ala Ser Asn Ile Gly Gly Lys
1               5                   10                  15

Gln Ala Leu Glu Thr Val Gln Arg Leu Leu Pro Val Leu Cys Gln Asp
                20                  25                  30

His Gly

<210> SEQ ID NO 50
<211> LENGTH: 13
<212> TYPE: DNA
<213> ORGANISM: Artificial Sequence
<220> FEATURE:
<223> OTHER INFORMATION: TALEN sequence

<400> SEQUENCE: 50
atcgagagcc aat                                                          13
```